US011814626B2

(12) United States Patent
Nguyen et al.

(10) Patent No.: US 11,814,626 B2
(45) Date of Patent: Nov. 14, 2023

(54) COMPOSITIONS AND METHODS FOR LOADING EXTRACELLULAR VESICLES WITH CHEMICAL AND BIOLOGICAL AGENTS/MOLECULES

(71) Applicant: The Research Foundation for The State University of New York, Buffalo, NY (US)

(72) Inventors: Juliane Nguyen, Buffalo, NY (US); Scott Ferguson, North Tonawanda, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 838 days.

(21) Appl. No.: 16/612,734

(22) PCT Filed: May 11, 2018

(86) PCT No.: PCT/US2018/032226

§ 371 (c)(1),
(2) Date: Nov. 11, 2019

(87) PCT Pub. No.: WO2018/209182

PCT Pub. Date: Nov. 15, 2018

(65) Prior Publication Data

US 2020/0080092 A1 Mar. 12, 2020

Related U.S. Application Data

(60) Provisional application No. 62/631,060, filed on Feb. 15, 2018, provisional application No. 62/504,941, filed on May 11, 2017.

(51) Int. Cl.

| | |
|---|---|
| ***C12N 15/63*** | (2006.01) |
| ***A61K 9/50*** | (2006.01) |
| ***A61K 31/713*** | (2006.01) |
| ***C12N 15/11*** | (2006.01) |

(52) U.S. Cl.

CPC ............ *C12N 15/63* (2013.01); *A61K 9/5068* (2013.01); *A61K 31/713* (2013.01); *C12N 15/111* (2013.01); *C12N 2310/141* (2013.01); *C12N 2310/20* (2017.05); *C12N 2310/3519* (2013.01); *C12N 2320/32* (2013.01)

(58) Field of Classification Search

CPC .................. C12N 15/63; C12N 15/111; C12N 2310/141; C12N 2310/20; C12N 2310/3519; C12N 2320/32; A61K 9/5068; A61K 31/713

See application file for complete search history.

(56) References Cited

U.S. PATENT DOCUMENTS

| | | | | |
|---|---|---|---|---|
| 2014/0107189 A1 | | 4/2014 | Bancel et al. | |
| 2015/0232881 A1 | * | 8/2015 | Glucksmann | C12N 15/1137 435/468 |

FOREIGN PATENT DOCUMENTS

| | | | |
|---|---|---|---|
| WO | 2001/77384 | A2 | 10/2001 |
| WO | 2013/109713 | A1 | 7/2013 |

OTHER PUBLICATIONS

Genbank submission FN376847, Aspergillus fumigatus partitivirus 1 RdRp gene for RNA-dependent RNA polymerase, segment 1, genomic RNA, isolate 88, Sep. 19, 2011, Genbank database, 2 pages. https://www.ncbi.nlm.nih.gov/nuccore/FN376847.

Szostak, N. et al., Sorting signal targeting mRNA into hepatic extracellular vesicles, RNA Biology, Jul. 26, 2014, vol. 11, No. 7, pp. 836-844.

Bolukbasi, M. F. et al., miR-1289 and "Zipcode"-like Sequence Enrich mRNAs in Microvesicles, Molecular Therapy: Nucleic Acids, Feb. 7, 2012, vol. 1, pp. 1-10.

Kossinova, O. A. et al., Cytosolic YB-1 and NSUN2 are the only proteins recognizing specific motifs present in mRNAs enriched in exosomes, BBA—Proteins and Proteomics, Mar. 21, 2017, vol. 1865, No. 6, pp. 664-673.

Batagov, A. O. et al., Identification of nucleotide patterns enriched in secreted RNAs as putative cis-acting elements targeting them to exosome nano-vesicles, BMC Genomics, Nov. 30, 2011, vol. 12, No. suppl. 3, pp. 1-14.

Santangelo, L. et al., The RNA-Binding Protein SYNCRIP Is a Component of the Hepatocyte Exosomal Machinery Controlling MicroRNA Sorting, Cell Reports, Oct. 11, 2016, vol. 17, No. 3, pp. 799-808.

Wei, H. et al., Regulation of exosome production and cargo sorting, International Journal of Biological Sciences, vol. 17, No. 1, pp. 163-177.

* cited by examiner

*Primary Examiner* — J. E. Angell

(74) *Attorney, Agent, or Firm* — Hodgson Russ LLP

(57) ABSTRACT

Presented are RNA nucleotide sequences referred to as EXO-Codes, and longer RNA polynucleotides that contain the EXO-Codes. EXO-Codes provide RNA with the ability to a) be selectively sorted to extracellular vesicles such as exosomes, and b) deliver a variety of cargo types to program or reprogram the extracellular vesicles, and cells that receive the exosomes. Also presented are methods of making the EXO-Codes, modifying cells using the EXO-Codes, expression vectors encoding the EXO-Codes, and exosomes and other secreted vesicles that include RNA polynucleotides that contain the EXO-Codes.

3 Claims, 28 Drawing Sheets

Specification includes a Sequence Listing.

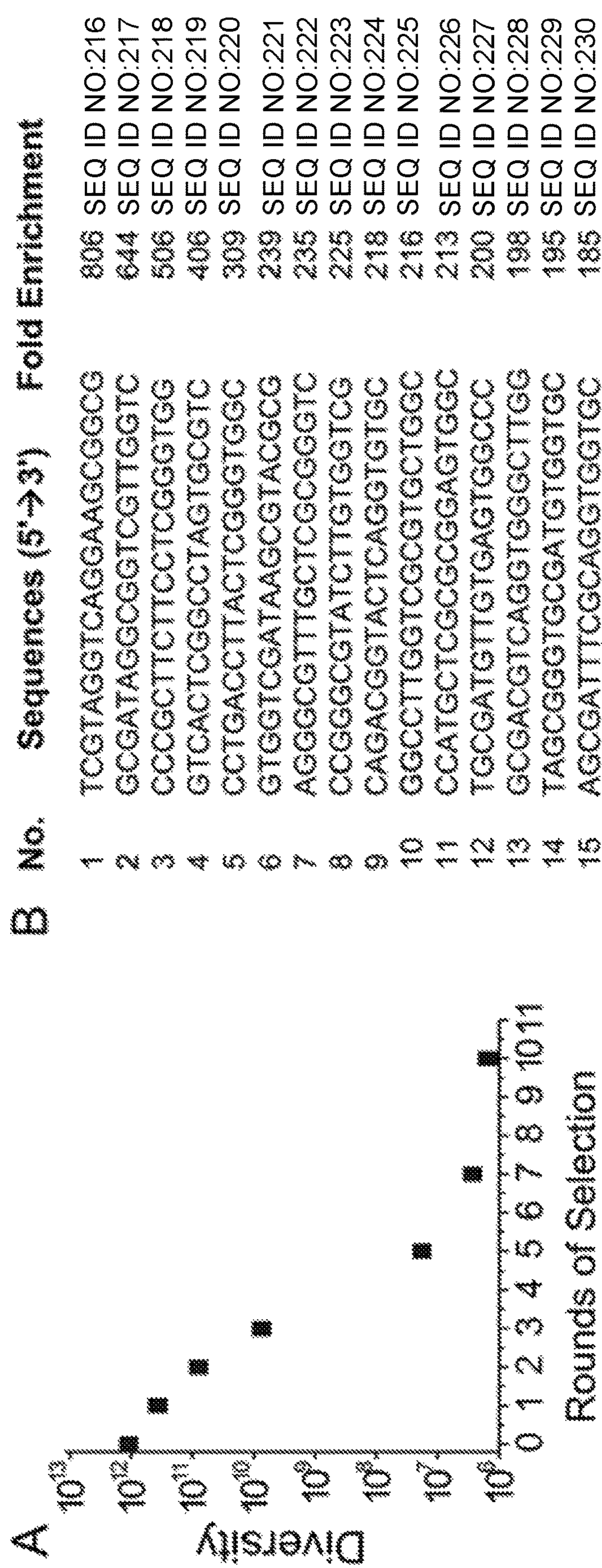

| No. | Sequences (5'→3') | Fold Enrichment | |
|---|---|---|---|
| 1 | TCGTAGGTCAGGAAGCGGCG | 806 | SEQ ID NO:216 |
| 2 | GCGATAGGCGGTCGTTGGTC | 644 | SEQ ID NO:217 |
| 3 | CCCGCTTCTTCCTCGGGTGG | 506 | SEQ ID NO:218 |
| 4 | GTCACTCGGCCTAGTGCGTC | 406 | SEQ ID NO:219 |
| 5 | CCTGACCTTACTCGGGTGGC | 309 | SEQ ID NO:220 |
| 6 | GTGGTCGATAAGCGTACGCG | 239 | SEQ ID NO:221 |
| 7 | AGGGCGTTTGCTCGCGGGTC | 235 | SEQ ID NO:222 |
| 8 | CCGGGCGTATCTTGTGGTCG | 225 | SEQ ID NO:223 |
| 9 | CAGACGGTACTCAGGTGTGC | 218 | SEQ ID NO:224 |
| 10 | GGCCTTGGTCGCGTGCTGGC | 216 | SEQ ID NO:225 |
| 11 | CCATGCTCGCGCGGAGTGGC | 213 | SEQ ID NO:226 |
| 12 | TGCGATGTTGTGAGTGGCCC | 200 | SEQ ID NO:227 |
| 13 | GCGACGTCAGGTGGGCTTGG | 198 | SEQ ID NO:228 |
| 14 | TAGCGGGTGCGATGTGGTGC | 195 | SEQ ID NO:229 |
| 15 | AGCGATTTCGCAGGTGGTGC | 185 | SEQ ID NO:230 |

Figure 5

| IUPAC nucleotide code |
| --- |
| WWMGYGCWYMYW<br>SEQ ID NO:231 |
| CCYNKVRAHCC<br>SEQ ID NO:232 |
| CYGSRYUKRGRG<br>SEQ ID NO:233 |

| IUPAC nucleotide code | Base |
| --- | --- |
| A | Adenine |
| C | Cytosine |
| G | Guanine |
| T (or U) | Thymine (or Uracil) |
| R | A or G |
| Y | C or T/U |
| S | G or C |
| W | A or T/U |
| K | G or T/U |
| M | A or C |
| B | C or G or T/U |
| D | A or G or T/U |
| H | A or C or T/U |
| V | A or C or G |
| N | any base |

Figure 7

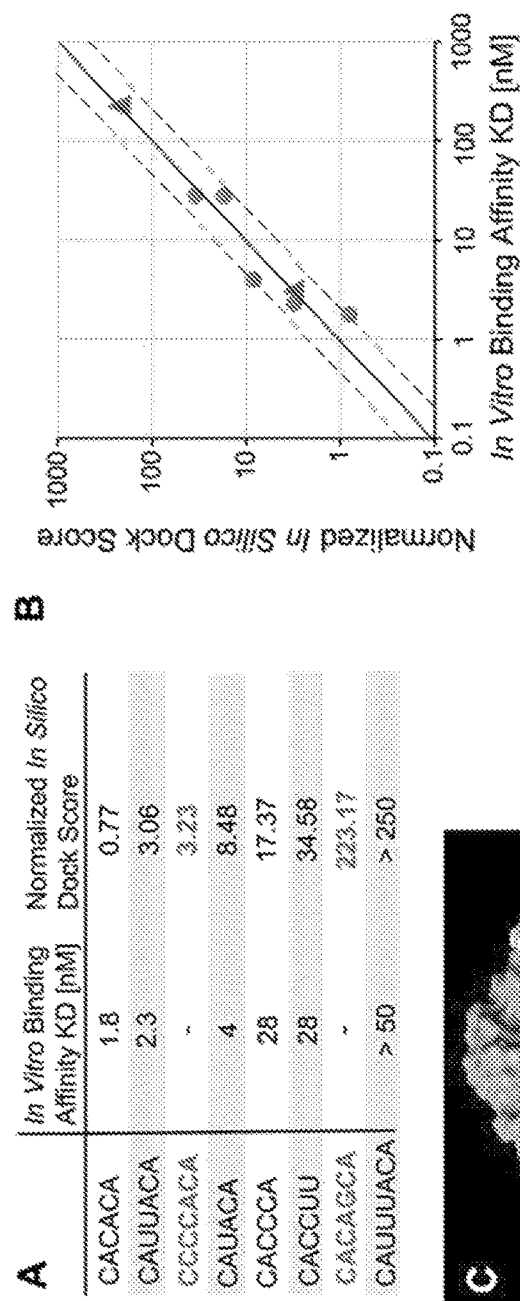
A
| | *In Vitro* Binding Affinity KD [nM] | Normalized *In Silico* Dock Score |
|---|---|---|
| CACACA | 1.8 | 0.77 |
| CAUUACA | 2.3 | 3.06 |
| CCCCACA | - | 3.23 |
| CAUACA | 4 | 8.48 |
| CACCCA | 28 | 17.37 |
| CACCUU | 28 | 34.58 |
| CACAGCA | - | 223.17 |
| CAUUUACA | > 50 | > 250 |
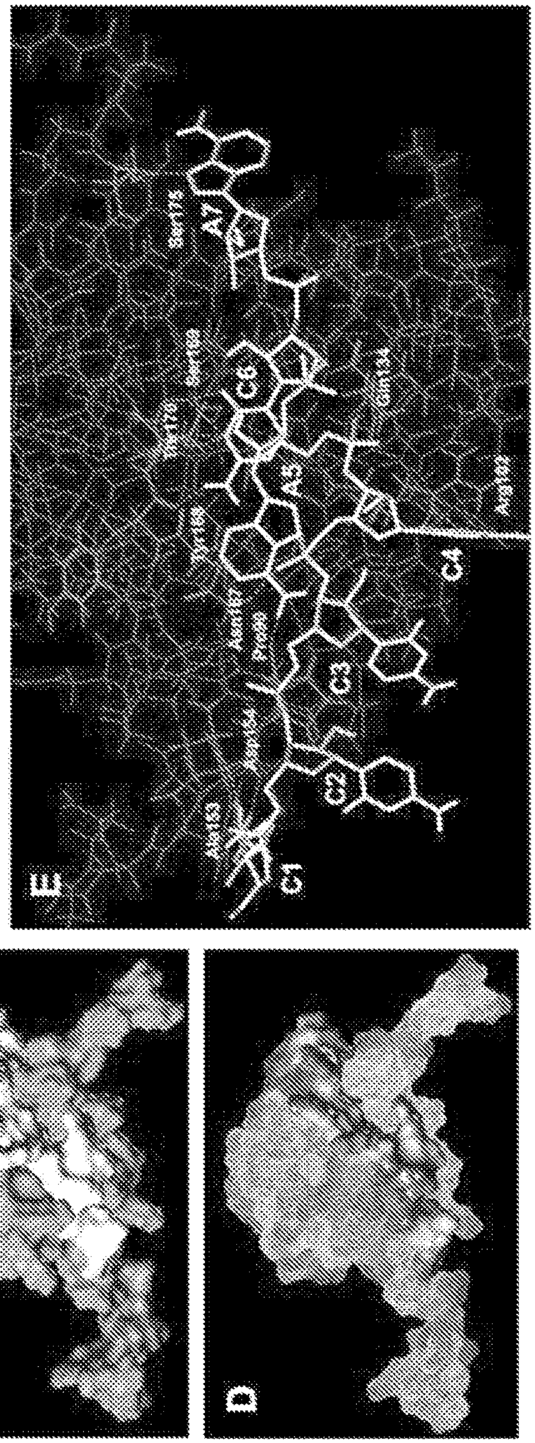
Figure 8

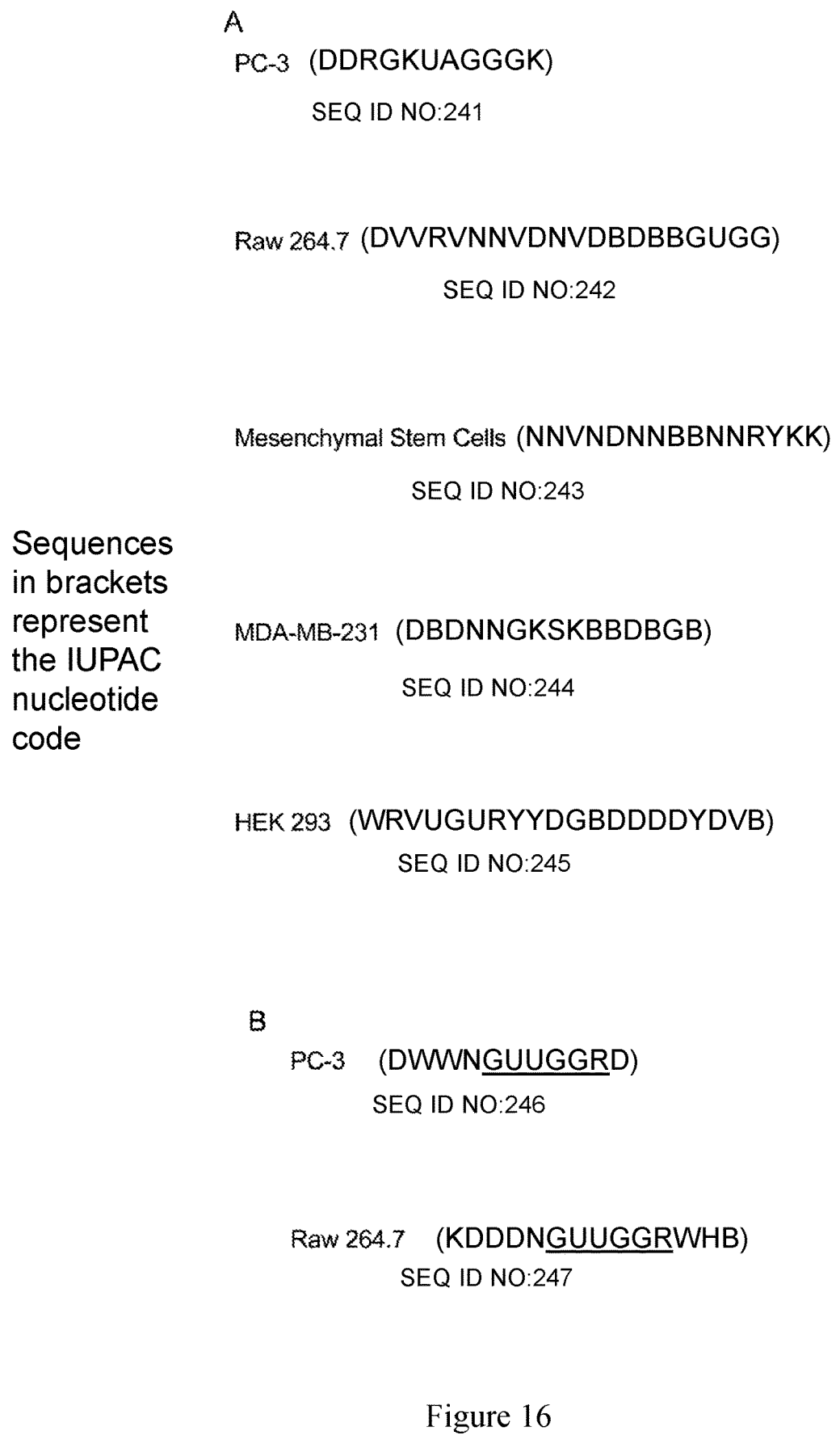

A

PC-3 (DDRGKUAGGGK)
SEQ ID NO:241

Raw 264.7 (DVVRVNNVDNVDBDBBGUGG)
SEQ ID NO:242

Mesenchymal Stem Cells (NNVNDNNBBNNRYKK)
SEQ ID NO:243

Sequences in brackets represent the IUPAC nucleotide code

MDA-MB-231 (DBDNNGKSKBBDBGB)
SEQ ID NO:244

HEK 293 (WRVUGURYYDGBDDDDYDVB)
SEQ ID NO:245

B

PC-3 (DWWNGUUGGRD)
SEQ ID NO:246

Raw 264.7 (KDDDNGUUGGRWHB)
SEQ ID NO:247

Figure 16

In silico predicted motifs

MDA top 16σ

| IUPAC | E-value |
|---|---|
| SSSCAAGUGGC (SEQ ID NO:248) | 3.3e-29 |
| ACWCGAGWKGC (SEQ ID NO:249) | 1.7e-03 |
| UGGCKUGUGGCU (SEQ ID NO:250) | 4.9e-02 |
| AWCUUGUGGUC (SEQ ID NO:251) | 2.3e-15 |
| DDGUGGNYGUGC (SEQ ID NO:252) | 7.7e-23 |
| VGUGKGKUGUGC (SEQ ID NO:253) | 1.6e-12 |
| WGCGASGUSGYG (SEQ ID NO:254) | 2.7e-06 |
| CMYCACAKCMGY (SEQ ID NO:255) | 3.8e-03 |

GUGGC

AGCGA

MSCs top 16σ

| IUPAC | E-value |
|---|---|
| RNRDGUGGCRUG (SEQ ID NO:256) | 3.0e-52 |
| SKMDRGUGGCY (SEQ ID NO:257) | 3.7e-13 |
| GSGCGKHGUGGY (SEQ ID NO:258) | 8.9e-09 |
| AGCGAYGKUGYG (SEQ ID NO:259) | 2.5e-36 |
| UAGCGRGUGCG (SEQ ID NO:260) | 3.9e-05 |
| AGMGRYGGUCGU (SEQ ID NO:261) | 2.0e-03 |
| GCGUADKKBGBG (SEQ ID NO:262) | 4.7e-17 |
| UASGUUGGRAMG (SEQ ID NO:263) | 5.3e-17 |
| AUGCGGGGC (SEQ ID NO:264) | 1.3e-05 |
| ARABMDAGGYGC (SEQ ID NO:265) | 2.0e-05 |

Figure 18

In silico predicted motifs

MSCs top 16σ

| IUPAC | E-value |
| --- | --- |
| RNRDGUGGCRUG (SEQ ID NO:256) | 3.0e-52 |
| SKMDRGUGGCY (SEQ ID NO:257) | 3.7e-13 |
| GSGCGKHGUGGY (SEQ ID NO:258) | 8.9e-09 |
| AGCGAYGKUGYG (SEQ ID NO:259) | 2.5e-36 |
| UAGCGRGUGCG (SEQ ID NO:260) | 3.9e-05 |
| AGMGRYGGUCGU (SEQ ID NO:261) | 2.0e-03 |
| GCGUADKKBGBG (SEQ ID NO:262) | 4.7e-17 |
| UASGUUGGRAMG (SEQ ID NO:263) | 5.3e-17 |
| AUGCGGGGGC (SEQ ID NO:264) | 1.3e-05 |
| ARABMDAGGYGC (SEQ ID NO:265) | 2.0e-05 |

RAW top 16σ

| IUPAC | E-value |
| --- | --- |
| AGUUGGAANGCG (SEQ ID NO:266) | 2.0e-023 |
| GNRWGCGGKGGC (SEQ ID NO:267) | 3.5e-021 |
| UGURCWNKNWW (SEQ ID NO:268) | 6.6e-017 |
| HGGRGSAGUGG (SEQ ID NO:269) | 9.1e-008 |
| RNNRRWGCGGGG (SEQ ID NO:270) | 4.6e-007 |
| KMGURWRUCNW (SEQ ID NO:271) | 3.4e-006 |
| KRDNWGGUGGCH (SEQ ID NO:272) | 1.5e-005 |
| GGGGGCRUAUG (SEQ ID NO:273) | 6.7e-003 |

Figure 18 (cont.)

Controls

| | | |
|---|---|---|
| RC | ACAGUAGAGCCUUGACCGGC | SEQ ID NO:236 |
| RC #2 | AUUCGUCGAGUACAGACCUG | SEQ ID NO:274 |
| Scramble | GCGCAGGGAGGGCUUGGGUC | SEQ ID NO:275 |

MSC in silico motifs

| | | |
|---|---|---|
| BS1 | GUGGCGUG | |
| BS2 | AGCGACGUUGCG | SEQ ID NO:276 |
| BS3 | GCGUAUGGCGUG | SEQ ID NO:277 |
| BS4 | UAGGUUGGAAAG | SEQ ID NO:278 |
| BS5 | GUGGCU | |
| BS6 | GGGCGUCGUGGC | SEQ ID NO:279 |
| BS5-6t | GUGGC | |
| BS7 | AUGCGGGGGC | SEQ ID NO:280 |
| BS7t | GCGGGG | |
| HYBRID | AAGUGGCGUG | SEQ ID NO:281 |

MDA-MB-231 in silico motifs

| | | |
|---|---|---|
| BM1 | CCGCAAGUGGC | SEQ ID NO:282 |
| BM1t | AAGUGGC | |
| BM2 | AUCUUGUGGUC | SEQ ID NO:283 |
| BM2t | CUUGUGGU | |
| BM3 | GUGGUUGUGC | SEQ ID NO:284 |
| BM3-4t | UGUGC | |
| BM4 | GUGUGGUGUGC | SEQ ID NO:285 |
| BM5 | GCGACGUGG | |
| BM6 | ACUCGAGUGGC | SEQ ID NO:286 |
| BM7 | CCCCACAGCAGU | SEQ ID NO:287 |
| BM12 | UGGCGUGUGGCU | SEQ ID NO:288 |
| HYBRID | AAGUGGCGUG | SEQ ID NO:289 |

Figure 19 (cont.)

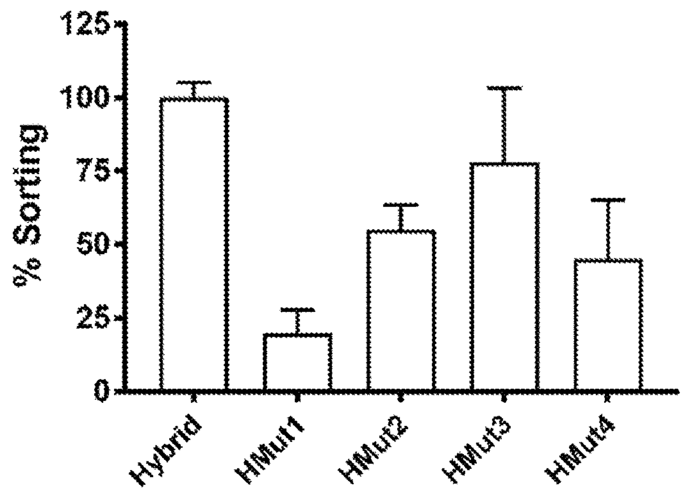

Hybrid: 5'-AAGUGGCGUG-3' SEQ ID NO:290
H-Mut1: 5'-AAGAGGCGUG-3' SEQ ID NO:291
H-Mut2: 5'-AAGUCGCGUG-3' SEQ ID NO:292
H-Mut3: 5'-AAGUGCCGUG-3' SEQ ID NO:293
H-Mut4: 5'-AAGUGGAGUG-3' SEQ ID NO:294

Figure 21

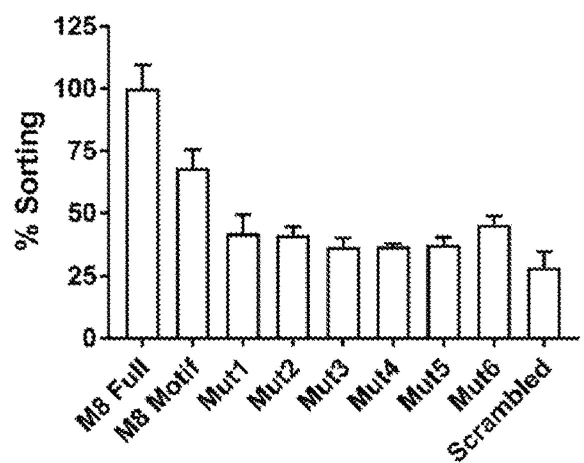

M8 Full: 5'-CCGGGCGUAUCUUGUGGUCG-3' SEQ ID NO:295
M8 Motif 5'-AUCUUGUGGUC-3' SEQ ID NO:296
Scramble 5'-GUGCUUCUGUA-3' SEQ ID NO:297
Mut1: 5'-AUGUUGUGGUC-3' SEQ ID NO:298
Mut 2: 5'-AUCUUCUGGUC-3' SEQ ID NO:299
Mut 3: 5'-AUCUUGAGGUC-3' SEQ ID NO:300
Mut 4: 5'-AUCUUGUCGUC-3' SEQ ID NO:301
Mut 5: 5'-AUCUUGUGCUC-3' SEQ ID NO:302
Mut 6: 5'-AUCUUGUGGAC-3' SEQ ID NO:303

Figure 22

| | | |
|---|---|---|
| S6: | 5'-AUGCGGGGGC-3' | SEQ ID NO:304 |
| Scramble: | 5'-GGUCGGACGG-3' | SEQ ID NO:305 |
| S-Mut1: | 5'-**U**UGCGGGGGC-3' | SEQ ID NO:306 |
| S-Mut2: | 5'-A**A**GCGGGGGC-3' | SEQ ID NO:307 |
| S-Mut3: | 5'-AU**C**CGGGGGC-3' | SEQ ID NO:308 |
| S-Mut4: | 5'-AUG**G**GGGGGC-3' | SEQ ID NO:309 |
| S-Mut5: | 5'-AUGC**C**GGGGC-3' | SEQ ID NO:310 |
| S-Mut6: | 5'-AUGCG**C**GGGC-3' | SEQ ID NO:311 |
| S-Mut7: | 5'-AUGCGG**C**GGC-3' | SEQ ID NO:312 |
| S-Mut8: | 5'-AUGCGGG**C**GC-3' | SEQ ID NO:313 |

SEQUENCE LISTING

```
<160> NUMBER OF SEQ ID NOS: 313

<210> SEQ ID NO 1
<211> LENGTH: 23
<212> TYPE: RNA
<213> ORGANISM: Artificial Sequence
<220> FEATURE:
<223> OTHER INFORMATION: Excluded EXO-code

<400> SEQUENCE: 1

uagggaagag aaggacauau gau                                              23


<210> SEQ ID NO 2
<211> LENGTH: 23
<212> TYPE: RNA
<213> ORGANISM: Artificial Sequence
<220> FEATURE:
<223> OTHER INFORMATION: Excluded EXO-code

<400> SEQUENCE: 2

uugacuagua caugaccacu uga                                              23


<210> SEQ ID NO 3
<211> LENGTH: 25
<212> TYPE: RNA
<213> ORGANISM: Artificial Sequence
<220> FEATURE:
<223> OTHER INFORMATION: Excluded EXO-code

<400> SEQUENCE: 3

acccugccgc cuggacuccg ccugu                                            25


<210> SEQ ID NO 4
<211> LENGTH: 20
<212> TYPE: RNA
<213> ORGANISM: Artificial Sequence
<220> FEATURE:
<223> OTHER INFORMATION: EXO-code

<400> SEQUENCE: 4

acaguagagc cuucaccggc                                                  20


<210> SEQ ID NO 5
<211> LENGTH: 44
<212> TYPE: DNA
<213> ORGANISM: Artificial Sequence
<220> FEATURE:
<223> OTHER INFORMATION: Primer

<400> SEQUENCE: 5

ttcaggtaat acgactcact atagggaaga gaaggacata tgat                       44


<210> SEQ ID NO 6
```

<211> LENGTH: 23
<212> TYPE: DNA
<213> ORGANISM: Artificial Sequence
<220> FEATURE:
<223> OTHER INFORMATION: Primer

<400> SEQUENCE: 6
tcaagtggtc atgtactagt caa 23

<210> SEQ ID NO 7
<211> LENGTH: 56
<212> TYPE: DNA
<213> ORGANISM: Artificial Sequence
<220> FEATURE:
<223> OTHER INFORMATION: Primer

<400> SEQUENCE: 7
tcgtcggcag cgtcagatgt gtataagaga cagtagggaa gagaaggaca tatgat 56

<210> SEQ ID NO 8
<211> LENGTH: 56
<212> TYPE: DNA
<213> ORGANISM: Artificial Sequence
<220> FEATURE:
<223> OTHER INFORMATION: Primer

<400> SEQUENCE: 8
gtctcgtggg ctcggagatg tgtataagag acagtcagtg gtcatgtact agtcaa 56

<210> SEQ ID NO 9
<211> LENGTH: 19
<212> TYPE: RNA
<213> ORGANISM: Artificial Sequence
<220> FEATURE:
<223> OTHER INFORMATION: EXO-code

<400> SEQUENCE: 9
ugugugcccc acagcagug 19

<210> SEQ ID NO 10
<211> LENGTH: 10
<212> TYPE: RNA
<213> ORGANISM: Artificial Sequence
<220> FEATURE:
<223> OTHER INFORMATION: EXO-code

<400> SEQUENCE: 10
cccacagcag 10

<210> SEQ ID NO 11
<211> LENGTH: 20
<212> TYPE: RNA
<213> ORGANISM: Artificial Sequence
<220> FEATURE:
<223> OTHER INFORMATION: EXO-code

<400> SEQUENCE: 11
ucguagguca ggaagcggcg 20

<210> SEQ ID NO 12
<211> LENGTH: 20
<212> TYPE: RNA
<213> ORGANISM: Artificial Sequence
<220> FEATURE:
<223> OTHER INFORMATION: EXO-code

<400> SEQUENCE: 12

```
gcgauaggcg gucguugguc                                                   20


<210> SEQ ID NO 13
<211> LENGTH: 20
<212> TYPE: RNA
<213> ORGANISM: Artificial Sequence
<220> FEATURE:
<223> OTHER INFORMATION: EXO-code

<400> SEQUENCE: 13

cccgcuucuu ccucgggugg                                                   20


<210> SEQ ID NO 14
<211> LENGTH: 20
<212> TYPE: RNA
<213> ORGANISM: Artificial Sequence
<220> FEATURE:
<223> OTHER INFORMATION: EXO-code

<400> SEQUENCE: 14

gucacucggc cuagugcguc                                                   20


<210> SEQ ID NO 15
<211> LENGTH: 20
<212> TYPE: RNA
<213> ORGANISM: Artificial Sequence
<220> FEATURE:
<223> OTHER INFORMATION: EXO-code

<400> SEQUENCE: 15

ccugaccuua cucggguggc                                                   20


<210> SEQ ID NO 16
<211> LENGTH: 20
<212> TYPE: RNA
<213> ORGANISM: Artificial Sequence
<220> FEATURE:
<223> OTHER INFORMATION: Exo-code

<400> SEQUENCE: 16

guggucgaua agcguacgcg                                                   20


<210> SEQ ID NO 17
<211> LENGTH: 20
<212> TYPE: RNA
<213> ORGANISM: Artificial Sequence
<220> FEATURE:
<223> OTHER INFORMATION: EXO-code

<400> SEQUENCE: 17

agggcguuug cucgcggguc                                                   20


<210> SEQ ID NO 18
<211> LENGTH: 20
<212> TYPE: RNA
<213> ORGANISM: Artificial Sequence
<220> FEATURE:
<223> OTHER INFORMATION: EXO-code

<400> SEQUENCE: 18

ccgggcguau cuuguggucg                                                   20


<210> SEQ ID NO 19
<211> LENGTH: 20
<212> TYPE: RNA
```

<213> ORGANISM: Artificial Sequence
<220> FEATURE:
<223> OTHER INFORMATION: EXO-code

<400> SEQUENCE: 19
cagacgguac ucaggugugc 20

<210> SEQ ID NO 20
<211> LENGTH: 20
<212> TYPE: RNA
<213> ORGANISM: Artificial Sequence
<220> FEATURE:
<223> OTHER INFORMATION: EXO-code

<400> SEQUENCE: 20
ggccuugguc gcgugcuggc 20

<210> SEQ ID NO 21
<211> LENGTH: 20
<212> TYPE: RNA
<213> ORGANISM: Artificial Sequence
<220> FEATURE:
<223> OTHER INFORMATION: EXO-code

<400> SEQUENCE: 21
uggaacgucg augugggccg 20

<210> SEQ ID NO 22
<211> LENGTH: 20
<212> TYPE: RNA
<213> ORGANISM: Artificial Sequence
<220> FEATURE:
<223> OTHER INFORMATION: EXO-code

<400> SEQUENCE: 22
gguucagggu gugggccgcc 20

<210> SEQ ID NO 23
<211> LENGTH: 20
<212> TYPE: RNA
<213> ORGANISM: Artificial Sequence
<220> FEATURE:
<223> OTHER INFORMATION: EXO-code

<400> SEQUENCE: 23
ucguagguca ggaagcggcg 20

<210> SEQ ID NO 24
<211> LENGTH: 20
<212> TYPE: RNA
<213> ORGANISM: Artificial Sequence
<220> FEATURE:
<223> OTHER INFORMATION: EXO-code

<400> SEQUENCE: 24
aaggccggug cuaguaguga 20

<210> SEQ ID NO 25
<211> LENGTH: 20
<212> TYPE: RNA
<213> ORGANISM: Artificial Sequence
<220> FEATURE:
<223> OTHER INFORMATION: EXO-code

<400> SEQUENCE: 25
gcgauaggcg gucguugguc 20

<210> SEQ ID NO 26
<211> LENGTH: 20
<212> TYPE: RNA
<213> ORGANISM: Artificial Sequence
<220> FEATURE:
<223> OTHER INFORMATION: EXO-code

<400> SEQUENCE: 26
gcuggucagg augcgggggc 20

<210> SEQ ID NO 27
<211> LENGTH: 20
<212> TYPE: RNA
<213> ORGANISM: Artificial Sequence
<220> FEATURE:
<223> OTHER INFORMATION: EXO-code

<400> SEQUENCE: 27
gcugcgaagu ggggcagguc 20

<210> SEQ ID NO 28
<211> LENGTH: 20
<212> TYPE: RNA
<213> ORGANISM: Artificial Sequence
<220> FEATURE:
<223> OTHER INFORMATION: EXO-code

<400> SEQUENCE: 28
ggucgaguga ugcggggcgc 20

<210> SEQ ID NO 29
<211> LENGTH: 20
<212> TYPE: RNA
<213> ORGANISM: Artificial Sequence
<220> FEATURE:
<223> OTHER INFORMATION: EXO-code

<400> SEQUENCE: 29
cguggcuggu ucgugcgggg 20

<210> SEQ ID NO 30
<211> LENGTH: 20
<212> TYPE: RNA
<213> ORGANISM: Artificial Sequence
<220> FEATURE:
<223> OTHER INFORMATION: EXO-code

<400> SEQUENCE: 30
gggcgaaauu ggcauggccg 20

<210> SEQ ID NO 31
<211> LENGTH: 20
<212> TYPE: RNA
<213> ORGANISM: Artificial Sequence
<220> FEATURE:
<223> OTHER INFORMATION: EXO-code

<400> SEQUENCE: 31
gaugguaagu uggaaagcga 20

<210> SEQ ID NO 32
<211> LENGTH: 20
<212> TYPE: RNA
<213> ORGANISM: Artificial Sequence
<220> FEATURE:

<223> OTHER INFORMATION: EXO-code

<400> SEQUENCE: 32
uggaacgucg augugggccg 20

<210> SEQ ID NO 33
<211> LENGTH: 20
<212> TYPE: RNA
<213> ORGANISM: Artificial Sequence
<220> FEATURE:
<223> OTHER INFORMATION: EXO-code

<400> SEQUENCE: 33
gaugguaugu uggaaagcga 20

<210> SEQ ID NO 34
<211> LENGTH: 20
<212> TYPE: RNA
<213> ORGANISM: Artificial Sequence
<220> FEATURE:
<223> OTHER INFORMATION: EXO-code

<400> SEQUENCE: 34
cguggcuggu ucgugcgggg 20

<210> SEQ ID NO 35
<211> LENGTH: 20
<212> TYPE: RNA
<213> ORGANISM: Artificial Sequence
<220> FEATURE:
<223> OTHER INFORMATION: EXO-code

<400> SEQUENCE: 35
uucguguauc uagugcaguc 20

<210> SEQ ID NO 36
<211> LENGTH: 20
<212> TYPE: RNA
<213> ORGANISM: Artificial Sequence
<220> FEATURE:
<223> OTHER INFORMATION: EXO-code

<400> SEQUENCE: 36
ggucgaguga ugcggggcgc 20

<210> SEQ ID NO 37
<211> LENGTH: 20
<212> TYPE: RNA
<213> ORGANISM: Artificial Sequence
<220> FEATURE:
<223> OTHER INFORMATION: EXO-code

<400> SEQUENCE: 37
uuucguguau ccuaguugcu 20

<210> SEQ ID NO 38
<211> LENGTH: 20
<212> TYPE: RNA
<213> ORGANISM: Artificial Sequence
<220> FEATURE:
<223> OTHER INFORMATION: EXO-code

<400> SEQUENCE: 38
ugauguauuu gguuugcaag 20

```
<210> SEQ ID NO 39
<211> LENGTH: 20
<212> TYPE: RNA
<213> ORGANISM: Artificial Sequence
<220> FEATURE:
<223> OTHER INFORMATION: EXO-code

<400> SEQUENCE: 39

uucguguucu gguugagugu                                                  20


<210> SEQ ID NO 40
<211> LENGTH: 20
<212> TYPE: RNA
<213> ORGANISM: Artificial Sequence
<220> FEATURE:
<223> OTHER INFORMATION: EXO-code

<400> SEQUENCE: 40

gcgcgggaag gguggcaugg                                                  20


<210> SEQ ID NO 41
<211> LENGTH: 20
<212> TYPE: RNA
<213> ORGANISM: Artificial Sequence
<220> FEATURE:
<223> OTHER INFORMATION: EXO-code

<400> SEQUENCE: 41

ugauguauug guaaguuucg                                                  20


<210> SEQ ID NO 42
<211> LENGTH: 20
<212> TYPE: RNA
<213> ORGANISM: Artificial Sequence
<220> FEATURE:
<223> OTHER INFORMATION: EXO-code

<400> SEQUENCE: 42

uauagaugug cuaguuugca                                                  20


<210> SEQ ID NO 43
<211> LENGTH: 20
<212> TYPE: RNA
<213> ORGANISM: Artificial Sequence
<220> FEATURE:
<223> OTHER INFORMATION: EXO-code

<400> SEQUENCE: 43

uuucguguuu agcguuugac                                                  20


<210> SEQ ID NO 44
<211> LENGTH: 20
<212> TYPE: RNA
<213> ORGANISM: Artificial Sequence
<220> FEATURE:
<223> OTHER INFORMATION: EXO-code

<400> SEQUENCE: 44

ugauguauuu gguuugcaag                                                  20


<210> SEQ ID NO 45
<211> LENGTH: 20
<212> TYPE: RNA
<213> ORGANISM: Artificial Sequence
<220> FEATURE:
<223> OTHER INFORMATION: EXO-code
```

```
<400> SEQUENCE: 45

acguguauua cuauugacua                                                   20


<210> SEQ ID NO 46
<211> LENGTH: 20
<212> TYPE: RNA
<213> ORGANISM: Artificial Sequence
<220> FEATURE:
<223> OTHER INFORMATION: EXO-code

<400> SEQUENCE: 46

gaggccugug cuaguaguga                                                   20


<210> SEQ ID NO 47
<211> LENGTH: 20
<212> TYPE: RNA
<213> ORGANISM: Artificial Sequence
<220> FEATURE:
<223> OTHER INFORMATION: EXO-code

<400> SEQUENCE: 47

uuagcguugu auuaguugca                                                   20


<210> SEQ ID NO 48
<211> LENGTH: 20
<212> TYPE: RNA
<213> ORGANISM: Artificial Sequence
<220> FEATURE:
<223> OTHER INFORMATION: EXO-code

<400> SEQUENCE: 48

ucauugugcu gaauugacua                                                   20


<210> SEQ ID NO 49
<211> LENGTH: 20
<212> TYPE: RNA
<213> ORGANISM: Artificial Sequence
<220> FEATURE:
<223> OTHER INFORMATION: EXO-code

<400> SEQUENCE: 49

aauuacacug ugcuaggaug                                                   20


<210> SEQ ID NO 50
<211> LENGTH: 20
<212> TYPE: RNA
<213> ORGANISM: Artificial Sequence
<220> FEATURE:
<223> OTHER INFORMATION: EXO-code

<400> SEQUENCE: 50

aucgauguau gagucauaua                                                   20


<210> SEQ ID NO 51
<211> LENGTH: 20
<212> TYPE: RNA
<213> ORGANISM: Artificial Sequence
<220> FEATURE:
<223> OTHER INFORMATION: Control

<400> SEQUENCE: 51

acaguagagc cuucaccggc                                                   20


<210> SEQ ID NO 52
<211> LENGTH: 20
```

<212> TYPE: RNA
<213> ORGANISM: Artificial Sequence
<220> FEATURE:
<223> OTHER INFORMATION: Control

<400> SEQUENCE: 52
gcucucggaa ggcuugggcu 20

<210> SEQ ID NO 53
<211> LENGTH: 20
<212> TYPE: RNA
<213> ORGANISM: Artificial Sequence
<220> FEATURE:
<223> OTHER INFORMATION: Control

<400> SEQUENCE: 53
agucggggua ugccuggaug 20

<210> SEQ ID NO 54
<211> LENGTH: 22
<212> TYPE: RNA
<213> ORGANISM: Artificial Sequence
<220> FEATURE:
<223> OTHER INFORMATION: Control

<400> SEQUENCE: 54
uggucuagga uuguuggagg ag 22

<210> SEQ ID NO 55
<211> LENGTH: 22
<212> TYPE: RNA
<213> ORGANISM: Artificial Sequence
<220> FEATURE:
<223> OTHER INFORMATION: Control

<400> SEQUENCE: 55
gguccagagg ggagauaggu uc 22

<210> SEQ ID NO 56
<211> LENGTH: 25
<212> TYPE: RNA
<213> ORGANISM: Artificial Sequence
<220> FEATURE:
<223> OTHER INFORMATION: Control

<400> SEQUENCE: 56
acccugccgc cuggacuccg ccugu 25

<210> SEQ ID NO 57
<211> LENGTH: 22
<212> TYPE: RNA
<213> ORGANISM: Caenorhabditis elegans

<400> SEQUENCE: 57
ucaccgggug uaaaucagcu ug 22

<210> SEQ ID NO 58
<211> LENGTH: 24
<212> TYPE: RNA
<213> ORGANISM: Caenorhabditis elegans

<400> SEQUENCE: 58
uacccguaau cuucauaauc cgag 24

<210> SEQ ID NO 59

<211> LENGTH: 20
<212> TYPE: RNA
<213> ORGANISM: Artificial Sequence
<220> FEATURE:
<223> OTHER INFORMATION: EXO-code

<400> SEQUENCE: 59
ucguagguca ggaagcggcg 20

<210> SEQ ID NO 60
<211> LENGTH: 20
<212> TYPE: RNA
<213> ORGANISM: Artificial Sequence
<220> FEATURE:
<223> OTHER INFORMATION: EXO-code

<400> SEQUENCE: 60
gcgauaggcg gucguugguc 20

<210> SEQ ID NO 61
<211> LENGTH: 27
<212> TYPE: RNA
<213> ORGANISM: Artificial Sequence
<220> FEATURE:
<223> OTHER INFORMATION: Control siRNA sense strand

<400> SEQUENCE: 61
ucacaaggga gagaaagaga ggaagga 27

<210> SEQ ID NO 62
<211> LENGTH: 19
<212> TYPE: RNA
<213> ORGANISM: Artificial Sequence
<220> FEATURE:
<223> OTHER INFORMATION: hnRNPM siRNA sense strand 1

<400> SEQUENCE: 62
gcauaggauu uggaauaaa 19

<210> SEQ ID NO 63
<211> LENGTH: 21
<212> TYPE: RNA
<213> ORGANISM: Artificial Sequence
<220> FEATURE:
<223> OTHER INFORMATION: hnRNPM siRNA sense strand 2

<400> SEQUENCE: 63
ggaauggaag gcauaggauu u 21

<210> SEQ ID NO 64
<211> LENGTH: 45
<212> TYPE: RNA
<213> ORGANISM: Artificial Sequence
<220> FEATURE:
<223> OTHER INFORMATION: EXO-code

<400> SEQUENCE: 64
guacauucua gauagccaug auuguguguc cccacagcac uguug 45

<210> SEQ ID NO 65
<211> LENGTH: 75
<212> TYPE: RNA
<213> ORGANISM: Artificial Sequence
<220> FEATURE:
<223> OTHER INFORMATION: EXO-code

<400> SEQUENCE: 65

```
ggcuaucuag aauguacaaa ggcaagagcu ggcauagcug uugaacuggg aacugcuaug     60

ccaacauauu gccau                                                      75


<210> SEQ ID NO 66
<211> LENGTH: 47
<212> TYPE: RNA
<213> ORGANISM: Artificial Sequence
<220> FEATURE:
<223> OTHER INFORMATION: EXO-code

<400> SEQUENCE: 66

gcuggucagg augcgggggc aaaguaacaa ucgaaagcca cgguuuu                   47


<210> SEQ ID NO 67
<211> LENGTH: 24
<212> TYPE: RNA
<213> ORGANISM: Artificial Sequence
<220> FEATURE:
<223> OTHER INFORMATION: Synthetic miR-132

<400> SEQUENCE: 67

aaccguggcu uucgauuguu acuu                                            24


<210> SEQ ID NO 68
<211> LENGTH: 27
<212> TYPE: RNA
<213> ORGANISM: Artificial Sequence
<220> FEATURE:
<223> OTHER INFORMATION: Snail siRNA

<400> SEQUENCE: 68

ccacagaaau ggccauggga aggccuc                                         27


<210> SEQ ID NO 69
<211> LENGTH: 27
<212> TYPE: RNA
<213> ORGANISM: Artificial Sequence
<220> FEATURE:
<223> OTHER INFORMATION: Slug siRNA

<400> SEQUENCE: 69

uccgaauaug caucuucagg gcgccca                                         27


<210> SEQ ID NO 70
<211> LENGTH: 27
<212> TYPE: RNA
<213> ORGANISM: Artificial Sequence
<220> FEATURE:
<223> OTHER INFORMATION: Negative control

<400> SEQUENCE: 70

ucacaaggga gagaaagaga ggaagga                                         27


<210> SEQ ID NO 71
<211> LENGTH: 20
<212> TYPE: RNA
<213> ORGANISM: Artificial Sequence
<220> FEATURE:
<223> OTHER INFORMATION: EXO-code

<400> SEQUENCE: 71

cguggcuggu ucgugcgggg                                                 20


<210> SEQ ID NO 72
```

<211> LENGTH: 20
<212> TYPE: RNA
<213> ORGANISM: Artificial Sequence
<220> FEATURE:
<223> OTHER INFORMATION: EXO-code

<400> SEQUENCE: 72
ggucgaguga ugcggggcgc 20

<210> SEQ ID NO 73
<211> LENGTH: 20
<212> TYPE: RNA
<213> ORGANISM: Artificial Sequence
<220> FEATURE:
<223> OTHER INFORMATION: EXO-code

<400> SEQUENCE: 73
ugauguauuu gguuugcaag 20

<210> SEQ ID NO 74
<211> LENGTH: 20
<212> TYPE: RNA
<213> ORGANISM: Artificial Sequence
<220> FEATURE:
<223> OTHER INFORMATION: EXO-code

<400> SEQUENCE: 74
uggaacgucg augugggccg 20

<210> SEQ ID NO 75
<211> LENGTH: 20
<212> TYPE: RNA
<213> ORGANISM: Artificial Sequence
<220> FEATURE:
<223> OTHER INFORMATION: EXO-code

<400> SEQUENCE: 75
gcgauaggcg gucguugguc 20

<210> SEQ ID NO 76
<211> LENGTH: 20
<212> TYPE: RNA
<213> ORGANISM: Artificial Sequence
<220> FEATURE:
<223> OTHER INFORMATION: EXO-code

<400> SEQUENCE: 76
ucguagguca ggaagcggcg 20

<210> SEQ ID NO 77
<211> LENGTH: 20
<212> TYPE: RNA
<213> ORGANISM: Artificial Sequence
<220> FEATURE:
<223> OTHER INFORMATION: EXO-code

<400> SEQUENCE: 77
gaaugaucuu gguugucaac 20

<210> SEQ ID NO 78
<211> LENGTH: 20
<212> TYPE: RNA
<213> ORGANISM: Artificial Sequence
<220> FEATURE:
<223> OTHER INFORMATION: EXO-code

<400> SEQUENCE: 78
uggaacgucg augugggccg 20

<210> SEQ ID NO 79
<211> LENGTH: 20
<212> TYPE: RNA
<213> ORGANISM: Artificial Sequence
<220> FEATURE:
<223> OTHER INFORMATION: EXO-code

<400> SEQUENCE: 79
agcgaggugg aguggcgugg 20

<210> SEQ ID NO 80
<211> LENGTH: 20
<212> TYPE: RNA
<213> ORGANISM: Artificial Sequence
<220> FEATURE:
<223> OTHER INFORMATION: EXO-code

<400> SEQUENCE: 80
cguggcuggu ucgugcgggg 20

<210> SEQ ID NO 81
<211> LENGTH: 20
<212> TYPE: RNA
<213> ORGANISM: Artificial Sequence
<220> FEATURE:
<223> OTHER INFORMATION: EXO-code

<400> SEQUENCE: 81
gcgcgggaag gguggcaugg 20

<210> SEQ ID NO 82
<211> LENGTH: 20
<212> TYPE: RNA
<213> ORGANISM: Artificial Sequence
<220> FEATURE:
<223> OTHER INFORMATION: EXO-code

<400> SEQUENCE: 82
gaugguaugu uggaaagcga 20

<210> SEQ ID NO 83
<211> LENGTH: 20
<212> TYPE: RNA
<213> ORGANISM: Artificial Sequence
<220> FEATURE:
<223> OTHER INFORMATION: EXO-code

<400> SEQUENCE: 83
ggucgaguga ugcggggcgc 20

<210> SEQ ID NO 84
<211> LENGTH: 20
<212> TYPE: RNA
<213> ORGANISM: Artificial Sequence
<220> FEATURE:
<223> OTHER INFORMATION: EXO-code

<400> SEQUENCE: 84
gaugguaagu uggaaagcga 20

<210> SEQ ID NO 85
<211> LENGTH: 20
<212> TYPE: RNA

<213> ORGANISM: Artificial Sequence
<220> FEATURE:
<223> OTHER INFORMATION: EXO-code

<400> SEQUENCE: 85
caguauuagc aagggagggg 20

<210> SEQ ID NO 86
<211> LENGTH: 20
<212> TYPE: RNA
<213> ORGANISM: Artificial Sequence
<220> FEATURE:
<223> OTHER INFORMATION: EXO-code

<400> SEQUENCE: 86
gagggggagg agggcaugcc 20

<210> SEQ ID NO 87
<211> LENGTH: 20
<212> TYPE: RNA
<213> ORGANISM: Artificial Sequence
<220> FEATURE:
<223> OTHER INFORMATION: EXO-code

<400> SEQUENCE: 87
uggaacgucg augugggccg 20

<210> SEQ ID NO 88
<211> LENGTH: 20
<212> TYPE: RNA
<213> ORGANISM: Artificial Sequence
<220> FEATURE:
<223> OTHER INFORMATION: EXO-code

<400> SEQUENCE: 88
ggucgaguga ugcggggcgc 20

<210> SEQ ID NO 89
<211> LENGTH: 20
<212> TYPE: RNA
<213> ORGANISM: Artificial Sequence
<220> FEATURE:
<223> OTHER INFORMATION: EXO-code

<400> SEQUENCE: 89
gaugguaagu uggaaagcga 20

<210> SEQ ID NO 90
<211> LENGTH: 20
<212> TYPE: RNA
<213> ORGANISM: Artificial Sequence
<220> FEATURE:
<223> OTHER INFORMATION: EXO-code

<400> SEQUENCE: 90
cguggcuggu ucgugcgggg 20

<210> SEQ ID NO 91
<211> LENGTH: 20
<212> TYPE: RNA
<213> ORGANISM: Artificial Sequence
<220> FEATURE:
<223> OTHER INFORMATION: EXO-code

<400> SEQUENCE: 91
gaugguaugu uggaaagcga 20

<210> SEQ ID NO 92
<211> LENGTH: 20
<212> TYPE: RNA
<213> ORGANISM: Artificial Sequence
<220> FEATURE:
<223> OTHER INFORMATION: EXO-code

<400> SEQUENCE: 92
gcuggucagg augcgggggc 20

<210> SEQ ID NO 93
<211> LENGTH: 20
<212> TYPE: RNA
<213> ORGANISM: Artificial Sequence
<220> FEATURE:
<223> OTHER INFORMATION: EXO-code

<400> SEQUENCE: 93
caaccuaggu gcggggcggg 20

<210> SEQ ID NO 94
<211> LENGTH: 20
<212> TYPE: RNA
<213> ORGANISM: Artificial Sequence
<220> FEATURE:
<223> OTHER INFORMATION: EXO-code

<400> SEQUENCE: 94
ggaagaucaa ggugcggggc 20

<210> SEQ ID NO 95
<211> LENGTH: 20
<212> TYPE: RNA
<213> ORGANISM: Artificial Sequence
<220> FEATURE:
<223> OTHER INFORMATION: EXO-code

<400> SEQUENCE: 95
gguucagggu gugggccgcc 20

<210> SEQ ID NO 96
<211> LENGTH: 20
<212> TYPE: RNA
<213> ORGANISM: Artificial Sequence
<220> FEATURE:
<223> OTHER INFORMATION: EXO-code

<400> SEQUENCE: 96
gcgcgggaag gguggcaugg 20

<210> SEQ ID NO 97
<211> LENGTH: 20
<212> TYPE: RNA
<213> ORGANISM: Artificial Sequence
<220> FEATURE:
<223> OTHER INFORMATION: EXO-code

<400> SEQUENCE: 97
gaugguaagu uggaaagcga 20

<210> SEQ ID NO 98
<211> LENGTH: 20
<212> TYPE: RNA
<213> ORGANISM: Artificial Sequence
<220> FEATURE:

<223> OTHER INFORMATION: EXO-code

<400> SEQUENCE: 98
uggaacgucg augugggccg 20

<210> SEQ ID NO 99
<211> LENGTH: 20
<212> TYPE: RNA
<213> ORGANISM: Artificial Sequence
<220> FEATURE:
<223> OTHER INFORMATION: EXO-code

<400> SEQUENCE: 99
gaugguaugu uggaaagcga 20

<210> SEQ ID NO 100
<211> LENGTH: 20
<212> TYPE: RNA
<213> ORGANISM: Artificial Sequence
<220> FEATURE:
<223> OTHER INFORMATION: EXO-code

<400> SEQUENCE: 100
cguggcuggu ucgugcgggg 20

<210> SEQ ID NO 101
<211> LENGTH: 20
<212> TYPE: RNA
<213> ORGANISM: Artificial Sequence
<220> FEATURE:
<223> OTHER INFORMATION: EXO-code

<400> SEQUENCE: 101
uucguguauc uagugcaguc 20

<210> SEQ ID NO 102
<211> LENGTH: 20
<212> TYPE: RNA
<213> ORGANISM: Artificial Sequence
<220> FEATURE:
<223> OTHER INFORMATION: EXO-code

<400> SEQUENCE: 102
ggucgaguga ugcggggcgc 20

<210> SEQ ID NO 103
<211> LENGTH: 20
<212> TYPE: RNA
<213> ORGANISM: Artificial Sequence
<220> FEATURE:
<223> OTHER INFORMATION: EXO-code

<400> SEQUENCE: 103
uuucguguau ccuaguugcu 20

<210> SEQ ID NO 104
<211> LENGTH: 20
<212> TYPE: RNA
<213> ORGANISM: Artificial Sequence
<220> FEATURE:
<223> OTHER INFORMATION: EXO-code

<400> SEQUENCE: 104
ugauguauuu gguuugcaag 20

<210> SEQ ID NO 105
<211> LENGTH: 20
<212> TYPE: RNA
<213> ORGANISM: Artificial Sequence
<220> FEATURE:
<223> OTHER INFORMATION: EXO-code

<400> SEQUENCE: 105
uucguguucu gguugagugu 20

<210> SEQ ID NO 106
<211> LENGTH: 20
<212> TYPE: RNA
<213> ORGANISM: Artificial Sequence
<220> FEATURE:
<223> OTHER INFORMATION: EXO-code

<400> SEQUENCE: 106
gcgcgggaag gguggcaugg 20

<210> SEQ ID NO 107
<211> LENGTH: 20
<212> TYPE: RNA
<213> ORGANISM: Artificial Sequence
<220> FEATURE:
<223> OTHER INFORMATION: EXO-code

<400> SEQUENCE: 107
gagucuuucc gucuugcgug 20

<210> SEQ ID NO 108
<211> LENGTH: 20
<212> TYPE: RNA
<213> ORGANISM: Artificial Sequence
<220> FEATURE:
<223> OTHER INFORMATION: EXO-code

<400> SEQUENCE: 108
agcgaguacg cugcgauugc 20

<210> SEQ ID NO 109
<211> LENGTH: 20
<212> TYPE: RNA
<213> ORGANISM: Artificial Sequence
<220> FEATURE:
<223> OTHER INFORMATION: EXO-code

<400> SEQUENCE: 109
gcgauguaug guuuucggug 20

<210> SEQ ID NO 110
<211> LENGTH: 20
<212> TYPE: RNA
<213> ORGANISM: Artificial Sequence
<220> FEATURE:
<223> OTHER INFORMATION: EXO-code

<400> SEQUENCE: 110
ccagagguga uggcggucgc 20

<210> SEQ ID NO 111
<211> LENGTH: 20
<212> TYPE: RNA
<213> ORGANISM: Artificial Sequence
<220> FEATURE:
<223> OTHER INFORMATION: EXO-code

<400> SEQUENCE: 111
ggcgaucgga aggcaugcac 20

<210> SEQ ID NO 112
<211> LENGTH: 20
<212> TYPE: RNA
<213> ORGANISM: Artificial Sequence
<220> FEATURE:
<223> OTHER INFORMATION: EXO-code

<400> SEQUENCE: 112
cacucgagau gccgcguagg 20

<210> SEQ ID NO 113
<211> LENGTH: 20
<212> TYPE: RNA
<213> ORGANISM: Artificial Sequence
<220> FEATURE:
<223> OTHER INFORMATION: EXO-code

<400> SEQUENCE: 113
cacgcaggcg agguggcagc 20

<210> SEQ ID NO 114
<211> LENGTH: 20
<212> TYPE: RNA
<213> ORGANISM: Artificial Sequence
<220> FEATURE:
<223> OTHER INFORMATION: EXO-code

<400> SEQUENCE: 114
ccuuuguguc ugcaggcucu 20

<210> SEQ ID NO 115
<211> LENGTH: 20
<212> TYPE: RNA
<213> ORGANISM: Artificial Sequence
<220> FEATURE:
<223> OTHER INFORMATION: EXO-code

<400> SEQUENCE: 115
ccgggcguau cuuguggucg 20

<210> SEQ ID NO 116
<211> LENGTH: 20
<212> TYPE: RNA
<213> ORGANISM: Artificial Sequence
<220> FEATURE:
<223> OTHER INFORMATION: EXO-code

<400> SEQUENCE: 116
caucugcucu cgggggcaca 20

<210> SEQ ID NO 117
<211> LENGTH: 20
<212> TYPE: RNA
<213> ORGANISM: Artificial Sequence
<220> FEATURE:
<223> OTHER INFORMATION: EXO-code

<400> SEQUENCE: 117
ucguagguca ggaagcggcg 20

<210> SEQ ID NO 118
<211> LENGTH: 20

<212> TYPE: RNA
<213> ORGANISM: Artificial Sequence
<220> FEATURE:
<223> OTHER INFORMATION: EXO-code

<400> SEQUENCE: 118
ccgggcguau cuuguggucg 20

<210> SEQ ID NO 119
<211> LENGTH: 20
<212> TYPE: RNA
<213> ORGANISM: Artificial Sequence
<220> FEATURE:
<223> OTHER INFORMATION: EXO-code

<400> SEQUENCE: 119
guggucgaua agcguacgcg 20

<210> SEQ ID NO 120
<211> LENGTH: 20
<212> TYPE: RNA
<213> ORGANISM: Artificial Sequence
<220> FEATURE:
<223> OTHER INFORMATION: EXO-code

<400> SEQUENCE: 120
ugcgacgucg uuagugguac 20

<210> SEQ ID NO 121
<211> LENGTH: 20
<212> TYPE: RNA
<213> ORGANISM: Artificial Sequence
<220> FEATURE:
<223> OTHER INFORMATION: EXO-code

<400> SEQUENCE: 121
ggccuugguc gcgugcuggc 20

<210> SEQ ID NO 122
<211> LENGTH: 20
<212> TYPE: RNA
<213> ORGANISM: Artificial Sequence
<220> FEATURE:
<223> OTHER INFORMATION: EXO-code

<400> SEQUENCE: 122
ccagagguga uggcggucgc 20

<210> SEQ ID NO 123
<211> LENGTH: 20
<212> TYPE: RNA
<213> ORGANISM: Artificial Sequence
<220> FEATURE:
<223> OTHER INFORMATION: EXO-code

<400> SEQUENCE: 123
ccgcgugguu ugugcgggug 20

<210> SEQ ID NO 124
<211> LENGTH: 20
<212> TYPE: RNA
<213> ORGANISM: Artificial Sequence
<220> FEATURE:
<223> OTHER INFORMATION: EXO-code

<400> SEQUENCE: 124
ccagaacuug ugguaccugc 20

<210> SEQ ID NO 125
<211> LENGTH: 20
<212> TYPE: RNA
<213> ORGANISM: Artificial Sequence
<220> FEATURE:
<223> OTHER INFORMATION: EXO-code

<400> SEQUENCE: 125
gcgauguaug guuuucggug 20

<210> SEQ ID NO 126
<211> LENGTH: 20
<212> TYPE: RNA
<213> ORGANISM: Artificial Sequence
<220> FEATURE:
<223> OTHER INFORMATION: EXO-code

<400> SEQUENCE: 126
caucugcucu cgggggcaca 20

<210> SEQ ID NO 127
<211> LENGTH: 20
<212> TYPE: RNA
<213> ORGANISM: Artificial Sequence
<220> FEATURE:
<223> OTHER INFORMATION: EXO-code

<400> SEQUENCE: 127
ucguagguca ggaagcggcg 20

<210> SEQ ID NO 128
<211> LENGTH: 20
<212> TYPE: RNA
<213> ORGANISM: Artificial Sequence
<220> FEATURE:
<223> OTHER INFORMATION: EXO-code

<400> SEQUENCE: 128
gcgauaggcg gucguugguc 20

<210> SEQ ID NO 129
<211> LENGTH: 20
<212> TYPE: RNA
<213> ORGANISM: Artificial Sequence
<220> FEATURE:
<223> OTHER INFORMATION: EXO-code

<400> SEQUENCE: 129
cccgcuucuu ccucgggugg 20

<210> SEQ ID NO 130
<211> LENGTH: 20
<212> TYPE: RNA
<213> ORGANISM: Artificial Sequence
<220> FEATURE:
<223> OTHER INFORMATION: EXO-code

<400> SEQUENCE: 130
gucacucggc cuagugcguc 20

<210> SEQ ID NO 131
<211> LENGTH: 20
<212> TYPE: RNA
<213> ORGANISM: Artificial Sequence
<220> FEATURE:
<223> OTHER INFORMATION: EXO-code

<400> SEQUENCE: 131
ccugaccuua cucggguggc 20

<210> SEQ ID NO 132
<211> LENGTH: 20
<212> TYPE: RNA
<213> ORGANISM: Artificial Sequence
<220> FEATURE:
<223> OTHER INFORMATION: EXO-code

<400> SEQUENCE: 132
guggucgaua agcguacgcg 20

<210> SEQ ID NO 133
<211> LENGTH: 20
<212> TYPE: RNA
<213> ORGANISM: Artificial Sequence
<220> FEATURE:
<223> OTHER INFORMATION: EXO-code

<400> SEQUENCE: 133
agggcguuug cucgcggguc 20

<210> SEQ ID NO 134
<211> LENGTH: 20
<212> TYPE: RNA
<213> ORGANISM: Artificial Sequence
<220> FEATURE:
<223> OTHER INFORMATION: EXO-code

<400> SEQUENCE: 134
ccgggcguau cuuguggucg 20

<210> SEQ ID NO 135
<211> LENGTH: 20
<212> TYPE: RNA
<213> ORGANISM: Artificial Sequence
<220> FEATURE:
<223> OTHER INFORMATION: EXO-code

<400> SEQUENCE: 135
cagacgguac ucaggugugc 20

<210> SEQ ID NO 136
<211> LENGTH: 20
<212> TYPE: RNA
<213> ORGANISM: Artificial Sequence
<220> FEATURE:
<223> OTHER INFORMATION: EXO-code

<400> SEQUENCE: 136
ggccuugguc gcgugcuggc 20

<210> SEQ ID NO 137
<211> LENGTH: 20
<212> TYPE: RNA
<213> ORGANISM: Artificial Sequence
<220> FEATURE:
<223> OTHER INFORMATION: EXO-code

<400> SEQUENCE: 137
gucggugaac gacugguggc 20

<210> SEQ ID NO 138
<211> LENGTH: 20
<212> TYPE: RNA
<213> ORGANISM: Artificial Sequence
<220> FEATURE:
<223> OTHER INFORMATION: EXO-code

<400> SEQUENCE: 138
gguuaauuuu augugucaac 20

<210> SEQ ID NO 139
<211> LENGTH: 20
<212> TYPE: RNA
<213> ORGANISM: Artificial Sequence
<220> FEATURE:
<223> OTHER INFORMATION: EXO-code

<400> SEQUENCE: 139
gggcuuucgg caggcggucg 20

<210> SEQ ID NO 140
<211> LENGTH: 20
<212> TYPE: RNA
<213> ORGANISM: Artificial Sequence
<220> FEATURE:
<223> OTHER INFORMATION: EXO-code

<400> SEQUENCE: 140
guggauguag ggggacgggc 20

<210> SEQ ID NO 141
<211> LENGTH: 20
<212> TYPE: RNA
<213> ORGANISM: Artificial Sequence
<220> FEATURE:
<223> OTHER INFORMATION: EXO-code

<400> SEQUENCE: 141
ugcgauguug ugaguggccc 20

<210> SEQ ID NO 142
<211> LENGTH: 20
<212> TYPE: RNA
<213> ORGANISM: Artificial Sequence
<220> FEATURE:
<223> OTHER INFORMATION: EXO-code

<400> SEQUENCE: 142
gcauaugggc gcuugugugg 20

<210> SEQ ID NO 143
<211> LENGTH: 20
<212> TYPE: RNA
<213> ORGANISM: Artificial Sequence
<220> FEATURE:
<223> OTHER INFORMATION: EXO-code

<400> SEQUENCE: 143
gggugcggaa gucagugugg 20

<210> SEQ ID NO 144
<211> LENGTH: 20
<212> TYPE: RNA
<213> ORGANISM: Artificial Sequence
<220> FEATURE:
<223> OTHER INFORMATION: EXO-code

<400> SEQUENCE: 144
gagcugcaug uggcguuggg 20

<210> SEQ ID NO 145
<211> LENGTH: 20
<212> TYPE: RNA
<213> ORGANISM: Artificial Sequence
<220> FEATURE:
<223> OTHER INFORMATION: EXO-code

<400> SEQUENCE: 145
gugguaaggu uggaaggugu 20

<210> SEQ ID NO 146
<211> LENGTH: 20
<212> TYPE: RNA
<213> ORGANISM: Artificial Sequence
<220> FEATURE:
<223> OTHER INFORMATION: EXO-code

<400> SEQUENCE: 146
gggccuugau cacguggugc 20

<210> SEQ ID NO 147
<211> LENGTH: 20
<212> TYPE: RNA
<213> ORGANISM: Artificial Sequence
<220> FEATURE:
<223> OTHER INFORMATION: EXO-code

<400> SEQUENCE: 147
gaggccugug cuaguaguga 20

<210> SEQ ID NO 148
<211> LENGTH: 20
<212> TYPE: RNA
<213> ORGANISM: Artificial Sequence
<220> FEATURE:
<223> OTHER INFORMATION: EXO-code

<400> SEQUENCE: 148
ugguagguug gaaggucggg 20

<210> SEQ ID NO 149
<211> LENGTH: 20
<212> TYPE: RNA
<213> ORGANISM: Artificial Sequence
<220> FEATURE:
<223> OTHER INFORMATION: EXO-code

<400> SEQUENCE: 149
cgugguaugg uuggaacggu 20

<210> SEQ ID NO 150
<211> LENGTH: 20
<212> TYPE: RNA
<213> ORGANISM: Artificial Sequence
<220> FEATURE:
<223> OTHER INFORMATION: EXO-code

<400> SEQUENCE: 150
aaggguaagu uggaaagucg 20

<210> SEQ ID NO 151

<211> LENGTH: 20
<212> TYPE: RNA
<213> ORGANISM: Artificial Sequence
<220> FEATURE:
<223> OTHER INFORMATION: EXO-code

<400> SEQUENCE: 151
gugguagguu ggaaggccgg 20

<210> SEQ ID NO 152
<211> LENGTH: 20
<212> TYPE: RNA
<213> ORGANISM: Artificial Sequence
<220> FEATURE:
<223> OTHER INFORMATION: EXO-code

<400> SEQUENCE: 152
gugguagguu ggaaaggcug 20

<210> SEQ ID NO 153
<211> LENGTH: 20
<212> TYPE: RNA
<213> ORGANISM: Artificial Sequence
<220> FEATURE:
<223> OTHER INFORMATION: EXO-code

<400> SEQUENCE: 153
ggugguaugu uggaagguug 20

<210> SEQ ID NO 154
<211> LENGTH: 20
<212> TYPE: RNA
<213> ORGANISM: Artificial Sequence
<220> FEATURE:
<223> OTHER INFORMATION: EXO-code

<400> SEQUENCE: 154
ugcgauguug ugaguggccc 20

<210> SEQ ID NO 155
<211> LENGTH: 20
<212> TYPE: RNA
<213> ORGANISM: Artificial Sequence
<220> FEATURE:
<223> OTHER INFORMATION: EXO-code

<400> SEQUENCE: 155
agugguaagu uggaaugcac 20

<210> SEQ ID NO 156
<211> LENGTH: 20
<212> TYPE: RNA
<213> ORGANISM: Artificial Sequence
<220> FEATURE:
<223> OTHER INFORMATION: EXO-code

<400> SEQUENCE: 156
gggccuugau cacguggugc 20

<210> SEQ ID NO 157
<211> LENGTH: 20
<212> TYPE: RNA
<213> ORGANISM: Artificial Sequence
<220> FEATURE:
<223> OTHER INFORMATION: EXO-code

<400> SEQUENCE: 157
aaggccggug cuaguaguga 20

<210> SEQ ID NO 158
<211> LENGTH: 20
<212> TYPE: RNA
<213> ORGANISM: Artificial Sequence
<220> FEATURE:
<223> OTHER INFORMATION: EXO-code

<400> SEQUENCE: 158
gugguagguu ggaucgucgg 20

<210> SEQ ID NO 159
<211> LENGTH: 20
<212> TYPE: RNA
<213> ORGANISM: Artificial Sequence
<220> FEATURE:
<223> OTHER INFORMATION: EXO-code

<400> SEQUENCE: 159
ugugguaucg uuggaaagcg 20

<210> SEQ ID NO 160
<211> LENGTH: 20
<212> TYPE: RNA
<213> ORGANISM: Artificial Sequence
<220> FEATURE:
<223> OTHER INFORMATION: EXO-code

<400> SEQUENCE: 160
ggugguaggu uggaacggcg 20

<210> SEQ ID NO 161
<211> LENGTH: 20
<212> TYPE: RNA
<213> ORGANISM: Artificial Sequence
<220> FEATURE:
<223> OTHER INFORMATION: EXO-code

<400> SEQUENCE: 161
agguaugggc gcuucguggc 20

<210> SEQ ID NO 162
<211> LENGTH: 20
<212> TYPE: RNA
<213> ORGANISM: Artificial Sequence
<220> FEATURE:
<223> OTHER INFORMATION: EXO-code

<400> SEQUENCE: 162
gucgugguau guuggagggc 20

<210> SEQ ID NO 163
<211> LENGTH: 20
<212> TYPE: RNA
<213> ORGANISM: Artificial Sequence
<220> FEATURE:
<223> OTHER INFORMATION: EXO-code

<400> SEQUENCE: 163
gggguauugu uggaacggcg 20

<210> SEQ ID NO 164
<211> LENGTH: 20
<212> TYPE: RNA

<213> ORGANISM: Artificial Sequence
<220> FEATURE:
<223> OTHER INFORMATION: EXO-code

<400> SEQUENCE: 164
cggguauagu uggaacgucg 20

<210> SEQ ID NO 165
<211> LENGTH: 20
<212> TYPE: RNA
<213> ORGANISM: Artificial Sequence
<220> FEATURE:
<223> OTHER INFORMATION: EXO-code

<400> SEQUENCE: 165
gugguagguu ggaaaggcug 20

<210> SEQ ID NO 166
<211> LENGTH: 20
<212> TYPE: RNA
<213> ORGANISM: Artificial Sequence
<220> FEATURE:
<223> OTHER INFORMATION: EXO-code

<400> SEQUENCE: 166
gugguauggu uggaacgcag 20

<210> SEQ ID NO 167
<211> LENGTH: 20
<212> TYPE: RNA
<213> ORGANISM: Artificial Sequence
<220> FEATURE:
<223> OTHER INFORMATION: EXO-code

<400> SEQUENCE: 167
uggaacgucg augugggccg 20

<210> SEQ ID NO 168
<211> LENGTH: 20
<212> TYPE: RNA
<213> ORGANISM: Artificial Sequence
<220> FEATURE:
<223> OTHER INFORMATION: EXO-code

<400> SEQUENCE: 168
gguucagggu gugggccgcc 20

<210> SEQ ID NO 169
<211> LENGTH: 20
<212> TYPE: RNA
<213> ORGANISM: Artificial Sequence
<220> FEATURE:
<223> OTHER INFORMATION: EXO-code

<400> SEQUENCE: 169
gcuggucagg augcgggggc 20

<210> SEQ ID NO 170
<211> LENGTH: 20
<212> TYPE: RNA
<213> ORGANISM: Artificial Sequence
<220> FEATURE:
<223> OTHER INFORMATION: EXO-code

<400> SEQUENCE: 170
cguggcuggu ucgugcgggg 20

<210> SEQ ID NO 171
<211> LENGTH: 20
<212> TYPE: RNA
<213> ORGANISM: Artificial Sequence
<220> FEATURE:
<223> OTHER INFORMATION: EXO-code

<400> SEQUENCE: 171
ggucgaguga ugcggggcgc 20

<210> SEQ ID NO 172
<211> LENGTH: 20
<212> TYPE: RNA
<213> ORGANISM: Artificial Sequence
<220> FEATURE:
<223> OTHER INFORMATION: EXO-code

<400> SEQUENCE: 172
cuagcgacgg ugcgggggug 20

<210> SEQ ID NO 173
<211> LENGTH: 20
<212> TYPE: RNA
<213> ORGANISM: Artificial Sequence
<220> FEATURE:
<223> OTHER INFORMATION: EXO-code

<400> SEQUENCE: 173
uggggauaag uauguugcgg 20

<210> SEQ ID NO 174
<211> LENGTH: 20
<212> TYPE: RNA
<213> ORGANISM: Artificial Sequence
<220> FEATURE:
<223> OTHER INFORMATION: EXO-code

<400> SEQUENCE: 174
ucguagguca ggaagcggcg 20

<210> SEQ ID NO 175
<211> LENGTH: 20
<212> TYPE: RNA
<213> ORGANISM: Artificial Sequence
<220> FEATURE:
<223> OTHER INFORMATION: EXO-code

<400> SEQUENCE: 175
ugcgauguug ugaguggccc 20

<210> SEQ ID NO 176
<211> LENGTH: 20
<212> TYPE: RNA
<213> ORGANISM: Artificial Sequence
<220> FEATURE:
<223> OTHER INFORMATION: EXO-code

<400> SEQUENCE: 176
gcgcgggaag gguggcaugg 20

<210> SEQ ID NO 177
<211> LENGTH: 20
<212> TYPE: RNA
<213> ORGANISM: Artificial Sequence
<220> FEATURE:

<223> OTHER INFORMATION: EXO-code

<400> SEQUENCE: 177
uggaacgucg augugggccg 20

<210> SEQ ID NO 178
<211> LENGTH: 20
<212> TYPE: RNA
<213> ORGANISM: Artificial Sequence
<220> FEATURE:
<223> OTHER INFORMATION: EXO-code

<400> SEQUENCE: 178
gguucagggu gugggccgcc 20

<210> SEQ ID NO 179
<211> LENGTH: 20
<212> TYPE: RNA
<213> ORGANISM: Artificial Sequence
<220> FEATURE:
<223> OTHER INFORMATION: EXO-code

<400> SEQUENCE: 179
ucguagguca ggaagcggcg 20

<210> SEQ ID NO 180
<211> LENGTH: 20
<212> TYPE: RNA
<213> ORGANISM: Artificial Sequence
<220> FEATURE:
<223> OTHER INFORMATION: EXO-code

<400> SEQUENCE: 180
aaggccggug cuaguaguga 20

<210> SEQ ID NO 181
<211> LENGTH: 20
<212> TYPE: RNA
<213> ORGANISM: Artificial Sequence
<220> FEATURE:
<223> OTHER INFORMATION: EXO-code

<400> SEQUENCE: 181
gcgauaggcg gucguugguc 20

<210> SEQ ID NO 182
<211> LENGTH: 20
<212> TYPE: RNA
<213> ORGANISM: Artificial Sequence
<220> FEATURE:
<223> OTHER INFORMATION: EXO-code

<400> SEQUENCE: 182
gcuggucagg augcgggggc 20

<210> SEQ ID NO 183
<211> LENGTH: 20
<212> TYPE: RNA
<213> ORGANISM: Artificial Sequence
<220> FEATURE:
<223> OTHER INFORMATION: EXO-code

<400> SEQUENCE: 183
gcugcgaagu ggggcagguc 20

<210> SEQ ID NO 184
<211> LENGTH: 20
<212> TYPE: RNA
<213> ORGANISM: Artificial Sequence
<220> FEATURE:
<223> OTHER INFORMATION: EXO-code

<400> SEQUENCE: 184
ggucgaguga ugcggggcgc 20

<210> SEQ ID NO 185
<211> LENGTH: 20
<212> TYPE: RNA
<213> ORGANISM: Artificial Sequence
<220> FEATURE:
<223> OTHER INFORMATION: EXO-code

<400> SEQUENCE: 185
cguggcuggu ucgugcgggg 20

<210> SEQ ID NO 186
<211> LENGTH: 20
<212> TYPE: RNA
<213> ORGANISM: Artificial Sequence
<220> FEATURE:
<223> OTHER INFORMATION: EXO-code

<400> SEQUENCE: 186
gggcgaaauu ggcauggccg 20

<210> SEQ ID NO 187
<211> LENGTH: 20
<212> TYPE: RNA
<213> ORGANISM: Artificial Sequence
<220> FEATURE:
<223> OTHER INFORMATION: EXO-code

<400> SEQUENCE: 187
aaggccggug cuaguaguga 20

<210> SEQ ID NO 188
<211> LENGTH: 20
<212> TYPE: RNA
<213> ORGANISM: Artificial Sequence
<220> FEATURE:
<223> OTHER INFORMATION: EXO-code

<400> SEQUENCE: 188
ugauguauug guaaguuucg 20

<210> SEQ ID NO 189
<211> LENGTH: 20
<212> TYPE: RNA
<213> ORGANISM: Artificial Sequence
<220> FEATURE:
<223> OTHER INFORMATION: EXO-code

<400> SEQUENCE: 189
uauagaugug cuaguuugca 20

<210> SEQ ID NO 190
<211> LENGTH: 20
<212> TYPE: RNA
<213> ORGANISM: Artificial Sequence
<220> FEATURE:
<223> OTHER INFORMATION: EXO-code

<400> SEQUENCE: 190
uuagcguugu auuaguugca 20

<210> SEQ ID NO 191
<211> LENGTH: 20
<212> TYPE: RNA
<213> ORGANISM: Artificial Sequence
<220> FEATURE:
<223> OTHER INFORMATION: EXO-code

<400> SEQUENCE: 191
aucgauguau gagucauaua 20

<210> SEQ ID NO 192
<211> LENGTH: 20
<212> TYPE: RNA
<213> ORGANISM: Artificial Sequence
<220> FEATURE:
<223> OTHER INFORMATION: EXO-code

<400> SEQUENCE: 192
aauuacacug ugcuaggaug 20

<210> SEQ ID NO 193
<211> LENGTH: 20
<212> TYPE: RNA
<213> ORGANISM: Artificial Sequence
<220> FEATURE:
<223> OTHER INFORMATION: EXO-code

<400> SEQUENCE: 193
uugaagugua cauugucgua 20

<210> SEQ ID NO 194
<211> LENGTH: 20
<212> TYPE: RNA
<213> ORGANISM: Artificial Sequence
<220> FEATURE:
<223> OTHER INFORMATION: EXO-code

<400> SEQUENCE: 194
ugauguguua guuugaaugu 20

<210> SEQ ID NO 195
<211> LENGTH: 20
<212> TYPE: RNA
<213> ORGANISM: Artificial Sequence
<220> FEATURE:
<223> OTHER INFORMATION: EXO-code

<400> SEQUENCE: 195
ugaaaugaga cugguuuugc 20

<210> SEQ ID NO 196
<211> LENGTH: 20
<212> TYPE: RNA
<213> ORGANISM: Artificial Sequence
<220> FEATURE:
<223> OTHER INFORMATION: EXO-code

<400> SEQUENCE: 196
ugauguauuu gguuugcaag 20

<210> SEQ ID NO 197
<211> LENGTH: 20

<212> TYPE: RNA
<213> ORGANISM: Artificial Sequence
<220> FEATURE:
<223> OTHER INFORMATION: EXO-code

<400> SEQUENCE: 197
ugauguauug guaaguuucg 20

<210> SEQ ID NO 198
<211> LENGTH: 20
<212> TYPE: RNA
<213> ORGANISM: Artificial Sequence
<220> FEATURE:
<223> OTHER INFORMATION: EXO-code

<400> SEQUENCE: 198
uauagaugug cuaguuugca 20

<210> SEQ ID NO 199
<211> LENGTH: 20
<212> TYPE: RNA
<213> ORGANISM: Artificial Sequence
<220> FEATURE:
<223> OTHER INFORMATION: EXO-code

<400> SEQUENCE: 199
uuucguguuu agcguuugac 20

<210> SEQ ID NO 200
<211> LENGTH: 20
<212> TYPE: RNA
<213> ORGANISM: Artificial Sequence
<220> FEATURE:
<223> OTHER INFORMATION: EXO-code

<400> SEQUENCE: 200
ugauguauuu gguuugcaag 20

<210> SEQ ID NO 201
<211> LENGTH: 20
<212> TYPE: RNA
<213> ORGANISM: Artificial Sequence
<220> FEATURE:
<223> OTHER INFORMATION: EXO-code

<400> SEQUENCE: 201
acguguauua cuauugacua 20

<210> SEQ ID NO 202
<211> LENGTH: 20
<212> TYPE: RNA
<213> ORGANISM: Artificial Sequence
<220> FEATURE:
<223> OTHER INFORMATION: EXO-code

<400> SEQUENCE: 202
gaggccugug cuaguaguga 20

<210> SEQ ID NO 203
<211> LENGTH: 20
<212> TYPE: RNA
<213> ORGANISM: Artificial Sequence
<220> FEATURE:
<223> OTHER INFORMATION: EXO-code

<400> SEQUENCE: 203
uuagcguugu auuaguugca 20

<210> SEQ ID NO 204
<211> LENGTH: 20
<212> TYPE: RNA
<213> ORGANISM: Artificial Sequence
<220> FEATURE:
<223> OTHER INFORMATION: EXO-code

<400> SEQUENCE: 204
ucauugugcu gaauugacua 20

<210> SEQ ID NO 205
<211> LENGTH: 20
<212> TYPE: RNA
<213> ORGANISM: Artificial Sequence
<220> FEATURE:
<223> OTHER INFORMATION: EXO-code

<400> SEQUENCE: 205
aauuacacug ugcuaggaug 20

<210> SEQ ID NO 206
<211> LENGTH: 20
<212> TYPE: RNA
<213> ORGANISM: Artificial Sequence
<220> FEATURE:
<223> OTHER INFORMATION: EXO-code

<400> SEQUENCE: 206
aucgauguau gagucauaua 20

<210> SEQ ID NO 207
<211> LENGTH: 11
<212> TYPE: RNA
<213> ORGANISM: Artificial Sequence
<220> FEATURE:
<223> OTHER INFORMATION: EXO-code

<400> SEQUENCE: 207
aucuuguggu c 11

<210> SEQ ID NO 208
<211> LENGTH: 10
<212> TYPE: RNA
<213> ORGANISM: Artificial Sequence
<220> FEATURE:
<223> OTHER INFORMATION: EXO-code

<400> SEQUENCE: 208
aaguggcgug 10

<210> SEQ ID NO 209
<211> LENGTH: 10
<212> TYPE: RNA
<213> ORGANISM: Artificial Sequence
<220> FEATURE:
<223> OTHER INFORMATION: EXO-code

<400> SEQUENCE: 209
augcgggggc 10

<210> SEQ ID NO 210
<211> LENGTH: 21
<212> TYPE: RNA
<213> ORGANISM: Artificial Sequence

```
<220> FEATURE:
<223> OTHER INFORMATION: SNAIL siRNA anti-sense

<400> SEQUENCE: 210

guggcuucgg augugcaucu u                                              21


<210> SEQ ID NO 211
<211> LENGTH: 21
<212> TYPE: RNA
<213> ORGANISM: Artificial Sequence
<220> FEATURE:
<223> OTHER INFORMATION: SNAIL siRNA sense

<400> SEQUENCE: 211

gaugcacauc cgaagccacu u                                              21


<210> SEQ ID NO 212
<211> LENGTH: 20
<212> TYPE: RNA
<213> ORGANISM: Artificial Sequence
<220> FEATURE:
<223> OTHER INFORMATION: EXO-code

<400> SEQUENCE: 212

gcuggucagg augcgggggc                                                20


<210> SEQ ID NO 213
<211> LENGTH: 20
<212> TYPE: DNA
<213> ORGANISM: Artificial Sequence
<220> FEATURE:
<223> OTHER INFORMATION: Primer

<400> SEQUENCE: 213

cctgtcccct cagttcatgt                                                20


<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214

cccatggtct tcttctgcat                                                20


<210> SEQ ID NO 215
<211> LENGTH: 20
<212> TYPE: RNA
<213> ORGANISM: Artificial Sequence
<220> FEATURE:
<223> OTHER INFORMATION: EXO-code

<400> SEQUENCE: 215

ugugugaccc cacagcagug                                                20


<210> SEQ ID NO 216
<211> LENGTH: 20
<212> TYPE: DNA
<213> ORGANISM: Artificial Sequence
<220> FEATURE:
<223> OTHER INFORMATION: EXO-code

<400> SEQUENCE: 216

tcgtaggtca ggaagcggcg                                                20
```

<210> SEQ ID NO 217
<211> LENGTH: 20
<212> TYPE: DNA
<213> ORGANISM: Artificial Sequence
<220> FEATURE:
<223> OTHER INFORMATION: EXO-code

<400> SEQUENCE: 217
gcgataggcg gtcgttggtc 20

<210> SEQ ID NO 218
<211> LENGTH: 20
<212> TYPE: DNA
<213> ORGANISM: Artificial Sequence
<220> FEATURE:
<223> OTHER INFORMATION: EXO-code

<400> SEQUENCE: 218
cccgcttctt cctcgggtgg 20

<210> SEQ ID NO 219
<211> LENGTH: 20
<212> TYPE: DNA
<213> ORGANISM: Artificial Sequence
<220> FEATURE:
<223> OTHER INFORMATION: EXO-code

<400> SEQUENCE: 219
gtcactcggc ctagtgcgtc 20

<210> SEQ ID NO 220
<211> LENGTH: 20
<212> TYPE: DNA
<213> ORGANISM: Artificial Sequence
<220> FEATURE:
<223> OTHER INFORMATION: EXO-code

<400> SEQUENCE: 220
cctgacctta ctcgggtggc 20

<210> SEQ ID NO 221
<211> LENGTH: 20
<212> TYPE: DNA
<213> ORGANISM: Artificial Sequence
<220> FEATURE:
<223> OTHER INFORMATION: EXO-code

<400> SEQUENCE: 221
gtggtcgata agcgtacgcg 20

<210> SEQ ID NO 222
<211> LENGTH: 20
<212> TYPE: DNA
<213> ORGANISM: Artificial Sequence
<220> FEATURE:
<223> OTHER INFORMATION: EXO-code

<400> SEQUENCE: 222
agggcgtttg ctcgcgggtc 20

<210> SEQ ID NO 223
<211> LENGTH: 20
<212> TYPE: DNA
<213> ORGANISM: Artificial Sequence
<220> FEATURE:
<223> OTHER INFORMATION: EXO-code

<400> SEQUENCE: 223
ccgggcgtat cttgtggtcg 20

<210> SEQ ID NO 224
<211> LENGTH: 20
<212> TYPE: DNA
<213> ORGANISM: Artificial Sequence
<220> FEATURE:
<223> OTHER INFORMATION: EXO-code

<400> SEQUENCE: 224
cagacggtac tcaggtgtgc 20

<210> SEQ ID NO 225
<211> LENGTH: 20
<212> TYPE: DNA
<213> ORGANISM: Artificial Sequence
<220> FEATURE:
<223> OTHER INFORMATION: EXO-code

<400> SEQUENCE: 225
ggccttggtc gcgtgctggc 20

<210> SEQ ID NO 226
<211> LENGTH: 20
<212> TYPE: DNA
<213> ORGANISM: Artificial Sequence
<220> FEATURE:
<223> OTHER INFORMATION: EXO-code

<400> SEQUENCE: 226
ccatgctcgc gcggagtggc 20

<210> SEQ ID NO 227
<211> LENGTH: 20
<212> TYPE: DNA
<213> ORGANISM: Artificial Sequence
<220> FEATURE:
<223> OTHER INFORMATION: EXO-code

<400> SEQUENCE: 227
tgcgatgttg tgagtggccc 20

<210> SEQ ID NO 228
<211> LENGTH: 20
<212> TYPE: DNA
<213> ORGANISM: Artificial Sequence
<220> FEATURE:
<223> OTHER INFORMATION: EXO-code

<400> SEQUENCE: 228
gcgacgtcag gtgggcttgg 20

<210> SEQ ID NO 229
<211> LENGTH: 20
<212> TYPE: DNA
<213> ORGANISM: Artificial Sequence
<220> FEATURE:
<223> OTHER INFORMATION: EXO-code

<400> SEQUENCE: 229
tagcgggtgc gatgtggtgc 20

<210> SEQ ID NO 230

<211> LENGTH: 20
<212> TYPE: DNA
<213> ORGANISM: Artificial Sequence
<220> FEATURE:
<223> OTHER INFORMATION: EXO-code

<400> SEQUENCE: 230
agcgatttcg caggtggtgc 20

<210> SEQ ID NO 231
<211> LENGTH: 12
<212> TYPE: RNA
<213> ORGANISM: Artificial Sequence
<220> FEATURE:
<223> OTHER INFORMATION: EXO-code

<400> SEQUENCE: 231
wwmgygcwym yw 12

<210> SEQ ID NO 232
<211> LENGTH: 11
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (4)..(4)
<223> OTHER INFORMATION: n is a, c, g, or u

<400> SEQUENCE: 232
ccynkvrahc c 11

<210> SEQ ID NO 233
<211> LENGTH: 12
<212> TYPE: RNA
<213> ORGANISM: Artificial Sequence
<220> FEATURE:
<223> OTHER INFORMATION: EXO-code

<400> SEQUENCE: 233
cygsryukrg rg 12

<210> SEQ ID NO 234
<211> LENGTH: 20
<212> TYPE: RNA
<213> ORGANISM: Artificial Sequence
<220> FEATURE:
<223> OTHER INFORMATION: EXO-code

<400> SEQUENCE: 234
ucguagguca ggaagcggcg 20

<210> SEQ ID NO 235
<211> LENGTH: 20
<212> TYPE: RNA
<213> ORGANISM: Artificial Sequence
<220> FEATURE:
<223> OTHER INFORMATION: EXO-code

<400> SEQUENCE: 235
gcgauaggcg gucguugguc 20

<210> SEQ ID NO 236
<211> LENGTH: 20
<212> TYPE: RNA
<213> ORGANISM: Artificial Sequence

```
<220> FEATURE:
<223> OTHER INFORMATION: EXO-code

<400> SEQUENCE: 236

acaguagagc cuucaccggc                                                  20


<210> SEQ ID NO 237
<211> LENGTH: 20
<212> TYPE: RNA
<213> ORGANISM: Artificial Sequence
<220> FEATURE:
<223> OTHER INFORMATION: EXO-code

<400> SEQUENCE: 237

ccgggcguau cuuguggucg                                                  20


<210> SEQ ID NO 238
<211> LENGTH: 20
<212> TYPE: RNA
<213> ORGANISM: Artificial Sequence
<220> FEATURE:
<223> OTHER INFORMATION: EXO-code

<400> SEQUENCE: 238

uggaacgucg augugggccg                                                  20


<210> SEQ ID NO 239
<211> LENGTH: 20
<212> TYPE: RNA
<213> ORGANISM: Artificial Sequence
<220> FEATURE:
<223> OTHER INFORMATION: EXO-code

<400> SEQUENCE: 239

gcuggucagg augcgggggc                                                  20


<210> SEQ ID NO 240
<211> LENGTH: 21
<212> TYPE: RNA
<213> ORGANISM: Artificial Sequence
<220> FEATURE:
<223> OTHER INFORMATION: EXO-code

<400> SEQUENCE: 240

gaugcacauc cgaagccacu u                                                21


<210> SEQ ID NO 241
<211> LENGTH: 11
<212> TYPE: RNA
<213> ORGANISM: Artificial Sequence
<220> FEATURE:
<223> OTHER INFORMATION: EXO-code

<400> SEQUENCE: 241

ddrgkuaggg k                                                           11


<210> SEQ ID NO 242
<211> LENGTH: 20
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (6)..(7)
<223> OTHER INFORMATION: n is a, c, g, or u
<220> FEATURE:
```

<221> NAME/KEY: misc_feature
<222> LOCATION: (10)..(10)
<223> OTHER INFORMATION: n is a, c, g, or u

<400> SEQUENCE: 242
dvvrvnnvdn vdbdbbgugg 20

<210> SEQ ID NO 243
<211> LENGTH: 15
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (10)..(11)
<223> OTHER INFORMATION: n is a, c, g, or u

<400> SEQUENCE: 243
nnvndnnbbn nrykk 15

<210> SEQ ID NO 244
<211> LENGTH: 15
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (4)..(5)
<223> OTHER INFORMATION: n is a, c, g, or u

<400> SEQUENCE: 244
dbdnngkskb bdbgb 15

<210> SEQ ID NO 245
<211> LENGTH: 20
<212> TYPE: RNA
<213> ORGANISM: Artificial Sequence
<220> FEATURE:
<223> OTHER INFORMATION: EXO-code

<400> SEQUENCE: 245
wrvuguryyd gbddddydvb 20

<210> SEQ ID NO 246
<211> LENGTH: 11
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (4)..(4)
<223> OTHER INFORMATION: n is a, c, g, or u

<400> SEQUENCE: 246
dwwnguuggr d 11

<210> SEQ ID NO 247
<211> LENGTH: 14
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (5)..(5)
<223> OTHER INFORMATION: n is a, c, g, or u

<400> SEQUENCE: 247
kdddnguugg rwhb 14

<210> SEQ ID NO 248
<211> LENGTH: 11
<212> TYPE: RNA
<213> ORGANISM: Artificial Sequence
<220> FEATURE:
<223> OTHER INFORMATION: EXO-code

<400> SEQUENCE: 248
ssscaagugg c 11

<210> SEQ ID NO 249
<211> LENGTH: 11
<212> TYPE: RNA
<213> ORGANISM: Artificial Sequence
<220> FEATURE:
<223> OTHER INFORMATION: EXO-code

<400> SEQUENCE: 249
acwcgagwkg c 11

<210> SEQ ID NO 250
<211> LENGTH: 12
<212> TYPE: RNA
<213> ORGANISM: Artificial Sequence
<220> FEATURE:
<223> OTHER INFORMATION: EXO-code

<400> SEQUENCE: 250
uggckugugg cu 12

<210> SEQ ID NO 251
<211> LENGTH: 11
<212> TYPE: RNA
<213> ORGANISM: Artificial Sequence
<220> FEATURE:
<223> OTHER INFORMATION: EXO-code

<400> SEQUENCE: 251
awcuuguggu c 11

<210> SEQ ID NO 252
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (7)..(7)
<223> OTHER INFORMATION: n is a, c, g, or u

<400> SEQUENCE: 252
ddguggnygu gc 12

<210> SEQ ID NO 253
<211> LENGTH: 12
<212> TYPE: RNA
<213> ORGANISM: Artificial Sequence
<220> FEATURE:
<223> OTHER INFORMATION: EXO-code

<400> SEQUENCE: 253
vgugkgkugu gc 12

<210> SEQ ID NO 254
<211> LENGTH: 12
<212> TYPE: RNA
<213> ORGANISM: Artificial Sequence
<220> FEATURE:
<223> OTHER INFORMATION: EXO-code

<400> SEQUENCE: 254
wgcgasgusg yg 12

<210> SEQ ID NO 255
<211> LENGTH: 12
<212> TYPE: RNA
<213> ORGANISM: Artificial Sequence
<220> FEATURE:
<223> OTHER INFORMATION: EXO-code

<400> SEQUENCE: 255
cmycacakcm gy 12

<210> SEQ ID NO 256
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (2)..(2)
<223> OTHER INFORMATION: n is a, c, g, or u

<400> SEQUENCE: 256
rnrdguggcr ug 12

<210> SEQ ID NO 257
<211> LENGTH: 11
<212> TYPE: RNA
<213> ORGANISM: Artificial Sequence
<220> FEATURE:
<223> OTHER INFORMATION: EXO-code

<400> SEQUENCE: 257
skmdrguggc y 11

<210> SEQ ID NO 258
<211> LENGTH: 12
<212> TYPE: RNA
<213> ORGANISM: Artificial Sequence
<220> FEATURE:
<223> OTHER INFORMATION: EXO-code

<400> SEQUENCE: 258
gsgcgkhgug gy 12

<210> SEQ ID NO 259
<211> LENGTH: 12
<212> TYPE: RNA
<213> ORGANISM: Artificial Sequence
<220> FEATURE:
<223> OTHER INFORMATION: EXO-code

<400> SEQUENCE: 259
agcgaygkug yg 12

<210> SEQ ID NO 260
<211> LENGTH: 11
<212> TYPE: RNA
<213> ORGANISM: Artificial Sequence
<220> FEATURE:
<223> OTHER INFORMATION: EXO-code

<400> SEQUENCE: 260
uagcgrgugc g 11

<210> SEQ ID NO 261
<211> LENGTH: 12
<212> TYPE: RNA
<213> ORGANISM: Artificial Sequence
<220> FEATURE:
<223> OTHER INFORMATION: EXO-code

<400> SEQUENCE: 261
agmgrygguc gu 12

<210> SEQ ID NO 262
<211> LENGTH: 12
<212> TYPE: RNA
<213> ORGANISM: Artificial Sequence
<220> FEATURE:
<223> OTHER INFORMATION: EXO-code

<400> SEQUENCE: 262
gcguadkkbg bg 12

<210> SEQ ID NO 263
<211> LENGTH: 12
<212> TYPE: RNA
<213> ORGANISM: Artificial Sequence
<220> FEATURE:
<223> OTHER INFORMATION: EXO-code

<400> SEQUENCE: 263
uasguuggra mg 12

<210> SEQ ID NO 264
<211> LENGTH: 10
<212> TYPE: RNA
<213> ORGANISM: Artificial Sequence
<220> FEATURE:
<223> OTHER INFORMATION: EXO-code

<400> SEQUENCE: 264
augcgggggc 10

<210> SEQ ID NO 265
<211> LENGTH: 12
<212> TYPE: RNA
<213> ORGANISM: Artificial Sequence
<220> FEATURE:
<223> OTHER INFORMATION: EXO-code

<400> SEQUENCE: 265
arabmdaggy gc 12

<210> SEQ ID NO 266
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (9)..(9)
<223> OTHER INFORMATION: n is a, c, g, or u

<400> SEQUENCE: 266
aguuggaang cg 12

<210> SEQ ID NO 267
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (2)..(2)
<223> OTHER INFORMATION: n is a, c, g, or u

<400> SEQUENCE: 267
gnrwgcggkg gc 12

<210> SEQ ID NO 268
<211> LENGTH: 11
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u

<400> SEQUENCE: 268
ugurcwnknw w 11

<210> SEQ ID NO 269
<211> LENGTH: 11
<212> TYPE: RNA
<213> ORGANISM: Artificial Sequence
<220> FEATURE:
<223> OTHER INFORMATION: EXO-code

<400> SEQUENCE: 269
hggrgsagug g 11

<210> SEQ ID NO 270
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (2)..(3)
<223> OTHER INFORMATION: n is a, c, g, or u

<400> SEQUENCE: 270
rnnrrwgcgg gg 12

<210> SEQ ID NO 271
<211> LENGTH: 11
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (10)..(10)
<223> OTHER INFORMATION: n is a, c, g, or u

<400> SEQUENCE: 271
kmgurwrucn w 11

<210> SEQ ID NO 272
<211> LENGTH: 12
<212> TYPE: RNA
<213> ORGANISM: Artificial Sequence
<220> FEATURE:
<223> OTHER INFORMATION: EXO-code
<220> FEATURE:
<221> NAME/KEY: misc_feature
<222> LOCATION: (4)..(4)
<223> OTHER INFORMATION: n is a, c, g, or u

<400> SEQUENCE: 272
krdnwggugg ch 12

<210> SEQ ID NO 273
<211> LENGTH: 11
<212> TYPE: RNA
<213> ORGANISM: Artificial Sequence
<220> FEATURE:
<223> OTHER INFORMATION: EXO-code

<400> SEQUENCE: 273
gggggcruau g 11

<210> SEQ ID NO 274
<211> LENGTH: 20
<212> TYPE: RNA
<213> ORGANISM: Artificial Sequence
<220> FEATURE:
<223> OTHER INFORMATION: EXO-code

<400> SEQUENCE: 274
auucgucgag uacagaccug 20

<210> SEQ ID NO 275
<211> LENGTH: 20
<212> TYPE: RNA
<213> ORGANISM: Artificial Sequence
<220> FEATURE:
<223> OTHER INFORMATION: EXO-code

<400> SEQUENCE: 275
gcgcagggag ggcuuggguc 20

<210> SEQ ID NO 276
<211> LENGTH: 12
<212> TYPE: RNA
<213> ORGANISM: Artificial Sequence
<220> FEATURE:

<223> OTHER INFORMATION: EXO-code

<400> SEQUENCE: 276
agcgacguug cg 12

<210> SEQ ID NO 277
<211> LENGTH: 12
<212> TYPE: RNA
<213> ORGANISM: Artificial Sequence
<220> FEATURE:
<223> OTHER INFORMATION: EXO-code

<400> SEQUENCE: 277
gcguauggcg ug 12

<210> SEQ ID NO 278
<211> LENGTH: 12
<212> TYPE: RNA
<213> ORGANISM: Artificial Sequence
<220> FEATURE:
<223> OTHER INFORMATION: EXO-code

<400> SEQUENCE: 278
uagguuggaa ag 12

<210> SEQ ID NO 279
<211> LENGTH: 12
<212> TYPE: RNA
<213> ORGANISM: Artificial Sequence
<220> FEATURE:
<223> OTHER INFORMATION: EXO-code

<400> SEQUENCE: 279
gggcgucgug gc 12

<210> SEQ ID NO 280
<211> LENGTH: 10
<212> TYPE: RNA
<213> ORGANISM: Artificial Sequence
<220> FEATURE:
<223> OTHER INFORMATION: EXO-code

<400> SEQUENCE: 280
augcgggggc 10

<210> SEQ ID NO 281
<211> LENGTH: 10
<212> TYPE: RNA
<213> ORGANISM: Artificial Sequence
<220> FEATURE:
<223> OTHER INFORMATION: EXO-code

<400> SEQUENCE: 281
aaguggcgug 10

<210> SEQ ID NO 282
<211> LENGTH: 11
<212> TYPE: RNA
<213> ORGANISM: Artificial Sequence
<220> FEATURE:
<223> OTHER INFORMATION: EXO-code

<400> SEQUENCE: 282
ccgcaagugg c 11

```
<210> SEQ ID NO 283
<211> LENGTH: 11
<212> TYPE: RNA
<213> ORGANISM: Artificial Sequence
<220> FEATURE:
<223> OTHER INFORMATION: EXO-code

<400> SEQUENCE: 283

aucuuguggu c                                                            11


<210> SEQ ID NO 284
<211> LENGTH: 10
<212> TYPE: RNA
<213> ORGANISM: Artificial Sequence
<220> FEATURE:
<223> OTHER INFORMATION: EXO-code

<400> SEQUENCE: 284

gugguugugc                                                              10


<210> SEQ ID NO 285
<211> LENGTH: 11
<212> TYPE: RNA
<213> ORGANISM: Artificial Sequence
<220> FEATURE:
<223> OTHER INFORMATION: EXO-code

<400> SEQUENCE: 285

guguggugug c                                                            11


<210> SEQ ID NO 286
<211> LENGTH: 11
<212> TYPE: RNA
<213> ORGANISM: Artificial Sequence
<220> FEATURE:
<223> OTHER INFORMATION: EXO-code

<400> SEQUENCE: 286

acucgagugg c                                                            11


<210> SEQ ID NO 287
<211> LENGTH: 12
<212> TYPE: RNA
<213> ORGANISM: Artificial Sequence
<220> FEATURE:
<223> OTHER INFORMATION: EXO-code

<400> SEQUENCE: 287

ccccacagca gu                                                           12


<210> SEQ ID NO 288
<211> LENGTH: 12
<212> TYPE: RNA
<213> ORGANISM: Artificial Sequence
<220> FEATURE:
<223> OTHER INFORMATION: EXO-code

<400> SEQUENCE: 288

uggcguguggcu                                                            12


<210> SEQ ID NO 289
<211> LENGTH: 10
<212> TYPE: RNA
<213> ORGANISM: Artificial Sequence
<220> FEATURE:
<223> OTHER INFORMATION: EXO-code
```

<400> SEQUENCE: 289
aaguggcgug 10

<210> SEQ ID NO 290
<211> LENGTH: 10
<212> TYPE: RNA
<213> ORGANISM: Artificial Sequence
<220> FEATURE:
<223> OTHER INFORMATION: EXO-code

<400> SEQUENCE: 290
aaguggcgug 10

<210> SEQ ID NO 291
<211> LENGTH: 10
<212> TYPE: RNA
<213> ORGANISM: Artificial Sequence
<220> FEATURE:
<223> OTHER INFORMATION: EXO-code

<400> SEQUENCE: 291
aagaggcgug 10

<210> SEQ ID NO 292
<211> LENGTH: 10
<212> TYPE: RNA
<213> ORGANISM: Artificial Sequence
<220> FEATURE:
<223> OTHER INFORMATION: EXO-code

<400> SEQUENCE: 292
aagucgcgug 10

<210> SEQ ID NO 293
<211> LENGTH: 10
<212> TYPE: RNA
<213> ORGANISM: Artificial Sequence
<220> FEATURE:
<223> OTHER INFORMATION: EXO-code

<400> SEQUENCE: 293
aagugccgug 10

<210> SEQ ID NO 294
<211> LENGTH: 10
<212> TYPE: RNA
<213> ORGANISM: Artificial Sequence
<220> FEATURE:
<223> OTHER INFORMATION: EXO-code

<400> SEQUENCE: 294
aaguggagug 10

<210> SEQ ID NO 295
<211> LENGTH: 20
<212> TYPE: RNA
<213> ORGANISM: Artificial Sequence
<220> FEATURE:
<223> OTHER INFORMATION: EXO-code

<400> SEQUENCE: 295
ccgggcguau cuuguggucg 20

<210> SEQ ID NO 296
<211> LENGTH: 11

<212> TYPE: RNA
<213> ORGANISM: Artificial Sequence
<220> FEATURE:
<223> OTHER INFORMATION: EXO-code

<400> SEQUENCE: 296
aucuuguggu c 11

<210> SEQ ID NO 297
<211> LENGTH: 11
<212> TYPE: RNA
<213> ORGANISM: Artificial Sequence
<220> FEATURE:
<223> OTHER INFORMATION: EXO-code

<400> SEQUENCE: 297
gugcuucugu a 11

<210> SEQ ID NO 298
<211> LENGTH: 11
<212> TYPE: RNA
<213> ORGANISM: Artificial Sequence
<220> FEATURE:
<223> OTHER INFORMATION: EXO-code

<400> SEQUENCE: 298
auguuguggu c 11

<210> SEQ ID NO 299
<211> LENGTH: 11
<212> TYPE: RNA
<213> ORGANISM: Artificial Sequence
<220> FEATURE:
<223> OTHER INFORMATION: EXO-code

<400> SEQUENCE: 299
aucuucuggu c 11

<210> SEQ ID NO 300
<211> LENGTH: 11
<212> TYPE: RNA
<213> ORGANISM: Artificial Sequence
<220> FEATURE:
<223> OTHER INFORMATION: EXO-code

<400> SEQUENCE: 300
aucuugaggu c 11

<210> SEQ ID NO 301
<211> LENGTH: 11
<212> TYPE: RNA
<213> ORGANISM: Artificial Sequence
<220> FEATURE:
<223> OTHER INFORMATION: EXO-code

<400> SEQUENCE: 301
aucuugucgu c 11

<210> SEQ ID NO 302
<211> LENGTH: 11
<212> TYPE: RNA
<213> ORGANISM: Artificial Sequence
<220> FEATURE:
<223> OTHER INFORMATION: EXO-code

<400> SEQUENCE: 302
aucuugugcu c 11

<210> SEQ ID NO 303
<211> LENGTH: 11
<212> TYPE: RNA
<213> ORGANISM: Artificial Sequence
<220> FEATURE:
<223> OTHER INFORMATION: EXO-code

<400> SEQUENCE: 303
aucuugugga c 11

<210> SEQ ID NO 304
<211> LENGTH: 10
<212> TYPE: RNA
<213> ORGANISM: Artificial Sequence
<220> FEATURE:
<223> OTHER INFORMATION: EXO-code

<400> SEQUENCE: 304
augcgggggc 10

<210> SEQ ID NO 305
<211> LENGTH: 10
<212> TYPE: RNA
<213> ORGANISM: Artificial Sequence
<220> FEATURE:
<223> OTHER INFORMATION: EXO-code

<400> SEQUENCE: 305
ggucggacgg 10

<210> SEQ ID NO 306
<211> LENGTH: 10
<212> TYPE: RNA
<213> ORGANISM: Artificial Sequence
<220> FEATURE:
<223> OTHER INFORMATION: SEQ ID NO:307

<400> SEQUENCE: 306
uugcgggggc 10

<210> SEQ ID NO 307
<211> LENGTH: 10
<212> TYPE: DNA
<213> ORGANISM: Artificial Sequence
<220> FEATURE:
<223> OTHER INFORMATION: EXO-code

<400> SEQUENCE: 307
aagcgggggc 10

<210> SEQ ID NO 308
<211> LENGTH: 10
<212> TYPE: RNA
<213> ORGANISM: Artificial Sequence
<220> FEATURE:
<223> OTHER INFORMATION: EXO-code

<400> SEQUENCE: 308
auccgggggc 10

<210> SEQ ID NO 309
<211> LENGTH: 10
<212> TYPE: RNA
<213> ORGANISM: Artificial Sequence

```
<220> FEATURE:
<223> OTHER INFORMATION: EXO-code

<400> SEQUENCE: 309

augggggggc                                                              10


<210> SEQ ID NO 310
<211> LENGTH: 10
<212> TYPE: RNA
<213> ORGANISM: Artificial Sequence
<220> FEATURE:
<223> OTHER INFORMATION: EXO-code

<400> SEQUENCE: 310

augccggggc                                                              10


<210> SEQ ID NO 311
<211> LENGTH: 10
<212> TYPE: RNA
<213> ORGANISM: Artificial Sequence
<220> FEATURE:
<223> OTHER INFORMATION: EXO-code

<400> SEQUENCE: 311

augcgcgggc                                                              10


<210> SEQ ID NO 312
<211> LENGTH: 10
<212> TYPE: RNA
<213> ORGANISM: Artificial Sequence
<220> FEATURE:
<223> OTHER INFORMATION: EXO-code

<400> SEQUENCE: 312

augcggcggc                                                              10


<210> SEQ ID NO 313
<211> LENGTH: 10
<212> TYPE: RNA
<213> ORGANISM: Artificial Sequence
<220> FEATURE:
<223> OTHER INFORMATION: EXO-code

<400> SEQUENCE: 313

augcgggcgc                                                              10
```

COMPOSITIONS AND METHODS FOR LOADING EXTRACELLULAR VESICLES WITH CHEMICAL AND BIOLOGICAL AGENTS/MOLECULES

CROSS REFERENCE TO RELATED APPLICATIONS

This application claims the benefit of priority to U.S. Provisional Application No. 62/504,941, filed on May 11, 2017, and to U.S. Provisional Application No. 62/631,060, filed on Feb. 15, 2018, the disclosures of which are hereby incorporated by reference.

GOVERNMENT FUNDING

This invention was made with government support under grant numbers HL126082, EB021454, and EB023262 awarded by National Institutes of Health. The government has certain rights in the invention.

FIELD

The present disclosure relates generally to compositions and methods for loading exosomes/extracellular vesicles with chemical and biological agents and/or for modulating cargo sorting to exosomes/extracellular vesicles.

BACKGROUND

In a milliliter of human blood, there are roughly one billion exosomes: lipid vesicles that contain proteins, miRNA, and mRNA. Cells release exosomes into the extracellular environment where they participate in a number of physiological and pathophysiological processes. Exosomes originate from multivesicular bodies (MVBs), which fuse with the plasma cell membrane before release into the extracellular environment. Upon release, exosomes can fuse with neighboring cells to transfer their cargo. It is now known that exosomes are not merely vehicles for unwanted cellular proteins and 'junk RNA' but that cells actively secrete exosomes to modulate their microenvironment.

Exosomes are involved in the pathogenesis of several diseases including cancer, neurodegenerative, autoimmune, and liver diseases. Several studies have examined the role of exosomes in cancer growth and metastasis [Costa-Silva B, et al. Nat Cell Biol. 2015; 17(6):816-826; Grange C, et al. Cancer research. 2011; 71(15):5346-5356; Hood J L, et al. Cancer research. 2011; 71(11):3792-3801; Kucharzewska P, et al. Proceedings of the National Academy of Sciences of the United States of America. 2013; 110(18):7312-7317; Peinado H, et al. Nat Med. 2012; 18(6):883-891]. Since extracellular vesicles such as exosomes derived from tumor cells have the potential to convert adipose-derived mesenchymal stem cells into tumor-associated myofibroblasts, it has been proposed that these exosomes can contribute to tumor progression and the malignant phenotype by generating tumor stroma [Cho J A, et al. Int J Oncol. 2012; 40(1):130-138]. Exosomes also play a role in inducing metastases, which are ultimately responsible for over 90% of cancer-related deaths: the treatment of metastatic disease remains a clinical challenge. Cancer cell-derived exosomes have the potential to convert healthy cells into tumor-forming cells in their immediate microenvironment: exosomes released by cancer cells can transfer onco-genes (mainly via oncogenic small RNAs) to recipient cells, induce migration of cancer cells, and promote angiogenesis, which are critical cancer "hallmarks" [Meehan K, et al. Crit Rev Clin Lab Sci. 2015:1-11]. Due to their inherent ability for systemic spread, they can also initiate new tumor growth at distant sites by preparing a pre-metastatic niche. In particular, it has been shown how exosomes from lung-tropic 4175-LuT cancer cells (a MDA-MB-231 breast cancer sub-line) specifically located to the lung and were taken up by lung-resident fibroblasts after systemic administration. These exosomes were able to not only redirect the migration of bone-tropic tumor cells from bone sites to the lung but also increased the metastatic capacity of those cells in the lung by 10,000 fold [Hoshino A, et al. Nature. 2015; 527(7578):329-335]]. These data indicate that circulating exosomes prepare discrete sites for future metastatic tumors consistent with the seed-soil hypothesis. Exosomes and/or extracellular vesicles also play a role in physiological processes and can have regenerative effects. For example, exosomes/extracellular vesicles derived from mesenchymal stem cells (MSCs) have been shown to mediate cardiac tissue repair after myocardial infarction by modulating the injured tissue environment, inducing angiogenesis, and inducing cellular proliferation and differentiation [Barile L et al. Cardiovasc Res. 2014; 103(4):530-541; Lai R C. et al. Stem cell research. 2010; 4(3):214-222].

There is, therefore, an ongoing and unmet need for compositions and methods that are useful for blocking undesired cellular communication by reprogramming exosomes to halt and/or reverse disease progression, and for reprogramming or loading exosomes with chemical and biological agents so that they can deliver other desirable cargo to target cells. The present disclosure is pertinent to these needs.

SUMMARY OF THE DISCLOSURE

The present disclosure relates to RNA polynucleotide sequences (referred to herein from time to time as "EXO-Codes") that are capable of a) selectively sorting to extracellular vesicles such as exosomes, and b) delivering a variety of cargo types to program or reprogram the extracellular vesicles. While non-limiting embodiments of the disclosure are illustrated using exosomes, the disclosure includes using EXO-Codes to sort polynucleotides containing the EXO-Codes to any secreted membranous structures, including but not necessarily limited to exosomes, vesicles, microvesicles, micro-particles, endosomal derived vesicles, multivesicular bodies, apoptotic bodies, and combinations thereof.

In certain aspects the disclosure comprises an EXO-Code comprising reagent that includes an RNA segment, wherein the RNA segment comprises an EXO-Code sequence, and wherein the agent further comprises a cargo moiety. The cargo moiety can be selected from polynucleotides, peptides, polypeptides, proteins, fluorophores, and small (drug) molecules.

The disclosure includes comparing the effects of any modified polynucleotide and/or modified exosome and/or modified cellular composition to a suitable reference. The reference can comprise any suitable control, value or measurement of the function of the modified polynucleotides and/or modified exosomes and/or modified cellular compositions, such as a standardized curve, a titration, the area under a curve, or a comparison to the capability of naturally occurring compositions or processes, including but not limited to the efficiency, kinetics, amount, etc. of RNA-exosome sorting in unmodified or other control systems.

The disclosure includes compositions, including but not limited to pharmaceutical compositions suitable for human and/or veterinary uses, wherein the compositions comprise EXO-Code containing polynucleotides. Pharmaceutical compositions generally comprise at least one pharmaceutically acceptable excipient, carrier, diluent, and the like. The disclosure includes cell cultures modified to produce exosomes that contain the EXO-Code containing polynucleotides, cell culture medium comprising the exosomes, as well as isolated and/or purified exosome populations, wherein at least some of the exosomes in the population comprise EXO-Code containing polynucleotides. The disclosure includes pharmaceutical compositions comprising exosomes that contain EXO-Code containing polynucleotides. The disclosure includes methods of making the EXO-Code containing polynucleotides, such as by chemical synthesis, or in vitro or in vivo transcription. Also included are combinations of distinct polynucleotides comprising EXO-Codes wherein the combination has a greater than additive or synergistic effect on at least one EXO-Code/exosome sorting property and/or effect on a cell into which a modified exosome of this disclosure is introduced. Polynucleotides of this disclosure can comprise one, or more than one EXO-Code sequence, and can comprise more than one of the same EXO-Code sequence, or distinct EXO-Code sequences.

In more detail, multivalency is a well-established approach in engineering higher affinity interactions between two moieties. An essentially unlimited number of EXO-Codes and combinations of distinct EXO-Codes could be incorporated into any single polynucleotide for the potential to achieve enhanced exosomal delivery. However, there may be an inverse relationship between increased affinity and size of the polynucleotide as more EXO-Codes are incorporated. Thus, in non-limiting embodiments, polynucleotides of this disclosure comprise 1, 2, 3, or more EXO-Codes. Further, although an advantage of EXO-Codes is realized when electroporated directly into living cells for active exosomal packaging, in applications where this is infeasible, direct exosome loading may be used. For the purposes of in vivo delivery the EXO-Codes could be loaded directly into isolated patient-derived exosomes via well-established electroporation protocols. They may also be incorporated into any synthetic lipidic delivery vehicle such as liposomes, cationic lipoplexes, other polymeric delivery vehicles or any host of delivery vehicle capable of delivering the EXO-Codes to the cytoplasm of recipient cells. These cells could then package the EXO-Codes into exosomes for in vivo exosome programming, or for other purposes.

The disclosure includes kits for making, screening, and using EXO-Codes and polynucleotides comprising them for a wide variety of research, therapeutic and prophylactic approaches that will be apparent to those skilled in the art given the benefit of the present disclosure. The kits may comprise reagents for making and screening exosomes and may include EXO-Code containing polynucleotides and may contain reagents useful for introducing such polynucleotides into cells.

BRIEF DESCRIPTION OF THE FIGURES

For a fuller understanding of the nature and objects of the disclosure, reference should be made to the following detailed description taken in conjunction with the accompanying figures.

FIG. 5 shows (A) the diversity of the RNA library decreases with each round of selection. This shows that our selection procedure leads to enrichment of specific sequences. (B) Top 15 enriched EXO-Codes after 10 rounds of selection in MDA-MB-231 cells.

FIG. 7 shows IUPAC nucleotide codes of the present disclosure and a legend for IUPAC nucleotide codes.

FIG. 8 shows (A and B) normalized in silico dock score, which show high correlation ($R2=0.82$) with experimentally determined binding affinities of RNA sequences to HnRNP L. The sequences within the EXO-Codes bind to HnRNP L with predicted binding affinities of 3.23 nM (CCCCACA) and 223.2 nM (CACAGCA). (C) Surface rendered presentation of CCCCACA (white) binding to the RNA-recognition motif (RRM) of HNRNP L. (D) Calculated electrostatic surface potential shows the interactions of CCCCACA with HnRNP L (anionic charges and cationic charges shown). (E) The main binding motif to HnRNP L as predicted by in silico docking is "CACA". Prefacing "CACA" with "CCC" as can be found in our motif (CCCCCACA) did not seem to induce sterical hindrances since the in silico dock score still ranked the motif in the low nanomolar range. The binding of CCCCCACA to HnRNP L is mediated by intermolecular hydrogen bonds (dashed lines). The binding is further stabilized by electrostatic interactions between C4 and Arg102 and by stacking interactions between A5 and Tyr168. The data are is consistent with binding of HnRNP L to CA-repeats (e.g., CACACA) or repeats separated by spacers such as CANRCA and CANRCA.

FIG. 16 shows in (A): Analyzing the top 1,000 sequences from the latest selection round to MEME motif algorithm demonstrated highly statistically significant motifs (lowest E-value motifs shown). The most significant motifs from RAW and MSC cells show high similarity. (B) Less statistically significant motifs from PC-3 and RAW cells show high similarity.

FIG. 18 shows motifs sharing similar sequence elements were aligned visually and grouped; arrows indicate similar motifs between the cell lines.

FIG. 21 shows sorting of SNAIL siRNA tagged with the Hybrid EXO-Code to exosomes derived from MDA-MB-231 cells. Mutations were introduced into the Hybrid EXO-Code to assess the effect on sorting.

FIG. 22 shows sorting of SNAIL siRNA tagged with an M8 EXO-Code to exosomes derived from MDA-MB-231 cells. Mutations were introduced into the M8 EXO-Code to assess the effect on sorting.

DETAILED DESCRIPTION

Figure 1:
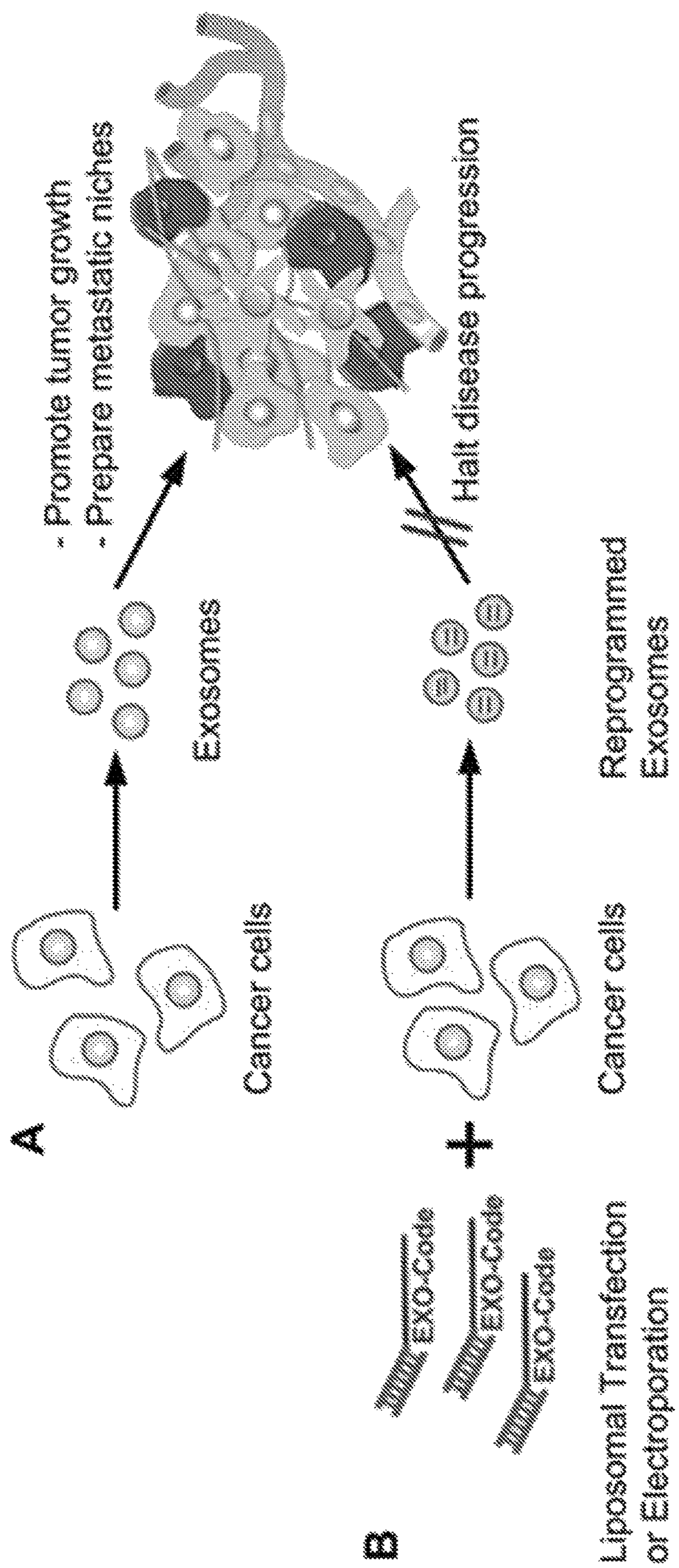
FIG. 1 provides a non-limiting illustration of the use of EXO-Code containing polynucleotides to reprogram exosomes released from cancer cells, thereby halting disease progression. (A) Tumor-secreted exosomes have been shown to prepare metastatic niches in distant organs. (B) Schematic depicting EXO-Codes conjugated to a therapeutic cargo to reprogram tumor-derived exosomes to halt disease progression.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein. Each RNA sequence includes its DNA equivalent, and each DNA sequence includes its RNA equivalent. Complementary and anti-parallel polynucleotide sequences are included. Every DNA and RNA sequence encoding polypeptides disclosed herein is encompassed by this disclosure. The disclosure includes polynucleotide consensus sequences and motifs.

The present disclosure relates to RNA polynucleotide sequences (referred to herein from time to time as "EXO-Codes") that are capable of a) selectively sorting to extracellular vesicles such as exosomes, and b) delivering a variety of cargo types to program or reprogram the extracellular vesicles. While non-limiting embodiments of the disclosure are illustrated using exosomes, the disclosure includes using EXO-Codes to sort polynucleotides containing the EXO-Codes to any secreted membranous structures, including but not necessarily limited to exosomes, vesicles, microvesicles, micro-particles, endosomal derived vesicles, multivesicular bodies, apoptotic bodies, and combinations thereof.

With respect to one embodiment, and as will be recognized by those skilled in the art, exosomes are membrane-bound vesicles secreted by cells. They belong to the group of extracellular vesicles that collectively include exosomes, microvesicles, apoptotic bodies, and other extra-vesicular populations, such as ectosomes. Their size is in the range of 30-150 nanometers. Enriched proteins in exosomes include but are not limited to endosomal and transmembrane markers such as tetraspanins (CD63, CD9, CD81), integrins, cell adhesion molecules (EpCAM), growth factor receptors, heterotrimeric G proteins, and phosphatidylserine-binding MFG-E8/lactadherin. Further, exosomes may be enriched in endosome or membrane-binding proteins (Tsg101), annexins, Rabs, and signal transduction or scaffold proteins. However, the presence of any such protein constituents is not required for a released vesicle to be considered an exosome. In particular, exosome membrane composition is varied and may comprise different proportions of phospholipids (such as phosphatidylinositol, phosphatidylethanolamine, phosphatidylcholine, and phosphatidylserine) as well as their "-lyso" and "glycerol" derivatives, sphingomyelin, glycosphingolipids, ceramides, cholesterol (and esterified cholesterol), as well as lysobisphosphatidic acid (LBPA) among other lipids. The exosomes used to illustrate embodiments of the disclosure that are modified using the EXO-Codes as further described herein can deliver the cargo to targeted cells. In certain approaches the disclosure comprises reprogramming pathological exosomes. In other approaches the disclosure comprises the modulation of nucleic acid or cargo sorting to exosomes. In embodiments, exosomes or other secreted membranous structures comprise RNA polynucleotides described herein. An exosome "comprises" an RNA polynucleotide when the RNA polynucleotide is incorporated into an exosome. The RNA polynucleotide may therefore be contained in the interior of the exosome, such as within an aqueous solution or mixture contained therein, such as cytosol or other cellular liquid that is secreted as a component of the exosome, or a synthetic solution. In embodiments, the RNA polynucleotide may be at least partially embedded in the membrane structure. In embodiments, a cargo portion of an RNA polynucleotide may also be contained within the exosome, or the cargo may be at least partially embedded in the membrane, or the cargo may protrude outward from the membrane, such as a bilayered exosome membrane.

The disclosure includes comparing the effects of any modified polynucleotide and/or modified exosome and/or modified cellular composition to a suitable reference. The reference can comprise any suitable control, value or measurement of the function of the modified polynucleotides and/or modified exosomes and/or modified cellular compositions, such as a standardized curve, a titration, the area under a curve, or a comparison to the capability of naturally occurring compositions or processes, including but not limited to the efficiency, kinetics, amount, etc. of RNA-exosome sorting in unmodified or other control systems. In embodiments, an exosome or other membranous structure into which RNA polynucleotides comprising an EXO-Code sequence of this disclosure are preferentially sorted into exosomes secreted by a cell, and as such the exosomes comprise more of the RNA polynucleotides relative to a control value. Suitable control values will be apparent to those skilled in the art given the benefit of this disclosure, and can include, for example, an amount of non-EXO-Code containing RNA that is sorted into exosomes, and/or the amount of a scrambled RNA sequence (i.e., fully or partially randomly generated sequence) that is sorted to the exosomes.

In embodiments, any one of the RNA EXO-Code sequences of this disclosure can comprise or consist of the sequences or segments of the sequences presented in the description of the invention, the tables of this disclosure, and the figures of this disclosure. In embodiments, the sequences can include one or more insertions, deletions, and mutations, so long as they retain their capacity to be preferentially sorted into exosomes, or other membranous structures. In certain embodiments, the EXO-Code sequences comprise or consist of between 3-70 nucleotides, inclusive, and including all integers and ranges of integers there between. In embodiments, an RNA polynucleotide comprises at least one EXO-Code sequence described herein. In embodiments, an RNA polynucleotide comprises at 2, 3, 4, 5, or more than 5 EXO-Code sequences described herein.

Exosomes modified according to this disclosure will generally have a diameter of 30-150 nm and an internal radius of approximately 10-70 nm, thus the internal volume of one exosome ($4/3\ \pi R^3$) is approximately $4\times10^{-24}$-$1.5\times10^{-21}$ $m^3$. The volume of one average 50 kDa protein or 100 nt RNA molecule is approximately $6\times10^{-26}$ $m^3$. Thus, each exosome is expected to be able to accommodate approximately 70-25 000 small RNA or protein molecules (see, for example, Li, et al. Analysis of the RNA content of the exosomes derived from blood serum and urine and its potential as biomarkers, Phil. Trans. R. Soc. B369: 20130502, dx.doi.org/10.1098/rstb.2013, the description of which is incorporated herein by reference.). Therefore even very large RNAs may be incorporated into exosomes, provided an active packaging apparatus.

In certain aspects the disclosure comprises an EXO-Code comprising reagent that includes an RNA segment, wherein the RNA segment comprises an EXO-Code sequence, and wherein the agent further comprises a cargo moiety. The cargo moiety can be selected from polynucleotides, peptides, polypeptides, proteins, fluorophores, and small (drug) molecules.

EXO-Code containing polynucleotides may comprise modifications to improve their function, bioavailability, stability, and the like. For example, EXO-Code containing polynucleotides may include modified nucleotides and/or modified nucleotide linkages. Suitable modifications and methods for making them are well known in the art. Some examples include but are not limited to polynucleotides which comprise modified ribonucleotides or deoxyribonucleotides. For example, modified ribonucleotides may comprise methylations and/or substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In embodiments modified nucleotides comprise methyl-cytidine and/or pseudo-uridine. The nucleotides may be linked by phosphodiester linkages or by a synthetic linkage, i.e., a linkage other than a phosphodiester linkage. Examples of inter-nucleoside linkages in the polynucleotide agents that can be used in the disclosure include, but are not limited to, phosphodiester, alkylphosphonate, phosphorothioate, phosphorodithioate, phosphate ester, alkylphosphonothioate, phosphoramidate, carbamate, carbonate, morpholino, phosphate triester, acetamidate, carboxymethyl ester, or combinations thereof.

In certain aspects, such as for modulating the expression of a gene in a target cell or modifying a property or function of an exosome, and/or for reprogramming exosomes, the EXO-Code containing polynucleotides may comprise a functional polynucleotide segment. A "functional" segment means a segment of the polynucleotide that is capable of exerting an effect on a cell into which it is introduced, and particularly when introduced as a component of, or by fusion with, an exosome or other membranous structure. In embodiments, the effect that is exerted on the cell comprises inhibition of RNA transcription and/or protein translation, editing of chromosome, interfering with the function of an enzyme, and/or causing or participating in causing a change in a cell phenotype, such as a change from a pathological phenotype to a non-pathological phenotype, a non-limiting example of which is a change from a malignant to a non-malignant phenotype. In an embodiment, the recipient cell is reprogrammed to produce a protein it did not produce before receiving the EXO-Code containing polynucleotide. The functional segment may also cause or participate in causing an inhibition of growth of cells, including but not limited to cell death.

In embodiments, the effect that is exerted on the cell comprise expression of a protein encoded by a cargo RNA that is a component of an EXO-Code containing polynucleotide described herein. In non-limiting embodiments, the EXO-Code containing polynucleotides may be adapted for use in RNA interference (RNAi) mediated silencing or downregulation of a target mRNA or may be adapted for delivery of microRNA (miRNA) or other non-coding RNA (ncRNA). This can be achieved, for example, by joining the EXO-Code sequence to at least one RNAi agent. RNAi agents may be expressed in cells as short hairpin RNAs (shRNA). shRNA is an RNA molecule that contains a sense strand, antisense strand, and a short loop sequence between the sense and antisense fragments. shRNA is exported into the cytoplasm where it is processed by dicer into short interfering RNA (siRNA). siRNA are 21-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of a target RNA, the polynucleotide component may be either siRNA, shRNA, or miRNA. In embodiments, a functional RNA segment is transcribed in cis with the EXO-code sequence. In embodiments, a functional RNA segment may be chemically attached to the EXO-code containing sequence. In embodiments, targeting an RNA by a functional RNA segment can be achieved by using a ribozyme as the cargo. In embodiments, the ribozyme comprises a hammerhead ribozyme, a hairpin ribozyme, or a Hepatitis Delta Virus ribozyme.

In embodiments, a segment of an EXO-Code containing polynucleotide comprises a functional RNA segment that can participate in CRISPR (clustered regularly interspaced short palindromic repeats) DNA or RNA editing. In embodiments, a cargo RNA can be a CRISPR RNA (crRNA) or a guide RNA, such as sgRNA. The sequence of the cargo RNA may thus comprise a segment that is the same as or complementarity to any CRISPR site in a target polynucleotide, which may also include a protospacer adjacent motif (PAM), which is typically a 2-6 base pair DNA sequence, immediately following the DNA sequence targeted by a nuclease that can catalyze a single or double stranded DNA break. In embodiments, a cargo RNA segment that can participate in CRISPR DNA or RNA editing will comprise or consist of a segment that is from 12-20 nucleotides in length, and may be the same as or complementary to a so-called spacer sequence in a target. The 12-20 nucleotides directed to the spacer sequence may be present in the cargo RNA, regardless of whether the targeting RNA is a crRNA or a guide RNA. In embodiments, a separate trans-activating crRNA (tracrRNA) can be used to assist in maturation of a crRNA. Any RNA or mRNA or DNA can be targeted. In non-limiting embodiments, the well-known Snail or Slug mRNA, or the S100A4 mRNA, or a combination thereof is targeted.

The EXO-Code containing polynucleotides may or may not encode a protein, including but not necessarily limited to a protein that is intended to facilitate RNA and/or exosome localization and/or visualization, or a protein that is capable of exerting a function in an exosome and/or in a target cell. In embodiments, an EXO-Code containing polynucleotide may contain an internal ribosome entry sequence (IRES). In non-limiting embodiments, the IRES is a wild-type or modified Encephalomyocarditis virus IRES or Hepatitis C Virus IRES. In embodiments, a sequence proximal to the IRES, such as 3' to the IRES, comprises an open reading frame. In embodiments, a sequence 3' to the IRES comprises a translational stop codon so that translation of the open reading frame can stop. In embodiments, a poly-A tail may be present on an EXO-Code containing polynucleotide of this disclosure. In embodiments, an EXO-Code containing polynucleotide of this disclosure may be provided with a 5' cap. Thus, embodiments of the disclosure include an EXO-Code containing polynucleotide, at least a portion of which can function as an mRNA, thereby including a translational open reading frame. In embodiments, the EXO-Code containing polynucleotides may include a sequence encoding one or more nucleases, including but not limited Cas nucleases, such as a Cas9 nuclease. In embodiments, the EXO-Code containing polynucleotides may encode other nucleases, such as Transcription activator-like effector nucleases (TALENs) or zinc-finger nucleases (ZFNs). The EXO-Code polynucleotides can encode or include nuclear localization signals.

In certain aspects the EXO-Code containing polynucleotides may encode and/or be modified to be attached to a protein that produces a detectable signal, including but not necessarily limited to a visually detectable signal, a fluorescent signal, etc. In certain approaches the EXO-Code containing polynucleotides may be covalently linked to any peptide or polypeptide. The type, sequence and function of such moieties are not particularly limited, other than by the size constraints of the exosome or other secreted membranous structure. In certain approaches the EXO-Code containing polynucleotide can be linked to a functional protein or fragment thereof. In certain embodiments the protein is selected from enzymes, including but not limited to those described above, or receptor ligands, transcriptional factors, growth factors, antibodies or antigen-binding fragments thereof, peptide or protein immunogens that can be used for stimulating an immune response (i.e., a vaccine), protein-based chemotherapeutic agents, and toxins. In certain embodiments, the linked protein comprises insulin, a growth hormone or a growth hormone releasing factor, a platelet derived growth factor, an epidermal growth factor, any insulin-like growth factor, a clotting factor, an interferon, any interleukin, a lymphotoxin, and the like. In embodiments the linked protein comprises a protein-based toxin, such as enzymatically active toxins which include but are not limited to diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, and *Phytolaca americana* proteins (PAPI, PAPII, and PAP-S. In general, protein with a volume of $1.5\times10^{-21}$ $m^3$ would be expected to be able to be present inside exosomes with a diameter of 30-150 nm. In particular, exosomes with a diameter of 30-150 nm have an internal radius of approximately 10-70 nm, thus the internal volume of one exosome ($4/3\ \pi R^3$) is approximately $4\times10^{-24}$-$1.5\times10^{-21}$ $m^3$. The volume of one average 50 kDa protein or 100 nt RNA molecule is approximately $6\times10^{-26}$ $m^3$. In non-limiting embodiments each exosome can accommodate any proteins with a volume smaller than $1.5\times10^{-21}$ $m^3$. In cases where the EXO-Codes mediate sorting to larger extracellular vesicles, larger proteins can be accommodated.

In embodiments, cells expressing EXO-Code containing polynucleotides described herein secrete exosomes that contain the polynucleotides, and such exosomes are taken up by distinct cells. "Distinct cells" means cells that do not comprise the EXO-Code containing polynucleotides prior to an initial exposure to the EXO-Code containing polynucleotides via exosome uptake. The EXO-Code containing polynucleotides can accordingly then exert an effect on the distinct cells via the cargo that is a component of the EXO-Code containing polynucleotides.

In embodiments the EXO-Code sequence does not include the sequence 5' UAG GGA AGA GAA GGA CAU AUG AU (SEQ ID NO:1) and/or does not include the sequence 5' UU GAC UAG UAC AUG ACC ACU UGA 3' (SEQ ID NO:2). In certain embodiments the EXO-Code sequence does not include the sequence: ACCCUGCCGC-CUGGACUCCGCCUGU (SEQ ID NO:3). In certain embodiments the EXO-Code sequence does not include a GGAG motif.

In order for EXO-Code containing polynucleotides to exert their function they are introduced into exosomes or other membranous structures using any of a variety of approaches. In embodiments EXO-Code containing polynucleotides are introduced into exosomes via cellular processing. Thus, EXO-Code containing polynucleotides can be introduced into cells which incorporate the EXO-Code containing polynucleotides into exosomes in the native cellular environment and exosome processing machinery, or they are introduced into an individual, such that they enter cells into the individual and are subsequently incorporated into exosomes. The EXO-Code containing polynucleotides are introduced into cells by using any suitable technique, examples of which include but are not limited to electroporation, incubation, cell activation, and transfection, lipid transfection, lipid delivery, liposomal delivery, polymer transfection, polymeric delivery, through peptide delivery (i.e. but not limited to cationic peptides, amphiphilic peptides, cell penetrating peptides), calcium or magnesium precipitation, and ion precipitation (also known as DNA-calcium phosphate precipitation). The disclosure thus includes in vitro cell cultures comprising one or more EXO-Code containing polynucleotides and one or more reagents that facilitate entry of the EXO-Code containing polynucleotides into the cells. The disclosure includes transcription templates encoding the EXO-Code containing polynucleotides, such as expression vectors configured to express the EXO-Code containing polynucleotides. Polynucleotides comprising EXO-Codes can be introduced directly into exosomes or other vesicular structures as described herein by using any suitable techniques, examples of which include but are not limited to electroporation, incubation, cell activation, and transfection, lipid transfection, lipid delivery, liposomal delivery, polymer transfection, polymeric delivery, through peptide delivery (i.e. but not limited to cationic peptides, amphiphilic peptides, cell penetrating peptides), calcium or magnesium precipitation, and ion precipitation (also known as DNA-calcium phosphate precipitation).

The disclosure includes compositions, including but not limited to pharmaceutical compositions suitable for human and/or veterinary uses, wherein the compositions comprise EXO-Code containing polynucleotides. Pharmaceutical compositions generally comprise at least one pharmaceutically acceptable excipient, carrier, diluent, and the like. The disclosure includes cell cultures modified to produce exosomes that contain the EXO-Code containing polynucleotides, cell culture medium comprising the exosomes, as well as isolated and/or purified exosome populations, wherein at least some of the exosomes in the population comprise EXO-Code containing polynucleotides. The disclosure includes pharmaceutical compositions comprising exosomes that contain EXO-Code containing polynucleotides. The disclosure includes methods of making the EXO-Code containing polynucleotides, such as by chemical synthesis, or in vitro or in vivo transcription. Also included are combinations of distinct polynucleotides comprising EXO-Codes wherein the combination has a greater than additive or synergistic effect on at least one EXO-Code/exosome sorting property and/or effect on a cell into which a modified exosome of this disclosure is introduced. Polynucleotides of this disclosure can comprise one, or more than one EXO-Code sequence, and can comprise more than one of the same EXO-Code sequence, or distinct EXO-Code sequences. In more detail, multivalency is a well-established approach in engineering higher affinity interactions between two moieties. An essentially unlimited number of EXO-Codes and combinations of distinct EXO-Codes could be incorporated into any single polynucleotide for the potential to achieve enhanced exosomal delivery. However, there may be an inverse relationship between increased affinity and size of the polynucleotide as more EXO-Codes are incorporated. Thus, in non-limiting embodiments, polynucleotides of this disclosure comprise 1, 2, 3, or more EXO-Codes. Further, although an advantage of EXO-Codes is realized when electroporated directly into living cells for active exosomal packaging, in applications where this is infeasible, direct exosome loading may be used. For the purposes of in vivo delivery the EXO-Codes could be loaded directly into isolated patient-derived exosomes via well-established electroporation protocols. They may also be incorporated into any synthetic lipidic delivery vehicle such as liposomes, cationic lipoplexes, other polymeric delivery vehicles or any host of delivery vehicle capable of delivering the EXO-Codes to the cytoplasm of recipient cells. These cells could then package the EXO-Codes into exosomes for in vivo exosome programming, or for other purposes. In embodiments, cells that secrete exosomes described herein may be in vitro cell compositions, such as eukaryotic cells of any origin, eukaryotic cell lines, and the like.

Polynucleotides comprising the EXO-Codes may be introduced into an individual using any suitable technique method and approach. Polynucleotides comprising the EXO-Codes may be introduced into an individual as modified or unmodified RNA, or by using for example a recombinant viral vector that can express the polynucleotides, including but not necessarily limited to lentiviral vectors, adenovirus vectors, and adeno associated viral vectors. In certain approaches polynucleotides comprising the EXO-Codes are introduced to an individual as a component of one or more cells, which may be autologous cells or heterologous cells, including but not necessarily limited to stem cells of a wide variety of types and stages of development. In an embodiment a composition comprising a polynucleotide comprising an EXO-Code or a polynucleotide encoding such EXO-Code is introduced to an individual in need thereof. In embodiments the individual is in need of prophylaxis and/or therapy for one or more cancers, neurodegenerative disorders, autoimmune disorders, or any other disorder wherein a reprogrammed exosome may be of therapeutic or prophylactic benefit to the individual. In embodiments an effective amount of polynucleotide comprising an EXO-Code is administered to or expressed in the individual such that the expression of at least one RNA is inhibited or eliminated or an expressed RNA, such as an mRNA, is degraded, or translation of an mRNA is inhibited. In embodiments such administration results in an improvement in one or more symptoms of a disease or disorder in the individual. In certain aspects compositions and methods of the disclosure are used to inhibit metastasis, such as by reprogramming cancer cell-derived exosomes to reduce or eliminate their capability to convert healthy cells into tumor-forming cells in their immediate microenvironment, and/or to reduce or eliminate transfer of oncogenic factors, such as oncogenic small RNAs, to recipient cells. In other certain aspects compositions and methods of the disclosure are used in connection with tissue regeneration, such as in the context of wound healing, including but not necessarily limited to wounds that are incurred during medical procedures, and wounds incurred outside of a medical setting, including but not limited to tissue or bone trauma incurred for any non-medical reason. Thus, in embodiments the disclosure is pertinent to, for example, emergency and non-emergency medical care. In embodiments the disclosure is pertinent to promoting angiogenesis, such as in any case where angiogenesis would be a desirable component of wound healing.

Those skilled in the art will recognize how to separate modified exosomes made according to this disclosure. In general exosomes are collected from a cellular supernatant and can be isolated by differential centrifugation or density centrifugation according to well-known protocols. Exosomes comprising polynucleotides can be separated from those that do not comprise polynucleotides and subpopulations of exosomes can be obtained. EXO-Code containing polynucleotides can be isolated from the exosomes using standard approaches. Sequences of the EXO-Codes can be determined using standard approaches including but not necessarily limited to making and amplifying cDNA and determining the cDNA sequence using known sequencing techniques and apparatus, including but not limited to high throughput approaches. The disclosure thus includes methods of making, screening, and identifying EXO-Code sequences as described further herein. In general, methods for identifying EXO codes comprise subjecting a plurality of EXO-Codes having distinct sequences to a native intracellular environment which harnesses the endogenous cellular trafficking machinery to sort the EXO-Codes to exosomes. This approach is termed POSTAL: Procedure for Organelle-Specific Targeting by Aptamer Libraries. By chemically synthesizing RNA sequences of high diversity, we introduce sequences that have the potential to outperform natural miRNA and mRNA in their ability to sort to exosomes. Thus, this method has the potential to select for sequences that show improved exosomal enrichment when compared to existing approaches that look for motifs only within endogenous miRNAs. In certain embodiments EXO-Code containing polynucleotides of this disclosure show preferential enrichment in exosomes relative to naturally occurring RNA polynucleotides that are endogenously sorted to exosomes. In certain embodiments EXO-Code containing polynucleotides of this disclosure exhibit at least 2-1000 fold enrichment, inclusive, and including all integers and ranges of integers there between. The enrichment in exosomes may be determined by comparison to a value obtained from determining enrichment using a wild type or endogenously occurring sequence.

The disclosure includes kits for making, screening, and using EXO-Codes and polynucleotides comprising them for a wide variety of research, therapeutic and prophylactic approaches that will be apparent to those skilled in the art given the benefit of the present disclosure. The kits may comprise reagents for making and screening exosomes and may include EXO-Code containing polynucleotides and may contain reagents useful for introducing such polynucleotides into cells.

In one aspect the disclosure includes a plurality, ensemble library, etc. that includes at least two distinct polynucleotides which comprise a distinct EXO-Code sequences that are described herein. Thus the library may contain between 2 and 1000 distinct EXO-Code sequences. Accordingly, the disclosure includes a library comprising between 2 and 10000 distinct EXO-Code sequences wherein at least one of the EXO-Code sequences is described herein.

In one approach the disclosure comprises selecting a cell or cell type for modification by contacting it with a modified exosome of this disclosure. The method generally comprises mixing a cellular composition with the modified exosomes such that the exosomes are taken up by the cells and the modified polynucleotide that comprises the EXO-Code and any particular cargo with which the polynucleotide has been modified is released into the cytoplasm. Subsequently the modified polynucleotide that comprises the EXO-Code may exert its effect in the target cell. These approaches can be used in vitro and are expected to be suitable for use in vivo. Thus, the disclosure includes selecting an individual in need of modification and/or reprogramming of exosomes, and administering to the individual an EXO-Code containing polynucleotide that is encompassed herein.

The following examples are provided to illustrate certain embodiments of the invention, but are not intended to be limiting in any way.

Example 1

FIG. 1 provides a non-limiting illustration of the use of EXO-Code containing polynucleotides to reprogram exosomes released from cancer cells, thereby halting disease progression. (A) Tumor-secreted exosomes have been shown to prepare metastatic niches in distant organs. (B) Schematic depicting EXO-Codes conjugated to a therapeutic cargo to reprogram tumor-derived exosomes to halt disease progression.

Figure 2:
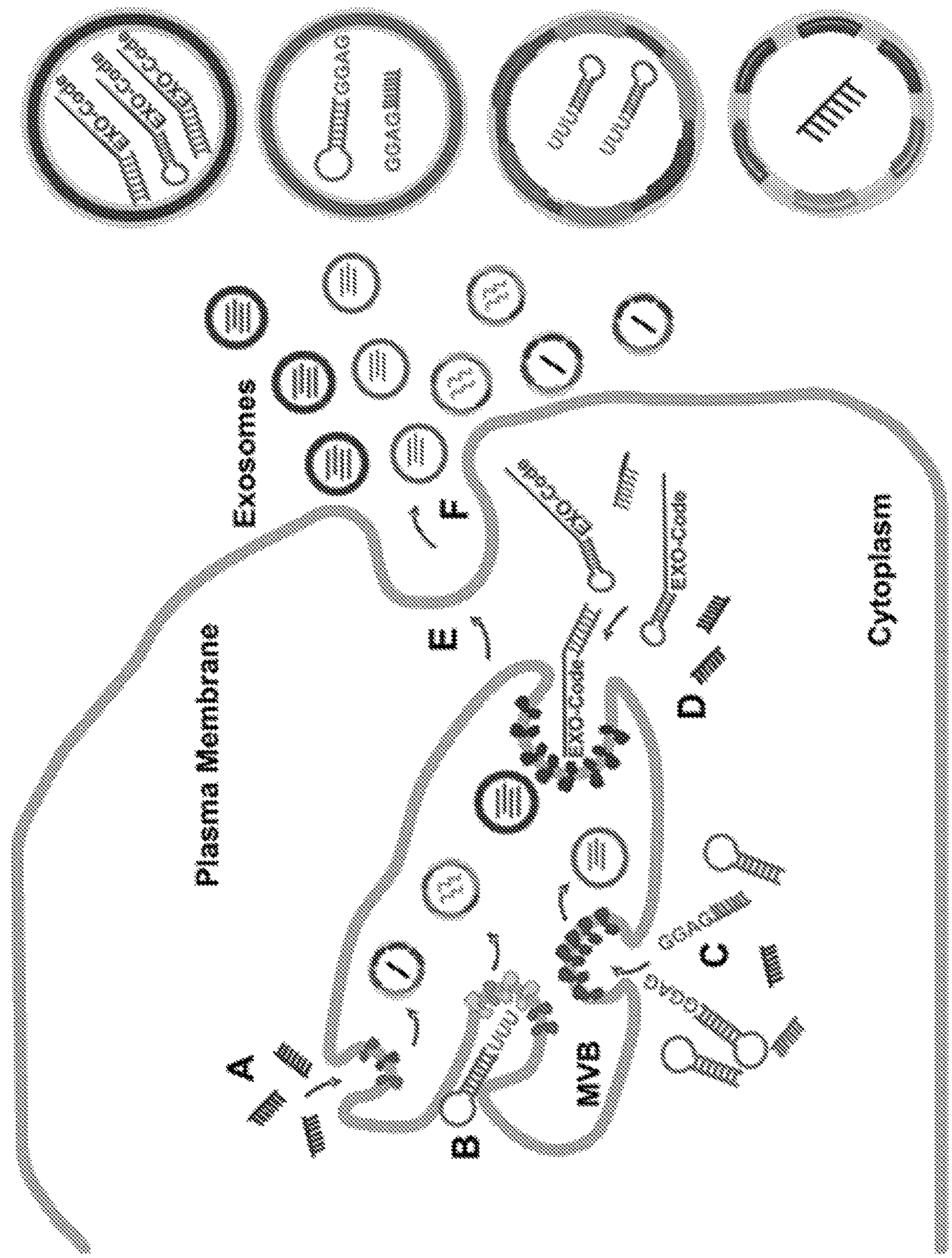
FIG. 2 provides a schematic illustrating the harnessing of exosomal biogenesis to identify biomimetic EXO-Codes that are specifically enriched in exosomes. During exosome biogenesis, non-coding RNA/mRNA can be loaded into exosomes during inward budding of the MVB membrane. The loading of nucleic acids can occur via: (A) a passive mechanism, and (B)/(C)/(D) via active sorting mechanisms through sequence-specific sequences. (E&F) Exosomes are released into the extracellular milieu through fusion with the cell membrane. (D) We adapted this process to identify EXO-Codes described herein.

FIG. 2 provides a schematic illustrating the harnessing of exosomal biogenesis to identify biomimetic EXO-Codes that are specifically enriched in exosomes. During exosome biogenesis, non-coding RNA/mRNA can be loaded into exosomes during inward budding of the MVB membrane. The loading of nucleic acids can occur via: (A) a passive mechanism, and (B)/(C)/(D) via active sorting mechanisms through sequence-specific sequences. (E&F) Exosomes are released into the extracellular milieu through fusion with the cell membrane. (D). We adapted this process to identify EXO-Codes described herein.

Figure 3:
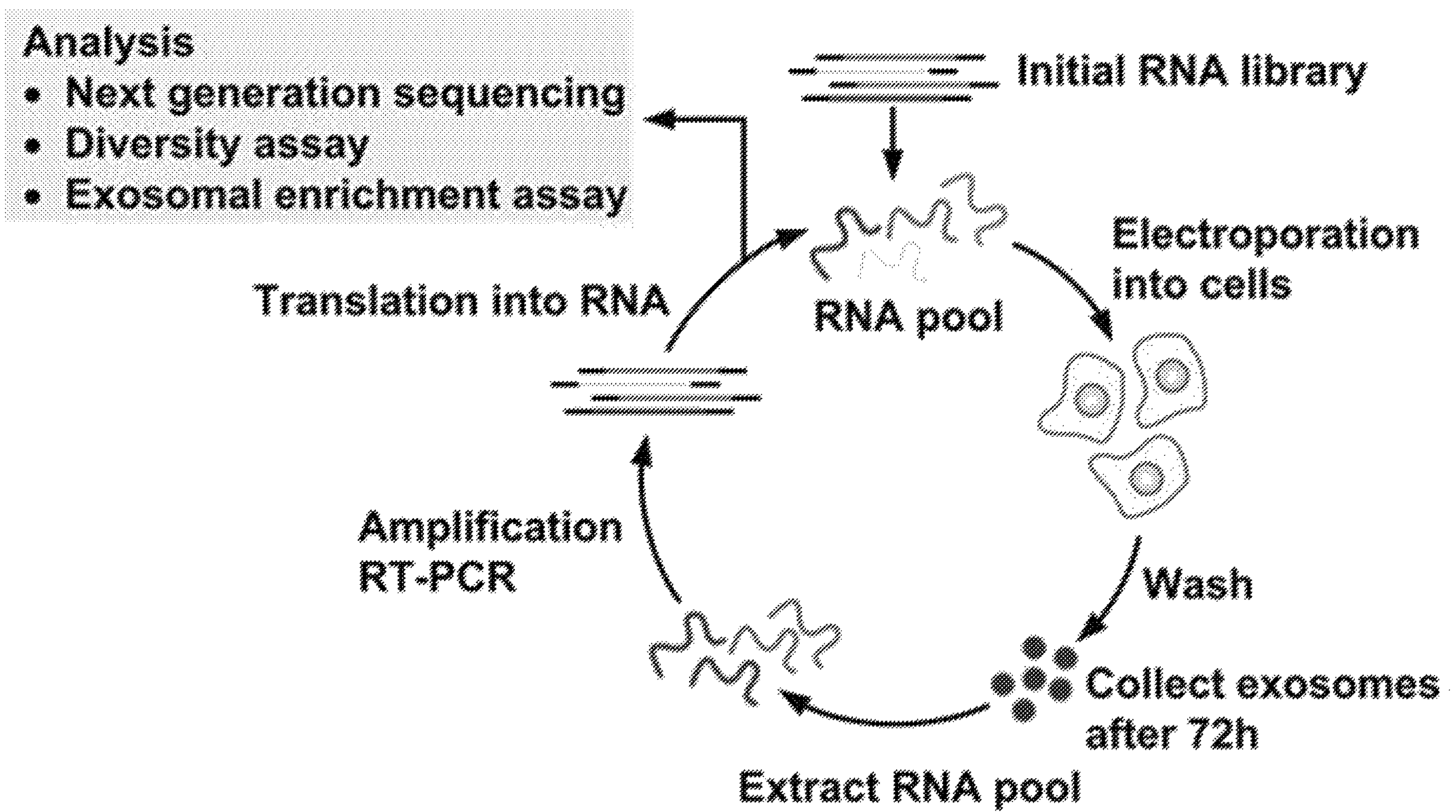
FIG. 3 provides a schematic of an RNA library screening approach used to identify EXO-Codes of this disclosure. Cells are electroporated with a large pool of RNA sequences ($10^{12}$ diversity). Exosomes are collected and the RNA sequences extracted. After conversion into cDNA, PCR amplified DNA is transcribed into RNA to create the RNA pool used for the next rounds of selection. Selection rounds are repeated 6 to 10 times with increased selection pressure (by reducing the amount of input RNA). Illumina next-generation sequencing has been performed for selection rounds 3 to 10 in MDA-MB-231 cells, PC-3 cells, HEK293 cells, mesenchymal stem cells, and Raw 264.7 cells.

FIG. 3 provides a schematic of an RNA library screening approach used to identify EXO-Codes of this disclosure. Cells are electroporated with a large pool of RNA sequences ($10^{12}$ diversity). Exosomes are collected and the RNA sequences extracted. After conversion into cDNA, PCR amplified DNA is transcribed into RNA to create the RNA pool used for the next rounds of selection. Selection rounds are repeated 10 times with increased selection pressure (by reducing the amount of input RNA). Illumina next-generation sequencing has been performed for selection rounds 3 to 10 in MDA-MB-231 cells, PC-3 cells, HEK293 cells, mesenchymal stem cells, and Raw 264.7 cells.

Figure 4:
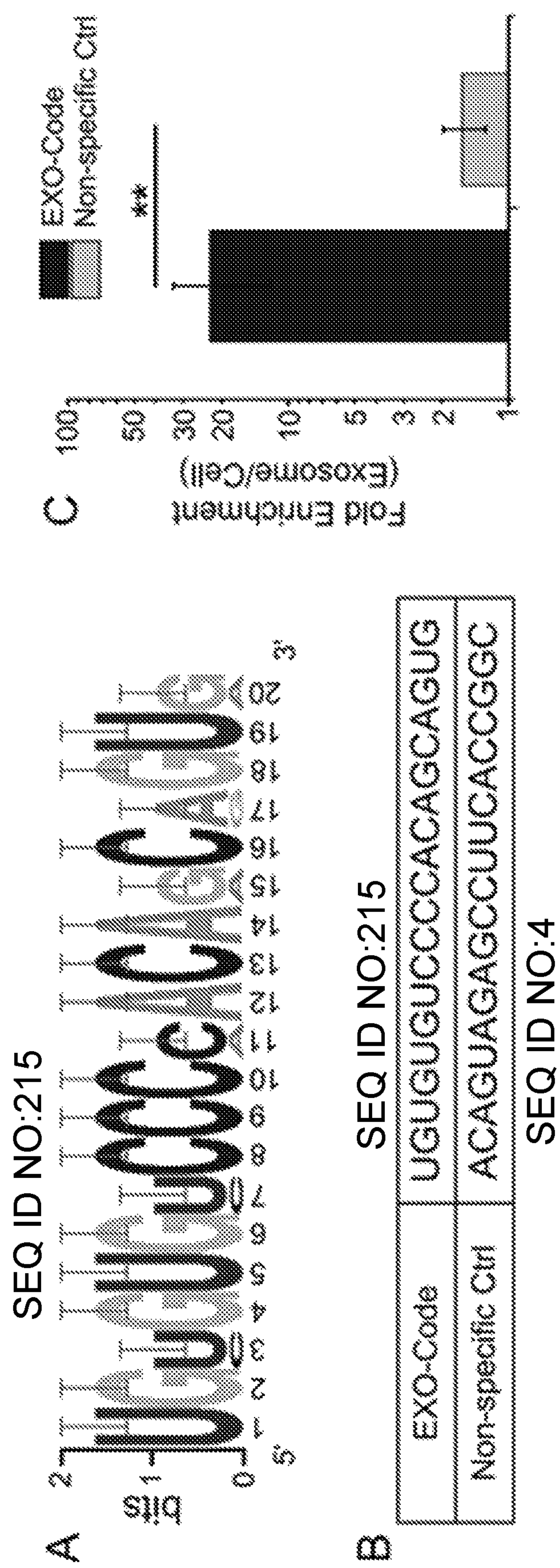
FIG. 4 shows an illustrative proof-of-concept example of using methods of this disclosure to identify EXO-Code sequences. (A) The EXO-Code motif was identified after three rounds of selection. E-value: 9.5e-018, (B) For the non-specific control, point mutations were introduced into the EXO-Code at highly conserved positions. (C) This resulted in almost a complete ablation of exosomal enrichment and strongly indicates the specificity of our novel EXO-Code. Data are mean±sd. **$P<0.01$ by two-tailed Student's t-test.

An illustrative proof-of-concept example of using methods of this disclosure to identify EXO-Code sequences in presented in FIG. 4. We screened an RNA library in the metastatic MDA-MB-231 breast cancer cell line which resulted in the identification of EXO-Code candidates. In particular, a large RNA library ($10^{12}$ diversity of species with a central 20-base random domain flanked by two PCR primer sites) was introduced into MDA-MB-231 cells by electroporation. To allow RNAs to sort to exosomes, cells were grown for 48-72 h before collecting secreted exosomes. Enriched RNA sequences were extracted from exosomes and subjected to two additional rounds of selection. To increase selection pressure, the amount of input RNA was decreased from 50 μg to 10 μg RNA over several rounds of selection. Enriched RNA EXO-Code reads were analyzed by next-generation sequencing (Illumina MiSeq2000, Genomics and Bioinformatics Core, University at Buffalo). Three rounds of selection allowed identification of a representative and non-limiting EXO-Code as depicted in FIG. 4. As can be seen in FIG. 4, an EXO-Code motif was identified after three rounds of selection. E-value: 9.5e-018, (B) For the non-specific control, point mutations were introduced into the EXO-Code at highly conserved positions. (C) This resulted in almost a complete ablation of exosomal enrichment and strongly indicates the specificity of our novel EXO-Code. Data are mean±sd. **P<0.01 by two-tailed Student's t-test.

When introduced into MDA-MB-231 cells, EXO-Code depicted in FIG. 4 showed 22-fold enrichment in exosomes over bulk cell lysates. To assess specificity for exosomal enrichment, point mutations were introduced into the EXO-Code, which resulted in a non-specific control ACAGUAGAGCCUUCACCGGC (SEQ ID NO:4)) that showed only background enrichment in exosomes (~1.25-fold enrichment exosome/cell ratio). Thus, the data indicate this EXO-Code is highly specific for exosomes. We next performed additional rounds of selection and identified further RNA sequences enriched in exosomes. Selection rounds 3, 5, 7, and 10 have been analyzed for MDA-MB-231 cells. The 15 most highly represented sequences after ten rounds of selection are shown in FIG. 5B. The wide range of exosomal enrichment of these sequences (anywhere from 185 to 806-fold) provides a basis for elucidating structure-activity relationships.

Figure 6:
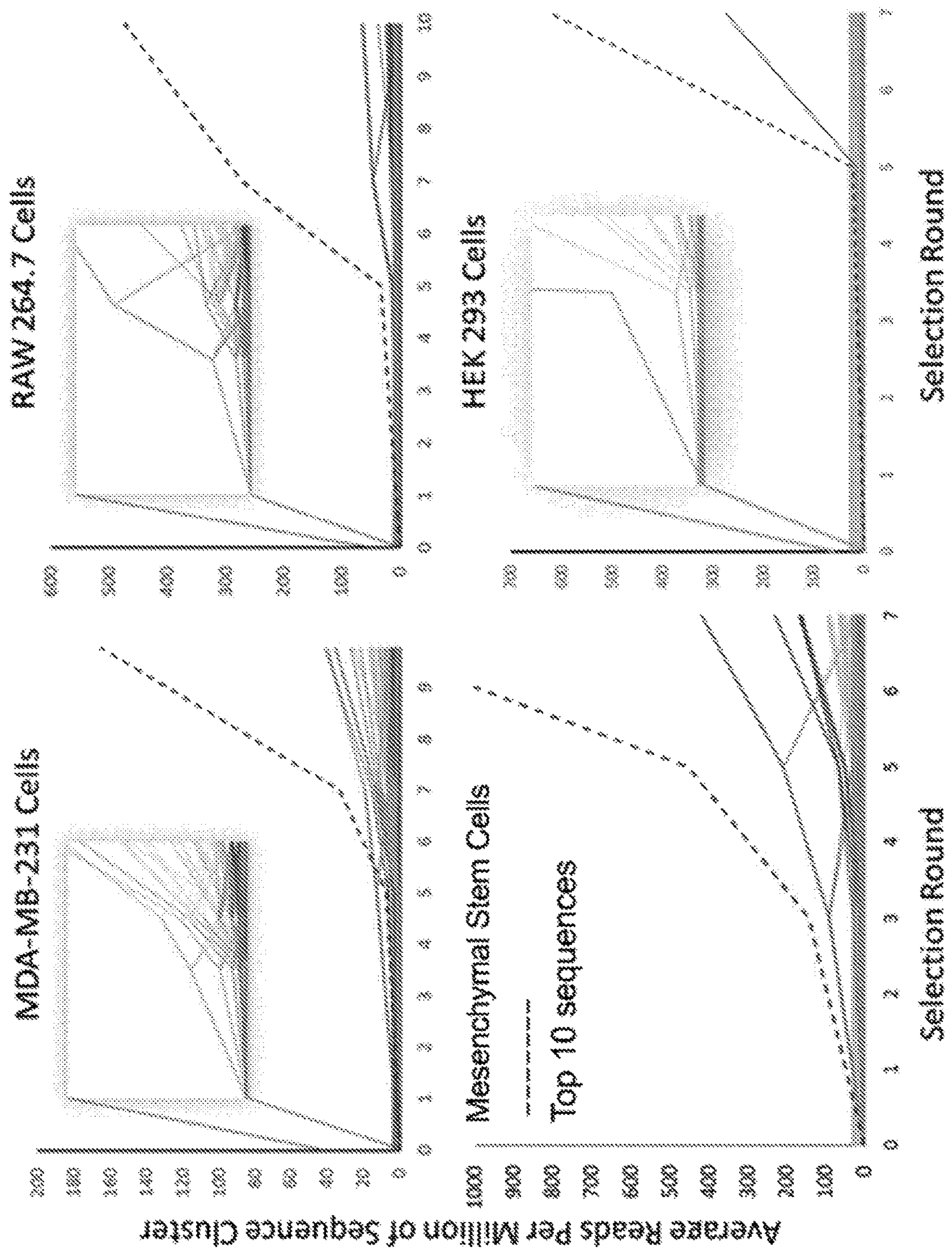
FIG. 6 shows enrichment of the RNA sequences after several rounds of selection in MDA-MB-231 cells, Raw 264.7 cells, mesenchymal stem cells, and HEK 293 cells. Reads per million of each sequence present in selection round 3, 5, 7, and/or 10 were analyzed.

As can be seen in FIG. 5(A) the diversity of the RNA library decreases with each round of selection. This shows that our selection procedure leads to enrichment of specific sequences. 5(B) Top 15 enriched EXO-Codes after 10 rounds of selection in MDA-MB-231 cells. After 10 rounds of selection we were able to identify additional sequences that could function as EXO-Codes. FIG. 6 shows enrichment of the RNA sequences after several rounds of selection in MDA-MB-231 cells, Raw 264.7 cells, mesenchymal stem cells, and HEK 293 cells. Reads per million of each sequence present in selection round 3, 5, 7, and/or 10 were analyzed. Using descriptive statistics for the enrichment distribution, 6 levels of enrichment were set based on standard deviation with the lowest level encompassing up to one standard deviation above the mean RPM and the highest level of enrichment was reserved for the most enriched sequences falling above 32σ above the mean. This binning approach was used for the earliest sequenced selection round and the average RPM for each cluster was plotted. Each cluster was then plotted to those levels for the subsequent selection rounds allowing for branching off into further enriched or sometimes depleted fractions of sequences. Examining the sequence enrichment trajectories in this way through selection rounds demonstrated that a majority of sequences do not become significantly enriched or selected for. Conversely, for the top 10 sequences that were vetted as potential EXO-Codes there is a significant and continued enrichment compared to background reads.

Our protocols to identify exosome-enriched sequences include rounds of selection that result in unbiased and relevant pool enrichment. Optimized delivery of a large and diverse RNA library ($10^{12}$ diversity) into MDA-MB-231 cells, HEK 293 cells, MSCs, Raw 264.7 cells, and other cell types by electroporation, resulting in RNA library delivery into the cytoplasm where sequences are sorted to exosomes. The library contains single stranded RNA sequences that are 20 nucleotide bases in length, flanked by two constant regions for reverse transcription and PCR amplification (TriLink Biotechnologies). Exosomes can be collected after 24 h to 72 h of culture. RNA is extracted from the exosomes using the QIAzol lysis reagent, reverse transcribed, and PCR amplified with the following primers: FP 5'-TTCAGG TAATACGACTCACTATAGGGAAGAGA-AGGACATATGAT-3' (SEQ ID NO:5) and RP 5'-TCAAGTGGT- CATGTAC-TAGTCAA-3' (SEQ ID NO:6). A T7 promoter is incorporated into the forward primer to allow transcription into RNA. Correctly sized PCR products are isolated and transcribed into RNA using a cell-free transcription system (Megashortscript T7 from Ambion).

High-throughput RNA sequencing and analysis. For Illumina MiSeq sequencing, RNA sequences from selection rounds 3, 5, 7, and 10 are reverse transcribed using reverse transcriptase and Illumina amplicon primers containing adapter ligation and gene-specific primer sequences for our RNA library. The following forward and reverse primers were used: FP5'-TCGTCGGCAGCGTCAGATGTGTAT AAGAGACAGTAGGGAAGAGAAGGACATATGA T-3' (SEQ ID NO:7) and RP5'-GTCTCGTGGGCTCGGAG ATGTGTATAAGAGACAGTCAGTGGTCATG-TACTA-GTCAA-3' (SEQ ID NO:8). The resulting product is amplified using a limited number of PCR cycles to avoid library overamplification and potential bias. The PCR products (each sequence containing an adapter ligation for annealing to the chip) are then sequenced. As was done for the MDA-MB-231 cells, newly generated data is analyzed with 'Fastaptamer': after trimming adapter sequences and PCR primer sites and eliminating incorrect length reads. A decrease in the number of unique reads and an increase in the number of sequences showing multiple reads at each selection round is obtained, strongly indicating enrichment of exosome-specific sequences (FIG. 5A).

Assessing the enrichment of EXO-Codes in exosomes and determining enrichment kinetics. The EXO-Codes of FIG. 5B and others described herein can be assessed for exosomal enrichment as is shown for the lead EXO-Code in FIG. 4. Briefly, enrichment of the newly identified EXO-Codes is determined using a modified stem-loop RT-PCR protocol. First, the stem-loop RT primer is hybridized to the 3' portion of the RNA species present in the cell before reverse transcription of exosomal lysates (Applied Biosystems). The RT product will be quantified by TaqMan real-time PCR. Further, exosomal sorting kinetics for all identified EXO-Codes are quantified. EXO-Codes are transfected into the relevant cell line and exosomes are collected at 6 h, 12 h, 18 h, 24 h, 48 h, 60 h, and 72 h post administration. The exosomal EXO-Codes are quantified by RT-PCR and the sorting kinetics calculated to determine the structure-activity relationship of the sequences.

Competitive sorting assay. In an approach the five most highly enriched EXO-Codes for each cell line are subjected to a competitive exosomal sorting assay. After electroporation of all five sequences into each cell line, analysis is made to determine if the sequences can simultaneously be sorted to exosomes and if any show preferred and/or faster sorting to exosomes.

The present disclosure includes what is believed to be the first attempt to systematically compile and analyze published data on exosomally-enriched miRNAs to identify the conserved motifs responsible for active sorting. To identify exosomally-enriched motifs in naturally occurring sequences, we performed a retrospective in silico analysis of miRNA data from publications reporting the relative abundance of miRNAs in cells and exosomes. Only miRNAs that were enriched in exosomes compared to whole cell lysates were chosen for further examination. This resulted in a total of 253 miRNA sequences. Sequences were analyzed using MEME motif finder suite with a zero-order Markov background model and a zero-or-none assumption for the number of motifs per sequence and a motif length confined to between 4 and 12 nucleotides. This resulted in 3 statistically significant motifs (FIG. 7). The global motif A had an E-value of 1.0e-9, motif B 4.0e-5, and C 2.4e-4.

EXO-Codes that show significant exosomal enrichment. The present disclosure includes but is not limited to EXO-Code sequences generated from both experimental and in silico analyses (FIGS. 5, 6 & 7). The structure-activity relationship of these sequences and their ability to mediate sorting can be established.

Without intending to be constrained by any particular theory it is considered that exosomal sorting of EXO-Codes is regulated by interactions with cellular proteins and their expression levels. EXO-Codes of this disclosure can take into account such interactions. In particular, our analysis using the RNA-Binding Proteins Map (RBPmap) and SYBYL in silico docking indicates that one EXO-Code sequence identified above is likely to bind to HnRNP L and G3BP1, both of which are present in the exosomes of MDA-MB-231 cells. HnRNP (heterogeneous nuclear ribonucleoprotein) proteins are an important family of RNA-binding proteins that have long been known to be key players in RNA biogenesis and expression, cytoplasmic export, and mRNA translation. Data suggests that they have a broader function in miRNA regulation and decay. Specifically, HnRNP L has been shown to regulate the tumorigenic capacity of various cancer cells and may, therefore, itself be oncogenic. Strikingly, HnRNP L is a protein that is present in cancer exosomes. Based on in silico predictions, the motif "CCCCACA" within our EXO-Code sequence(s) described herein exhibits low nanomolar affinity, whereas the motif "CACAGCA" may bind in the high nanomolar range. A model protein-RNA crystal structure for HnRNP L was used (RCSB PDB ID: 2MQO). The native RNA species (CACACA) was used to generate a protomol docking area and was then mutated to address any sequence variations. When solving for 20 poses and selecting the best pose as the highest 'Total Score' with a 'Consensus Score' of at least 4, a rank order of binding for the 8 RNAs was obtained. The normalized in silico docking score was correlated with experimentally determined binding affinities pulled from known references. This revealed a strong log-log relationship ($r^2$=0.82) as shown in FIG. 8B. Nucleotide mutations within the 'CACA' motif decrease the binding affinity to HnRNP L, as shown in FIG. 8A. FIG. 8A is an in-silico demonstration that is not meant to be limiting. In particular, FIGS. 8 (A&B) show normalized in silico dock score, which show high correlation (R2=0.82) with experimentally determined binding affinities of RNA sequences to HnRNP L (circles). The sequences within the EXO-Codes bind to HnRNP L with predicted binding affinities of 3.23 nM (CCCCACA) and 223.2 nM (CACAGCA). (C) Surface rendered presentation of CCCCACA (white) binding to the RNA-recognition motif (RRM) of HNRNP L. (D) Calculated electrostatic surface potential shows the interactions of CCCCACA with HnRNP L (anionic charges and cationic charges shown). (E) The main binding motif to HnRNP L as predicted by in silico docking is "CACA". Prefacing "CACA" with "CCC" as can be found in our motif (CCCCACA) did not seem to induce steric hindrances since the in silico dock score still ranked the motif in the low nanomolar range. The binding of CCCCCACA to HnRNP L is mediated by intermolecular hydrogen bonds (dashed lines). The binding is further stabilized by electrostatic interactions between C4 and Arg102 and by stacking interactions between A5 and Tyr168. The data are is consistent with binding of HnRNP L to CA-repeats (e.g., CACACA) or repeats separated by spacers such as CANRCA and CANRCA. Specifically, as depicted in FIG. 8 E, the binding of "CCCCACA" within our one of the EXO-Codes described herein to HnRNP L is mediated by intermolecular hydrogen bonds shown as yellow dashed lines (A5/Pro190, C6/Tyr168/Thr170/Ser169, A7/Ser175). The binding is further stabilized by electrostatic interactions between the C4 phosphate group and Arg102 and by stacking interactions between A5 and Tyr168. Furthermore, based on its sequence, the lead EXO-Code UGUGUGCCCCACAGCAGUG (SEQ ID NO:9) would be predicted to bind to G3BP1 via CCCACAGCAG (SEQ ID NO:10). Similar to HnRNP L, G3BP1 (GTPase activating protein (SH3 domain) binding protein 1) belongs to a family of RNA-binding proteins. G3BP1 plays an important role in the proliferation of MDA-MB-231 and other breast cancer cell lines.

Complementary to in silico predictions, the disclosure includes experimentally determinations of novel EXO-Code-binding proteins using pull-down assays and mass spectrometry. Once the bound proteins have been identified, in silico docking analysis is performed to predict and analyze RNA-motifs binding to the identified proteins and elucidate structure-activity relationships of the EXO-Codes and their protein partners. We have successfully shown that our in silico approach can correctly predict the rank-order binding affinity of the RNA-motifs to HnRNP L (FIG. 8). The normalized in silico "Dock Score" (a measure of binding affinity) generated using SYBYL shows a strong correlation with experimentally determined binding affinities.

TABLE 1

| Rank | MDA-MB-231 Cells (Rd10) Sequence 5'→3' | Mesenchymal Stem Cells (Rd7) Sequence 5'→3' | RAW 264.7 Cells (Rd10) Sequence 5'→3' | HEK 293 Cells (Rd7) Sequence 5'→3' |
|---|---|---|---|---|
| 1 | UCGUAGGUCAGGAAGCGGCG (SEQ ID NO: 11) | UGGAACGUCGAUGUGGGCCG (SEQ ID NO: 21) | GAUGGUAAGUUGGAAAGCGA (SEQ ID NO: 31) | UGAUGUAUUGGUAAGUUUCG (SEQ ID NO: 41) |
| 2 | GCGAUAGGCGGUCGUUGGUC (SEQ ID NO: 12) | GGUUCAGGGUGUGGGCCGCC (SEQ ID NO: 22) | UGGAACGUCGAUGUGGGCCG (SEQ ID NO: 32) | UAUAGAUGUGCUAGUUUGCA (SEQ ID NO: 42) |
| 3 | CCCGCUUCUUCCUCGGGUGG (SEQ ID NO: 13) | UCGUAGGUCAGGAAGCGGCG (SEQ ID NO: 23) | GAUGGUAUGUUGGAAAGCGA (SEQ ID NO: 33) | UUUCGUGUUUAGCGUUUGAC (SEQ ID NO: 43) |
| 4 | GUCACUCGGCCUAGUGCGUC (SEQ ID NO: 14) | AAGGCCGGUGCUAGUAGUGA (SEQ ID NO: 24) | CGUGGCUGGUUCGUGCGGGG (SEQ ID NO: 34) | UGAUGUAUUUGGUUUGCAAG (SEQ ID NO: 44) |
| 5 | CCUGACCUUACUCGGGUGGC (SEQ ID NO: 15) | GCGAUAGGCGGUCGUUGGUC (SEQ ID NO: 25) | UUCGUGUAUCUAGUGCAGUC (SEQ ID NO: 35) | ACGUGUAUUACUAUUGACUA (SEQ ID NO: 45) |
| 6 | GUGGUCGAUAAGCGUACGCG (SEQ ID NO: 16) | GCUGGUCAGGAUGCGGGGGC (SEQ ID NO: 26) | GGUCGAGUGAUGCGGGGCGC (SEQ ID NO: 36) | GAGGCCUGUGCUAGUAGUGA (SEQ ID NO: 46) |
| 7 | AGGGCGUUUGCUCGCGGGUC (SEQ ID NO: 17) | GCUGCGAAGUGGGGCAGGUC (SEQ ID NO: 27) | UUUCGUGUAUCCUAGUUGCU (SEQ ID NO: 37) | UUAGCGUUGUAUUAGUUGCA (SEQ ID NO: 47) |
| 8 | CCGGGCGUAUCUUGUGGUCG (SEQ ID NO: 18) | GGUCGAGUGAUGCGGGGCGC (SEQ ID NO: 28) | UGAUGUAUUUGGUUUGCAAG (SEQ ID NO: 38) | UCAUUGUGCUGAAUUGACUA (SEQ ID NO: 48) |
| 9 | CAGACGGUACUCAGGUGUGC (SEQ ID NO: 19) | CGUGGCUGGUUCGUGCGGGG (SEQ ID NO: 29) | UUCGUGUUCUGGUUGAGUGU (SEQ ID NO: 39) | AAUUACACUGUGCUAGGAUG (SEQ ID NO: 49) |
| 10 | GGCCUUGGUCGCGUGCUGGC (SEQ ID NO: 20) | GGGCGAAAUUGGCAUGGCCG (SEQ ID NO: 30) | GCGCGGGAAGGGUGGCAUGG (SEQ ID NO: 40) | AUCGAUGUAUGAGUCAUAUA (SEQ ID NO: 50) |

Figure 9:
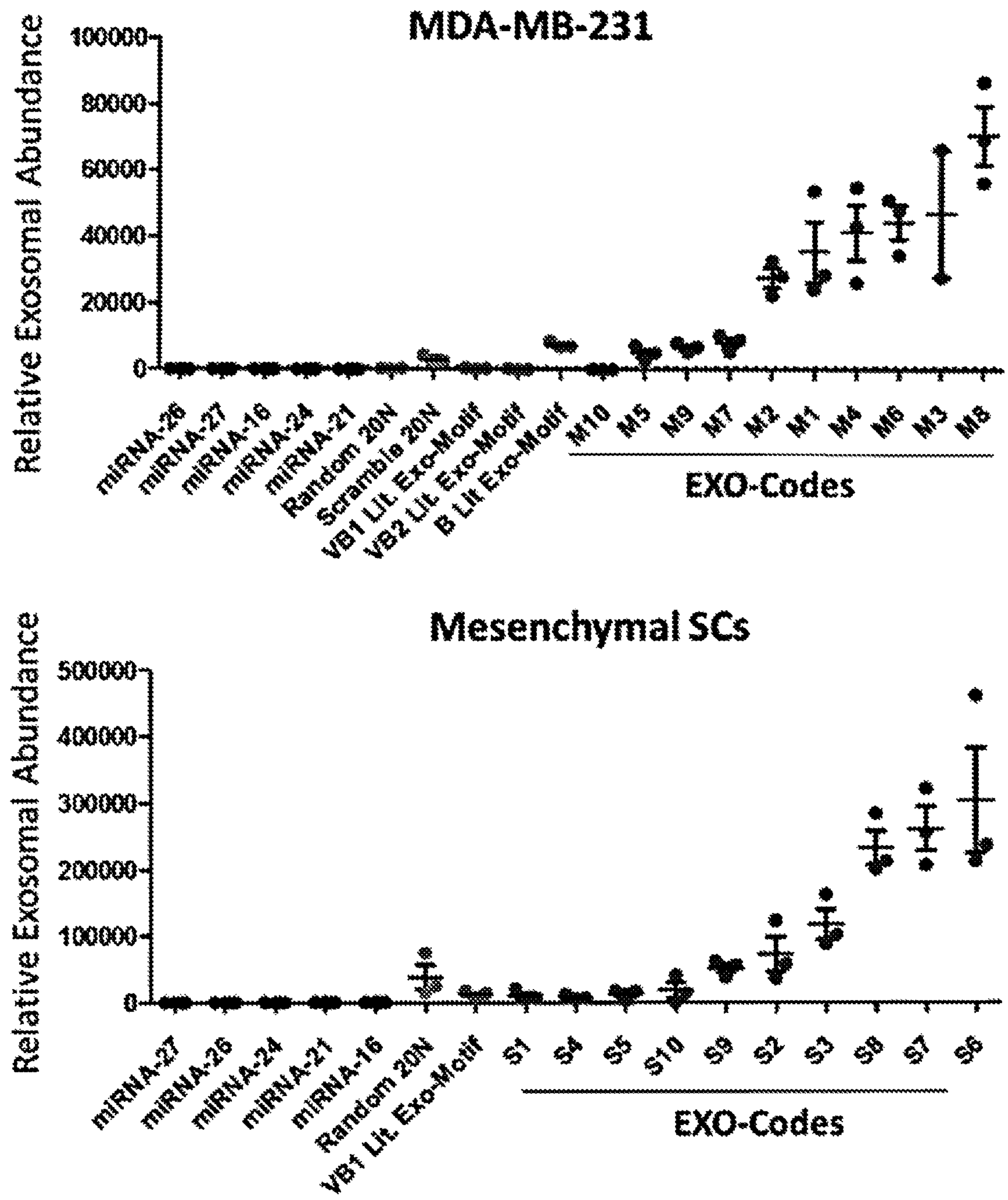
FIG. 9 shows relative exosomal enrichment of EXO-Codes after electroporation into their parent cell lines (MDA-MB-231 cells, mesenchymal stem cells, Raw 264.7 cells, and HEK 293 cells).
Figure 9:
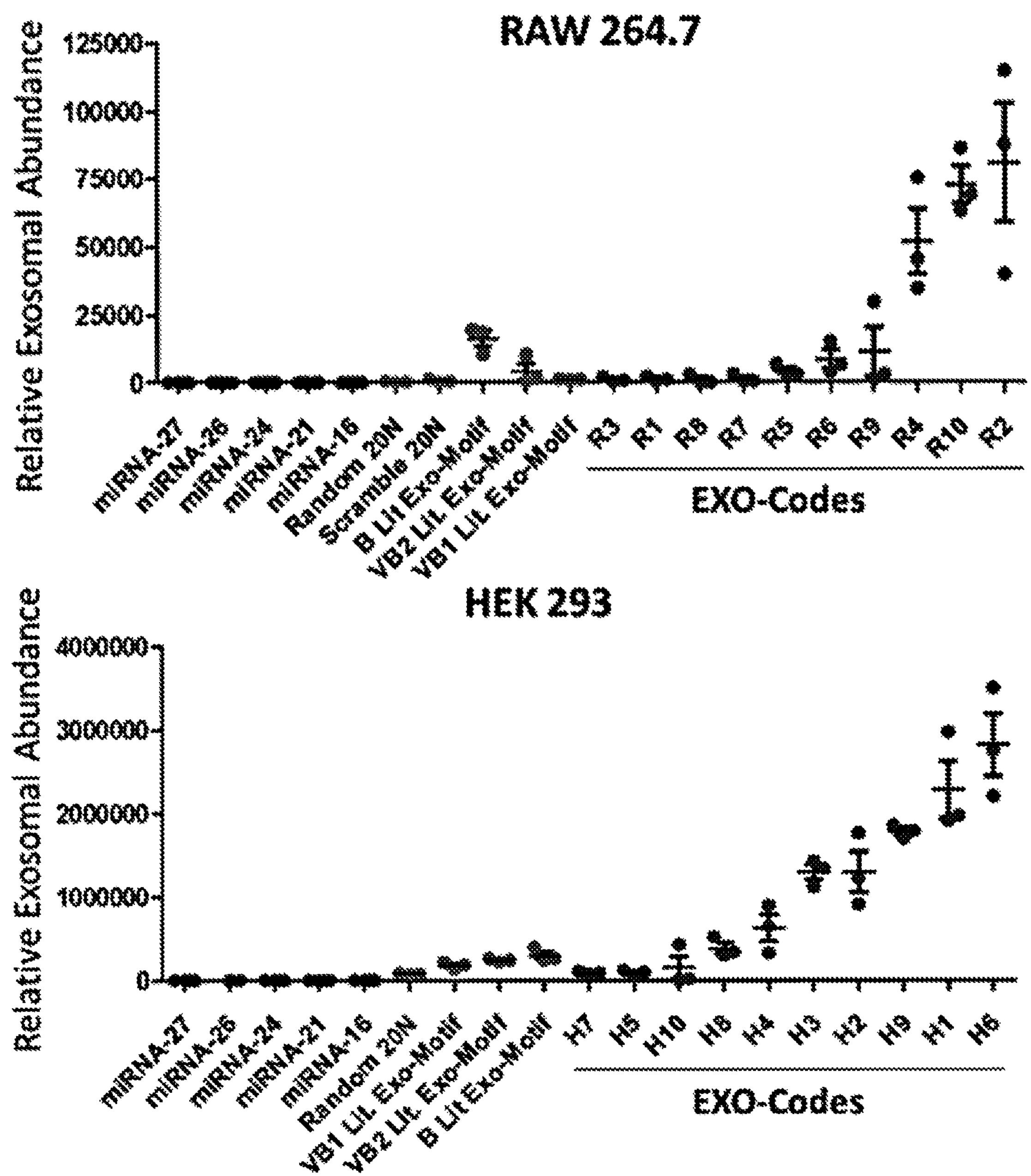

Table 1: The top 10 sequences by read counts (highest to lowest) at selection rounds 7 or 10 for MDA-MB-231 cells, Mesenchymal stem cells, Raw 264.7 cells, HEK 293 Cells FIG. 9 depicts relative exosomal enrichment of EXO-Codes after electroporation into their parent cell lines (MDA-MB-231 cells, mesenchymal stem cells, Raw 264.7 cells, and HEK 293 cells. The following sequences serve as control sequences: Random 20N: ACAGUAGAGCCUUCACCGGC (SEQ ID NO:51), MDA Scramble 20N: GCUCUCGGAAGGCUUGGGCU (SEQ ID NO:52), RAW Scramble 20N: AGUCGGGGUAUGCCUGGAUG (SEQ ID NO:53), Literature Exo-Motif VB1: UGGUCUAGGAUUGUU-GGAGGAG (SEQ ID NO:54), Literature Exo-Motif VB2: GGUCCAGAGGGGAGAUAGGUUC (SEQ ID NO:55) [from Villarroya-Beltri et al. *Nat Commun.* 2013; 4:2980. doi: 10.1038/ncomms3980], and Literature Exo-Motif B: ACCCUGCCGCCUGGACUCCGCCUGU (SEQ ID NO: 56) [Bolukbasi et al. Mol Ther Nucleic Acids. 2012 Feb. 7; 1:e10. doi: 10.1038/mtna.2011.2.]. 10 μg of each RNA was electroporated into, for MDA, 6E5 cells; for RAW, 1.5E6 cells; for HEK, 1E6 cells; and for MSC, 3E5 cells using the optimized Neon settings for each cell line in a 100 μL tip. The cells were dispensed into DMEM and washed three times. The cell suspension for each RNA was split into 3 wells of a 12-well plate and supplemented to 500 μL with EXO-media. Cells were cultured near confluency for 72 hours before collecting exosomes/EVs. The exosomes/EVs were resuspended in 100 μl of PBS, 1 μl was used for exosome/EV quantification while the remaining sample was RNAse treated, and then processed with Qiazol for RNA extraction. 30 ng of *C. elegans* miRNA 39 (UCACCGGGUGUAAAUCAGCUUG (SEQ ID NO:57)) and 54 (UACCCGUAA-UCUUCAUAAUCCGAG (SEQ ID NO:58)) were spiked into each sample at this step. Total RNA was cleaned on the miRNeasy column and cDNA was synthesized with the qScript microRNA cDNA synthesis kit from Quanta. RNAs were quantified using SYBR Low ROX from Quanta in a PCR reaction. RNA copies were obtained from the standard curve of each RNA, as well as correcting for cDNA input amount and the average recovery percent from the two spike-in RNAs. This number was normalized by the quantity of exosomes/EVs which were recovered for each sample. B) Setting the Random 20N to 1 demonstrates a fold enrichment of 15 to 400 relative RNA copies per EV for the best performing EXO-Codes. C) Setting a panel of quantified endogenous miRNAs from the same samples to 1 demonstrates the remarkable increase in RNA potency using the EXO-Code technology. EXO-Codes are 1E5 to 3E6 times more abundant in exosomes/EVs than endogenous RNAs.

Figure 10:
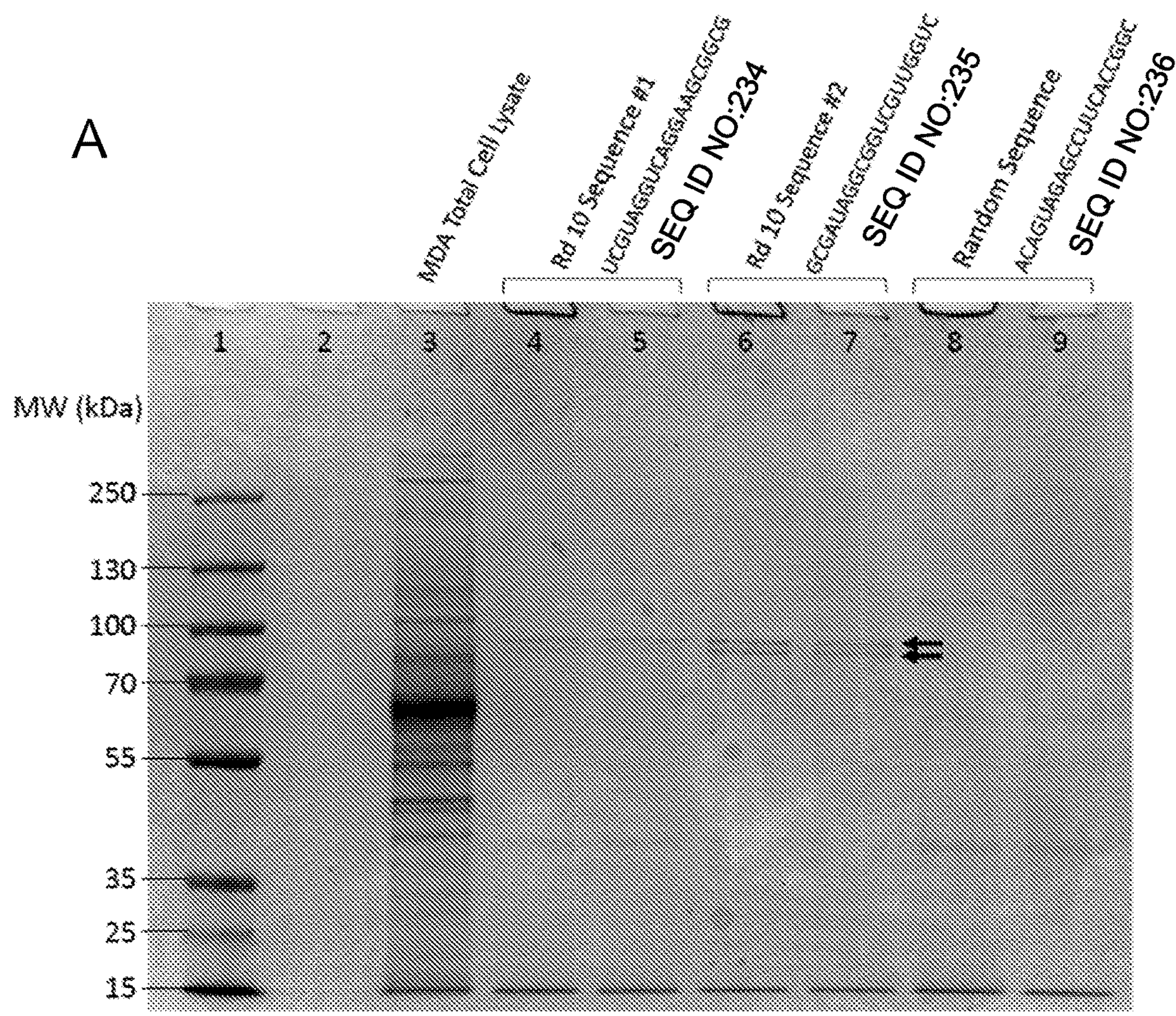
FIG. 10 shows (A, B, and C) RNA-pull down assays.
Figure 10:
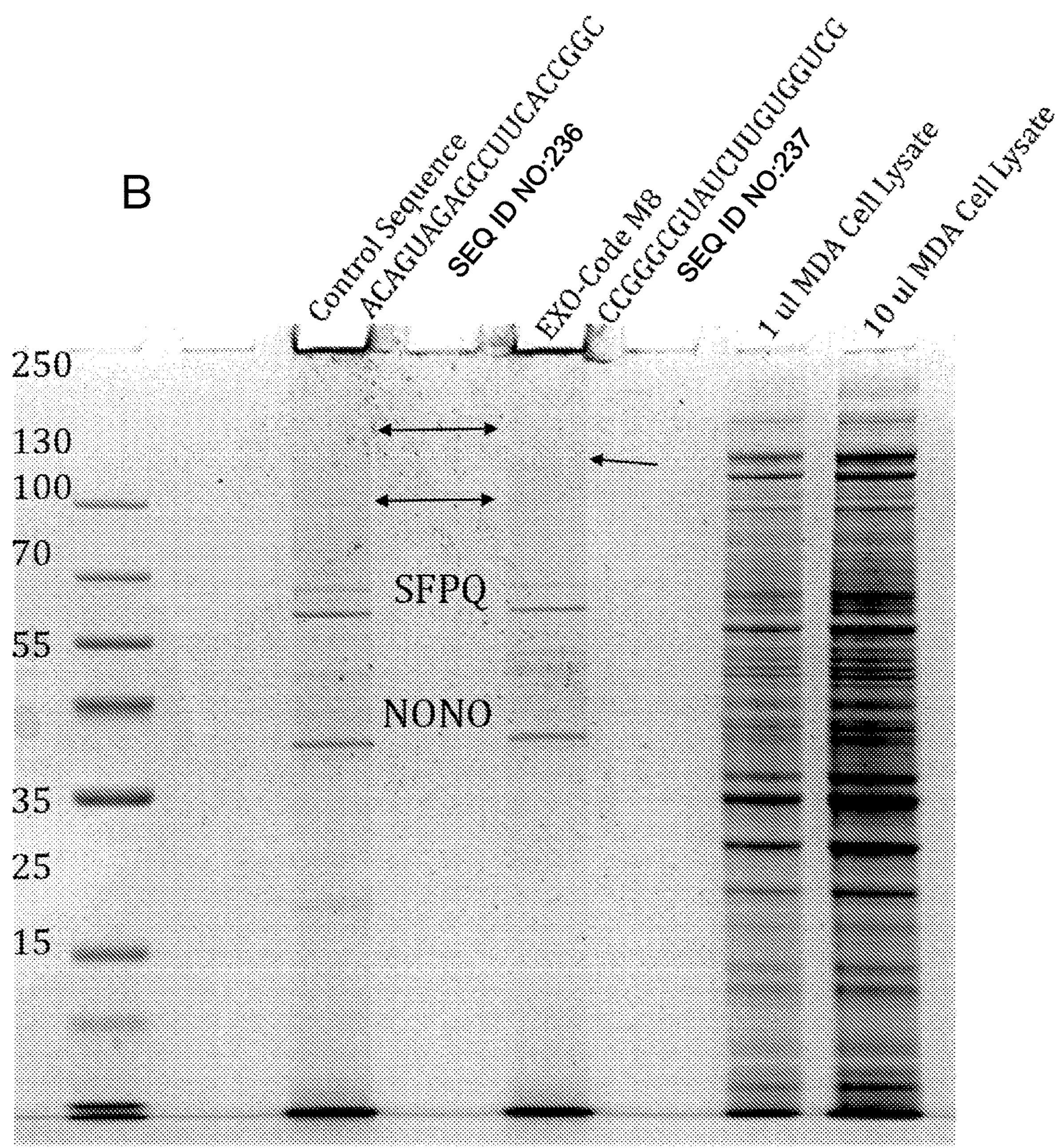
Figure 10:
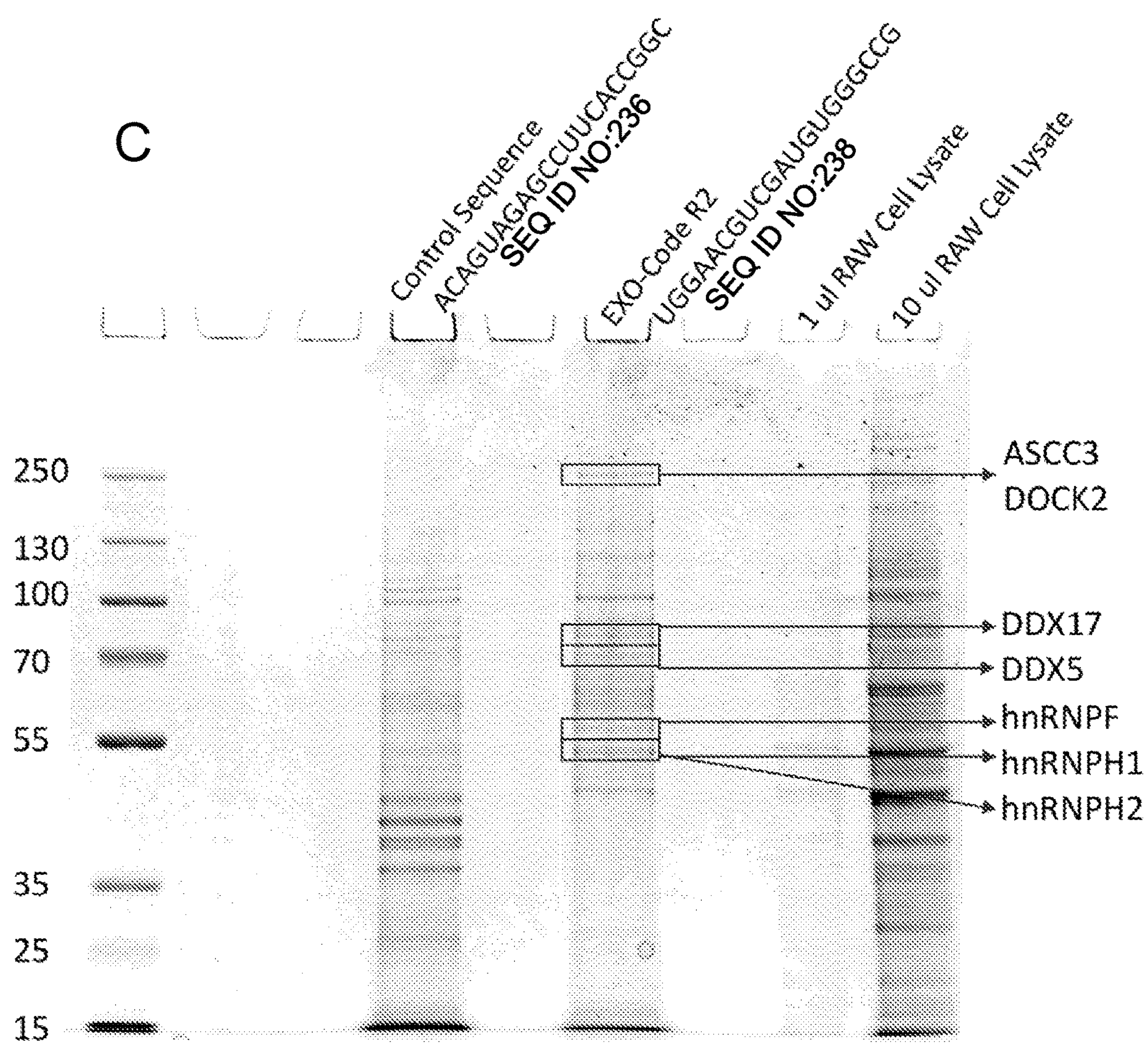

FIG. 10 A depicts RNA-pull down assays using the top two sequences identified in round 10 for MDA-MB-231 cells. Lane 4 & 5: UCGUAGGUCAGGAAGCGGCG (SEQ ID NO:59), Lane 6&7: GCGAUAGGCGGUCGUUGGUC (SEQ ID NO:60). Proteins indicated by arrow in lanes 4-7 identified as hnRNPM. FIG. 10 B: shows both the control RNA and M8 EXO-Code RNA bound to NONO (Non-POU domain-containing octamer-binding protein) and SFPQ (Splicing factor, proline- and glutamine-rich) RNA-binding proteins. However, M8 EXO-Code bound to hnRNPM much more than the control RNA in the pulldown assay (indicated with arrow). In FIG. 10 C, in the pulldown assay for the most enriched EXO-Code in RAW Cells (R2) the biotinylated RNA bound to numerous proteins more than the control RNA. Mass spectrometry identified the most differentially bound proteins to be the murine ASCC3, DOCK2, DDX17, DDX5, hnRNPF and hnRNPH1/H2.

The RNA-pull-down assay of FIG. 10A shows two bands between 70 and 100 kDa (indicated by arrows) present for the top two sequences identified in round 10 for MDA cells (lanes 4-7) which is not present in the scramble control sequence pull-down (lanes 8 & 9). The two bands were excised from lanes 6 & 7 and along with the corresponding control region in lanes 8 & 9 were analyzed by mass spectroscopic analysis. Both bands were identified as heterogeneous nuclear ribonucleoprotein M (hnRNP M), predicted kDa 72/74. Lanes 4, 6, and 8 were loaded into the wells along with the magnetic streptavidin beads, while lanes 5, 7, and 9 were loaded with the remaining lysate of the same pull-down without the magnetic streptavidin beads. In FIGS. 10 B & C results of the pulldown experiments performed with MDA #8 sequence from round 10 and the #2 sequence at Round 10 in RAW 264.7 cells is shown. To obtain results in FIG. 10, biotinylated RNA sequences were 3'-biotin modified. 20 ug RNA was incubated for 1 h with pre-cleared cell lysate of MDA cells (1 ml of 1 mg/ml cell lysate from $3\times10^7$ cells). Bound proteins were then captured using Promega magnetic-streptavidin beads (45 min incubation) and unbound proteins were removed with 5 washes. All steps were performed at 4° C. using protease and RNAse-treated buffers. hnRNPM is known to be present in the exosomes from MDA-cells from previous studies and shown to be important in the metastatic phenotype of MDA-MB-231 cells. hnRNPM is also shown to be necessary for breast cancer cells to efficiently metastasize to lung in vivo (Xu Yet. *Genes Dev.* 2014 Jun. 1; 28(11):1191-203).

Pull-Down Assays and Mass Spectrometry can be Used.

Magnetic streptavidin beads coated with: (a) biotinylated EXO-Codes or (b) biotinylated poly(A) RNA sequences as negative controls are incubated with cellular and exosomal extracts from MDA-MB-231, Raw 264.7 cells, and other cell types. The proteins that bind to the EXO-Codes are analyzed using a highly sensitive and comprehensive liquid chromatography-mass spectrometry (LC-MS)-based proteomics approach. 3'-biotinylated EXO-Codes are heated to 65° C. and then cooled to 4° C. over 30 min to ensure proper folding. 3'-biotinylated RNA are then be added to the exosomal lysate or cell lysate and incubated for 1 h at 4° C. with rotation. Casein-blocked magnetic streptavidin beads are added to the mixture and incubated for 30 min. The beads are washed by magnetic separation. The beads are re-suspended in water after the final wash and prepared in an LDS-reducing buffer before running on Nupage 4-12% Bis/Tris gels. The gels are stained with Coomassie (BioRad) or SilverQuest (Invitrogen) if necessary. Protein bands unique to the EXO-Code RNAs but not found on the control RNA are excised and analyzed by mass spectrometry on a Q Exactive plus. The data are analyzed within Proteome Discoverer 1.4 using the Mascot search engine SwissProt fasta human database. Trypsin is used as the enzyme, while allowing for 1 missed cleavage. Oxidized methionine will be set as a variable modification, while carbamidomethyl will be set as a static modification.

Minimum Sequence Requirements and Binding Affinities.

In silico docking-informed point mutations are introduced into the identified EXO-Code sequences to elucidate the minimum sequence requirements. Using the Surflex docking toolkit on the SYBYL platform we were able to rank-order the RNA sequences and their mutations according to their binding affinity to HNRNP L. This approach can be extended to any additional EXO-Codes discovered or described herein, as well as de novo EXO-Code-binding protein targets identified from the pull-down mass spectrometry experiments.

Protein-Nucleic Acid Interactions.

Identified proteins are overexpressed and purified from *E. coli* and electrophoresis motility shift assays performed using the purified proteins, our novel EXO-Codes, and the control poly(A) RNA sequence. Experiments are performed using radioactively labeled RNA substrates. 32P-radiolabeled T7-transcribed RNA substrates are incubated with increasing concentrations of the identified protein and then resolved on a 4.5% native polyacrylamide gel. The gel is imaged with a PhosphorImager SI (Amersham). Protein-bound RNA will migrate slower than free RNA.

Surface plasmon resonance may be used to determine the binding affinity of the EXO-Codes and their mutations to the identified proteins. Binding analysis is performed with a Reichert SR7000 DC SPR instrument. The identified proteins are immobilized on the surface of carboxymethyl dextran hydrogel gold chips using standard amine coupling chemistry. Samples containing the RNA sequences are flown over the chip to determine binding affinity. Regeneration of the gold chip is performed using a 10 mM glycine solution pH 2 to remove bound analytes. Binding affinity data are correlated to the in silico predictions and to the sorting efficiency and kinetics of the EXO-Codes.

Loss-of-Function Studies: Silencing and Overexpression of Identified Proteins.

Loss-of-function studies may be performed to assess the effect of the respective proteins on sorting of the EXO-Codes by gene silencing and overexpression of the identified candidates in MDA-MB-231, PC-3, Raw 264.7, HEK293, and mesenchymal stem cells. Silencing and overexpression of the proteins can be confirmed by RT-PCR (on the mRNA level) and western blotting (on the protein level) of cellular and exosomal samples. RNA enrichment in exosomes is monitored by RT-PCR.

Figure 11:
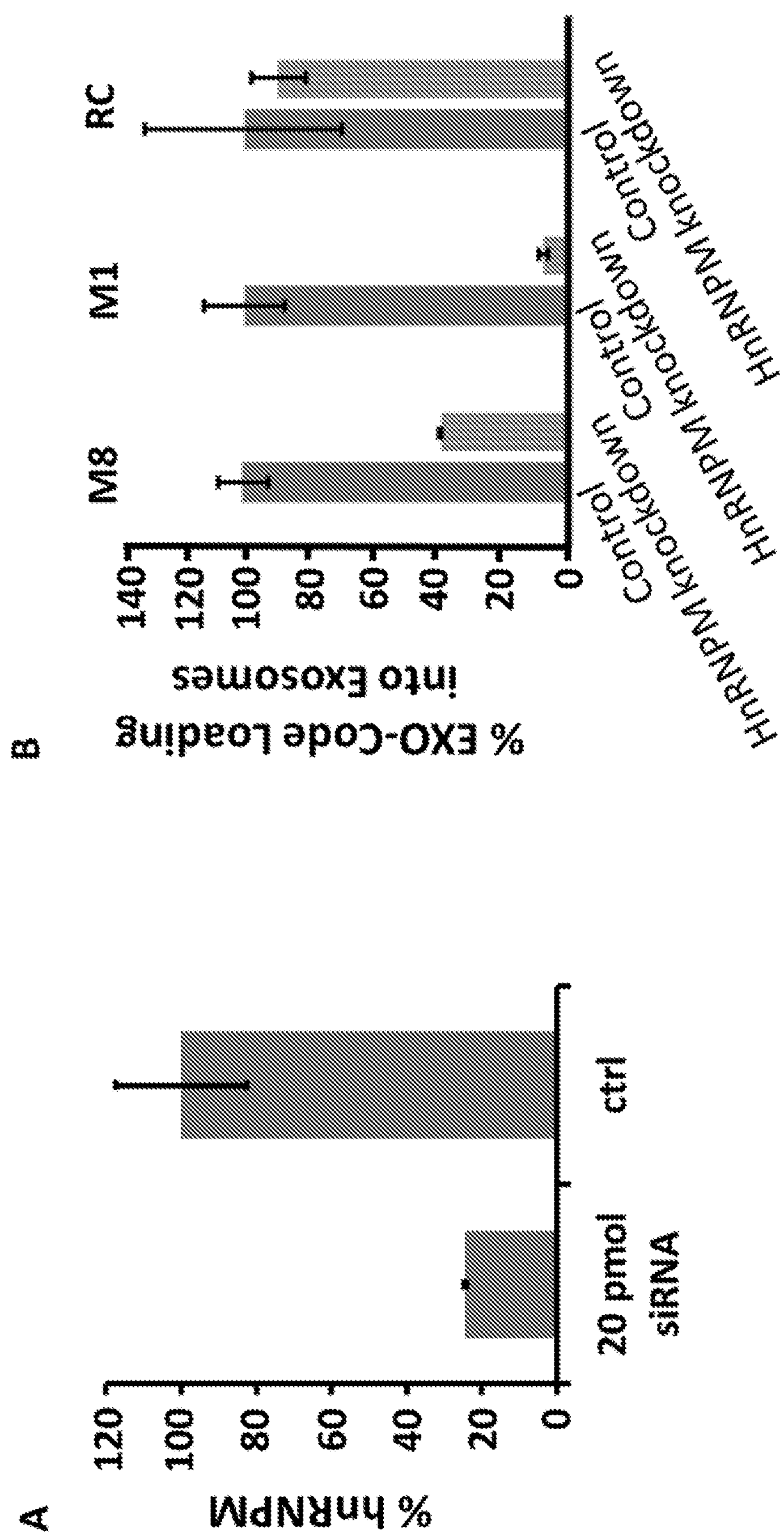
FIG. 11 shows A) MDA-MB-231 cells were treated with a control siRNA (sense: UCACAAGG-GAGAGAAAGAGAGGAAGGA (SEQ ID NO:61)) or two hnRNPM siRNAs (sense1: GCAUAGGAUUUG-GAAUAAA (SEQ ID NO: 62)) sense2: GGAAUG-GAAGGCAUAGGAUUU (SEQ ID NO:63)) at 30 pmol of total siRNA in a 12-well plate using RNAiMAX. A) Three wells from each condition were collected at 48 hours post transfection and a western blot was run to assess hnRNPM knockdown (Origene TA301557). B) Percent knockdown normalized to GAPDH was assessed using ImageJ software. At 48 hours post siRNA treatment an additional 3 wells from each condition were electroporated with 1 μg EXO-Code M1 RNA or M8. At 24 hours post electroporation exosomes/EVs were collected and RNA was extracted. Relative M1 and M8 abundance was determined from qPCR. Cells which had been depleted of about 75% of hnRNPM showed an approximately 60% decrease in loading of M8 EXO-Code and an approximately 90% decrease in loading of M1 EXO-Code into exosomes/EVs. hnRNPM knockdown did not affect the sorting of the random control (RC) sequence.

In FIG. 11 A) MDA-MB-231 cells were treated with a control siRNA (sense: UCACAAGGGAGAGAAA GAGAGGAAGGA (SEQ ID NO:61)) or two hnRNPM siRNAs (sense1: GCAUAGGAUUUGGAAUAAA (SEQ ID NO: 62)) sense2: GGAAUGGAAGGCAUAGGAUUU (SEQ ID NO:63)) at 30 pmol of total siRNA in a 12-well plate using RNAiMAX. A) Three wells from each condition were collected at 48 hours post transfection and a western blot was run to assess hnRNPM knockdown (Origene TA301557). B) Percent knockdown normalized to GAPDH was assessed using ImageJ software. At 48 hours post siRNA treatment an additional 3 wells from each condition were electroporated with 1 μg EXO-Code M1 RNA or M8. At 24 hours post electroporation exosomes/EVs were collected and RNA was extracted. Relative M1 and M8 abundance was determined from qPCR. Cells which had been depleted of about 75% of hnRNPM showed an approximately 60% decrease in loading of M8 EXO-Code and an approximately 90% decrease in loading of M1 EXO-Code into exosomes/EVs. hnRNPM knockdown did not affect the sorting of the random control (RC) sequence.

The disclosure includes assessing the ability of EXO-Codes to deliver therapeutic cargoes to exosomes. We have identified EXO-Codes that are enriched in exosomes. These EXO-Codes are expected to be used to deliver therapeutic cargoes to reprogram pathological exosomes and exert a phenotypic effect. RNA size-efficiency relationships and RNA-size kinetic relationships can be determined. The ability of the EXO-Codes to reprogram tumor-derived exosomes can be assessed in a migration and invasion assay.

In one non-limiting illustration of an embodiment of the present disclosure we attached pre-miR-31 to the EXO-Code identified described above to reprogram exosomes derived from MDA-MB-231 cells. miR-31, an anti-metastatic miRNA acts as a tumor suppressor and inhibits cancer cell proliferation, migration, and metastasis.

Figure 12:
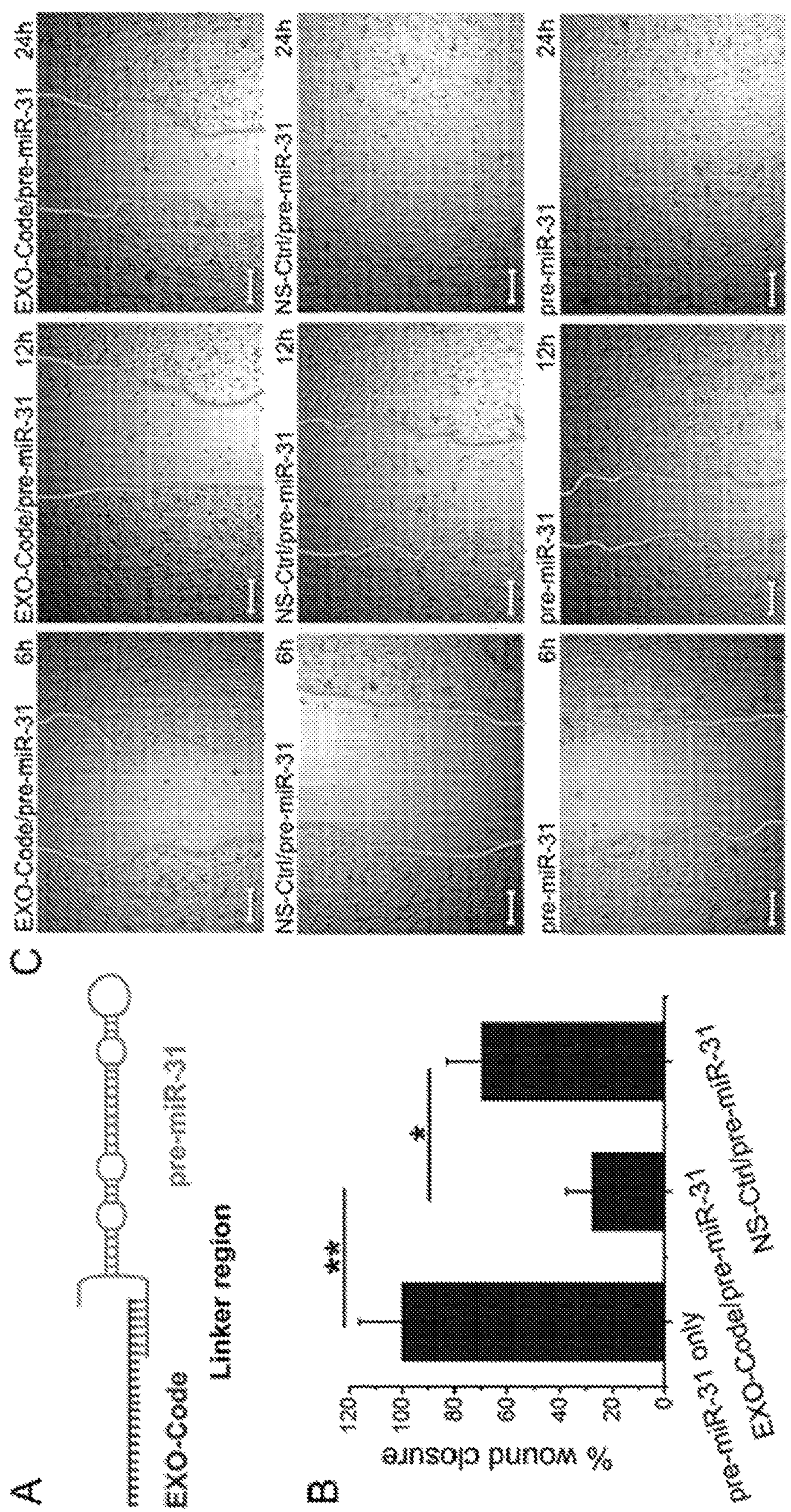
FIG. 12 shows (A) a schematic illustration of the EXO-Code/pre-miR-31 chimera. (B) Exosomes reprogrammed with a chimerized EXO-Code/pre-miR-31 inhibits cellular migration by 75%. In contrast, exosomes derived from cells treated with NS-Ctrl/pre-miR-31 chimera showed only 31% inhibition of migration of MDA-MB-231 cells. Compared to the pre-miR-31 only ctrl the inhibition was not statistically significant. (C) Representative images of the scratch assay show complete closure of the gap when cells were incubated with exosomes derived from cells treated with NS-Ctrl/pre-miR-31 and pre-miR-31 ctrl. After 24 h, a substantial gap can be still seen with MDA-MB-231 cells treated with exosomes reprogrammed with EXO-Code/pre-miR-31. Scale bar: 200 μm. Data are mean±sd. $^{**}P<0.01$, $^{*}P<0.05$ by one-way ANOVA with post-hoc Tukey.

FIG. 12 (A) provides a schematic illustration of the EXO-Code/pre-miR-31 chimera. (12B) Exosomes reprogrammed with a chimerized EXO-Code/pre-miR-31 inhibits cellular migration by 75%. In contrast, exosomes derived from cells treated with NS-Ctrl/pre-miR-31 chimera showed only 31% inhibition of migration of MDA-MB-231 cells. Compared to the pre-miR-31 only ctrl the inhibition was not statistically significant. (12C) Representative images of the scratch assay show complete closure of the gap when cells were incubated with exosomes derived from cells treated with NS-Ctrl/pre-miR-31 and pre-miR-31 ctrl. After 24 h, a substantial gap can be still seen with MDA-MB-231 cells treated with exosomes reprogrammed with EXO-Code/pre-miR-31. Scale bar: 200 μm. Data are mean±sd. $^{**}P<0.01$, $^{*}P<0.05$ by one-way ANOVA with post-hoc Tukey.

For exosomal reprogramming, MDA-MB-231 cells were electroporated with EXO-Code/pre-miR-31 chimera, pre-miR-31 only, and a non-specific ctrl/pre-miR-31 chimera and cultured in exosome-depleted media for 48 hours. To obtain EXO-Code/pre-miR-31 chimera as shown in FIG. 9A, the EXO-Code is synthesized with a linker region resulting in the following sequence: 5' GUACAUUCUAGAUAGCCaugau-UGUGUGUCCCCACAGCACU-Guug-3' (SEQ ID NO:64). This linker region is annealed to the complementary linker attached to the pre-miR-31: 5' GGC UA UCUAGAAUGUACaaAG GCAAGAGCUGGCAUAGCUGUUGAACUGGGAACUG CUAUGCCA-ACAUA-UUGCCAU-3' (SEQ ID NO:65). Italics indicates the complementary linker regions, bold indicates the EXO-Code, and the mature miR-31 is underlined. The media was collected and exosomes precipitated using the Total Exosome Isolation Reagent (Invitrogen). Exosomes were resuspended in PBS and administered to MDA-MB-231 cells plated for in vitro scratch assays, a well-established method to assess cell migration and cellular invasion [64]. Briefly, to obtain a cell-free gap, the centers of wells were scratched using a pipette tip. Gap closure was used as a marker of cellular migration. Reprogrammed exosomes derived from cells treated with the EXO-Code/pre-miR-31 inhibited cellular migration by 75% (FIG. 9 B&C). In contrast, exosomes derived from cells treated with NS-Ctrl/pre-miR-31 chimera showed only 31% inhibition of migration of MDA-MB-231 cells.

Delivery of Different Size Cargoes and Determining Exosomal Loading Capacity.

For optimization of cargo loading, the ability of the EXO-Codes to load cargoes of varying sizes is assessed. Loading of miRNAs, siRNAs, DNA, and larger nucleic acids (such as mRNAs or plasmid DNA) into exosomes is monitored by RT-PCR. Relationships between RNA size and loading efficiency and RNA size and loading kinetics can be determined. Passive strategies that stably transfect cells with siRNAs or miRNAs to indirectly load exosomes are prevalent in the literature. However, these methods are highly inefficient, require high amounts of RNA, and are unsuitable for direct in vivo reprogramming, with loading of larger nucleic acids, such as mRNA and pDNA, especially challenging using conventional methods (about 0.3% loading efficiency). mRNAs are thought to be loaded into exosomes via sequence-specific sorting. By attaching EXO-Codes to mRNAs, the disclosure mimics the endogenous sorting strategy to efficiently load mRNAs into exosomes. Green fluorescent protein (GFP) can be used as a model protein for mRNA delivery. The miRNA/siRNA and mRNA attached to EXO-Codes are delivered to MDA-MB-231, mesenchymal stem cells, and other cells by (a) electroporation and (b) by liposomal transfection using our lipids, polymers, or peptides. The amount of miRNA/siRNA and mRNA sorted to exosomes can be quantified by stem-loop RT-PCR (for miRNA/siRNA) and RT-PCR for mRNA.

Loading of Cargoes Capable of Mediating Tissue Regeneration into Exosomes.

Figure 13:
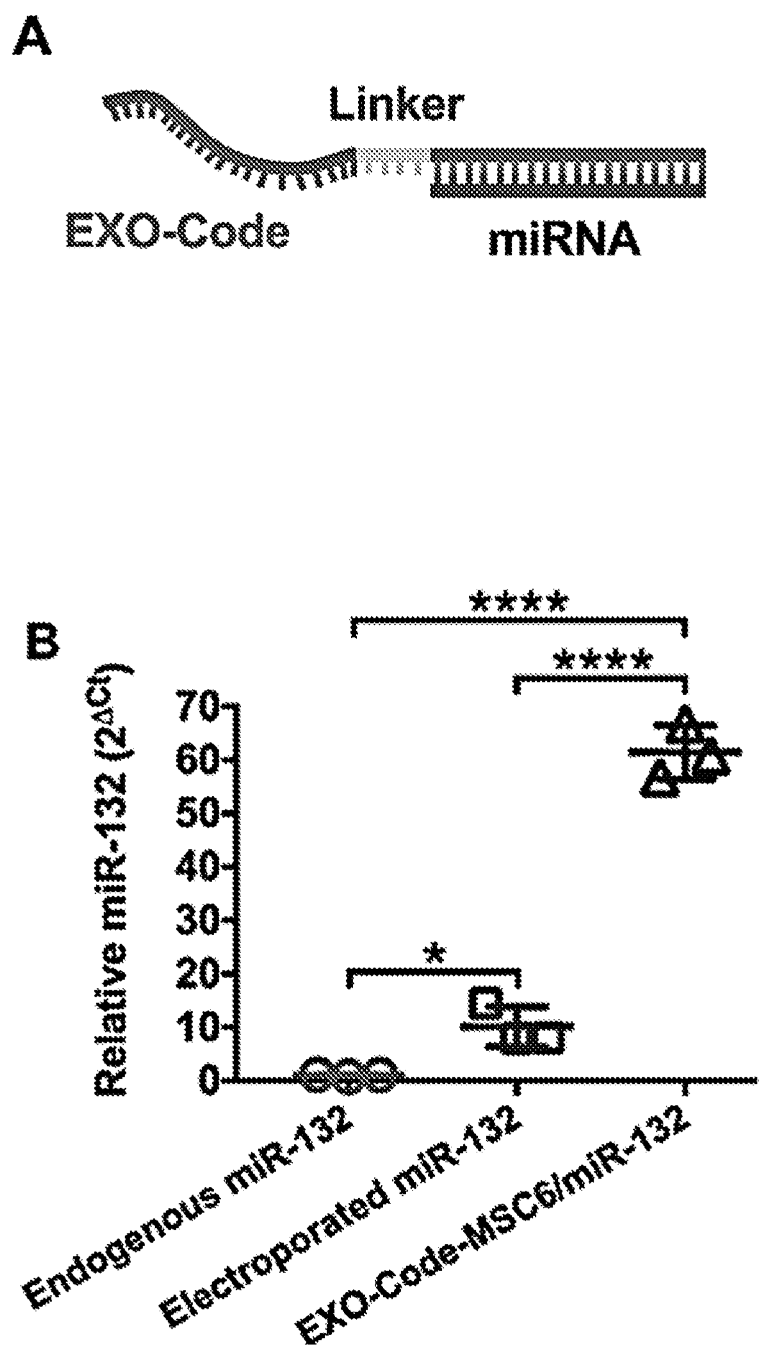
FIG. 13 shows (A) EXO-Code S6, the number 6 sequence from Stem Cells after 7 rounds of selection was added to the complementary sequence of miR-132 spaced apart with a "A" linker to form the top strand RNA: GCUGGUCAG-GAUGCGGGGGCAAAGUAACAAUCGAAAGCCACG-GUUUU (SEQ ID NO:66); this RNA was then duplexed to synthetic miR-132: AACCGUGGCUUUCGAUUGUUA-CUU (SEQ ID NO:67). (B) Mesenchymal stem cells were electroporated in triplicate with equal molar amounts of synthetic miR-132 alone or miR-132 attached to the S6 EXO-Code. Exosomes were collected and quantified for miR-132, electroporated miR-132 elevated the amount of this miRNA in mesenchymal stem cell exosomes by 10 fold. Utilizing EXO-Code S6 achieved an additional 6-fold increase in exosomal abundance—increasing the miR-132 potency of the MSC exosomes by 60-fold. (C) Angiogenesis assay on human umbilical vein endothelial cells (HUVECs). HUVECs were treated with exosomes collected from human mesenchymal stem cells electroporated with either EXO-Code-MSC6/miR-132 or unmodified miR-132. In all shown parameters exosomes derived from mesenchymal stem cells treated with EXO-Code-MSC6/miR-132 showed statistically significant increase in the number of nodes, number of junctions, total length, total branching lengths, and number of branches. Data were analyzed with one-way-Anova with post-hoc Tukey (n=3), $^{**}p<0.0001$, $^{*}p<0.001$, $^{**}p<0.01$, $^{*}p<0.5$.
Figure 13:
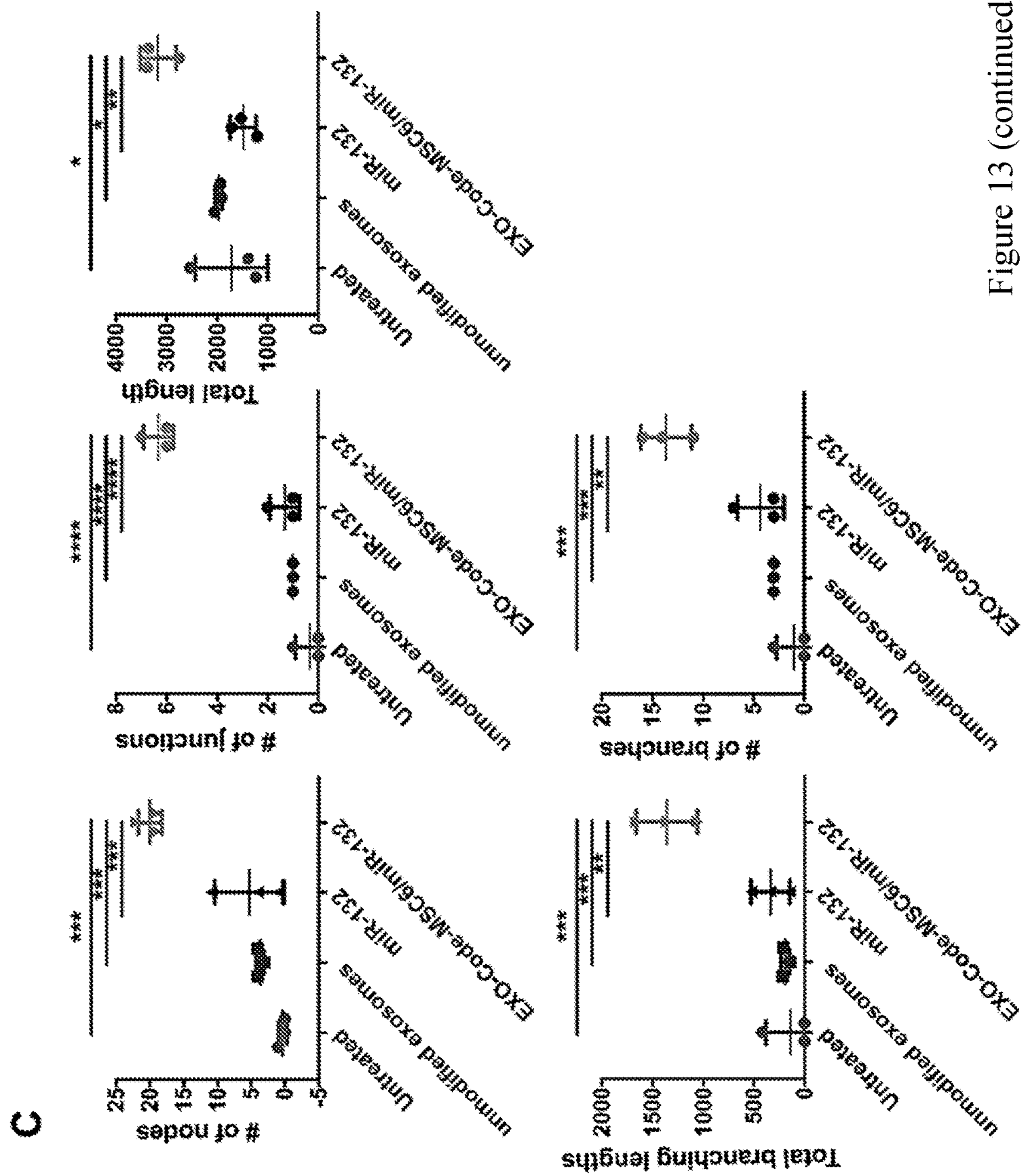

In FIG. 13, miRNA loading into exosomes derived from human mesenchymal stem cells (MSC) is shown. The EXO-Code-MSC6 mediated significantly higher enrichment of miR-132 into exosomes than when only miR-132 is electroporated into the human MSCs. To test the effects of loaded exosomes on angiogenesis, human umbilical vein endothelial cells (HUVECs) were treated with exosomes derived from cells electroporated with only miR-132 or with the EXO-Code-MSC6/miR-132 chimera and then plated on a 96-well plate coated with Geltrex. 17 h later, the cells were stained with calcein and imaged at em/ex 495/515 with the SpectraMax MiniMax 300 Imaging Cytometer. Exosomes containing EXO-Code-MSC6-miR-132 mediated significantly higher effects on angiogenesis than unmodified exosomes or exosomes derived from MSCs electroporated with only miR-132. Angiogenesis assay is often used as a surrogate assay to assess the formation of new blood vessels, which is relevant in processes involved with wound healing and tissue regeneration.

FIG. 13 Shows Data Obtained from miRNA Loading into Human Mesenchymal Stem Cell Exosomes and Effects on Angiogenesis.

FIG. 13: (A) EXO-Code S6, the number 6 sequence from Stem Cells after 7 rounds of selection was added to the complementary sequence of miR-132 spaced apart with a "A" linker to form the top strand RNA: GCUGGUCAGGAUGCGGGGGCAAAGUAACAAUCGAAAGCCACGGUUUU (SEQ ID NO:66); this RNA was then duplexed to synthetic miR-132: AACCGUGGCUUUCGAUUGUUACUU (SEQ ID NO:67). (B) Mesenchymal stem cells were electroporated in triplicate with equal molar amounts of synthetic miR-132 alone or miR-132 attached to the S6 EXO-Code. Exosomes were collected and quantified for miR-132, electroporated miR-132 elevated the amount of this miRNA in mesenchymal stem cell exosomes by 10 fold. Utilizing EXO-Code S6 achieved an additional 6-fold increase in exosomal abundance—increasing the miR-132 potency of the MSC exosomes by 60-fold. (C) Angiogenesis assay on human umbilical vein endothelial cells (HUVECs). HUVECs were treated with exosomes collected from human mesenchymal stem cells electroporated with either EXO-Code-MSC6/miR-132 or unmodified miR-132. In all shown parameters exosomes derived from mesenchymal stem cells treated with EXO-Code-MSC6/miR-132 showed statistically significant increase in the number of nodes, number of junctions, total length, total branching lengths, and number of branches. Data were analyzed with one-way-Anova with post-hoc Tukey (n=3), **p<0.0001, *p<0.001, **p<0.01, *p<0.5.

Figure 14:
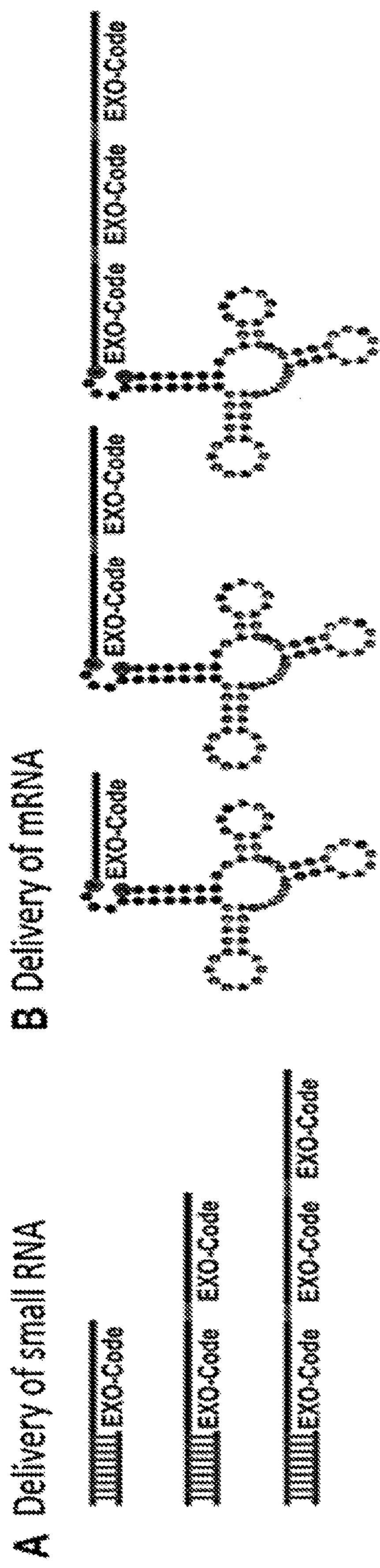
FIG. 14 shows a schematic showing assessment of the capabilities of EXO-Codes to deliver different sized cargoes to exosomes. The miRNA/siRNA and mRNA containing multivalent EXO-Codes can be delivered to MDA-MB-231, PC-3, and other cells by (A) electroporation and (B) by liposomal, polymer, and peptide transfection, as well as by other suitable methods. The amount of miRNA/siRNA and mRNA sorted to exosomes can be quantified by stem-loop RT-PCR (for miRNA/siRNA) and RT-PCR for mRNA.

The effect of multivalency on the kinetics and efficiency of exosomal sorting can be assessed. EXO-Codes can be attached to the cargo (miRNA and mRNA) at different valencies (n=1-3). In this regard, FIG. 14 provides a schematic showing assessment of the capabilities of EXO-Codes to deliver different sized cargoes to exosomes. The miRNA/siRNA and mRNA containing multivalent EXO-Codes can be delivered to MDA-MB-231, PC-3, and other cells by (a) electroporation and (b) by liposomal, polymer, and peptide transfection, as well as by other suitable methods. The amount of miRNA/siRNA and mRNA sorted to exosomes can be quantified by stem-loop RT-PCR (for miRNA/siRNA) and RT-PCR for mRNA.

Delivery of Metastasis-Suppressing siRNA/miRNA.

To reprogram pathological, metastasis-initiating exosomes, in certain embodiments Snail and Slug are targeted. Snail and Slug play major roles in tumor growth and induction of distant metastasis in a variety of cancer types. They belong to the family of zinc-finger transcription factors that are involved in the 'Epithelial to Mesenchymal Transition' (EMT) of cancer cells EMT, which plays an important role in tumor metastasis, is a mechanism by which epithelial cells acquire a mesenchymal phenotype that possesses enhanced migratory capacity and is significantly more invasive. Silencing Snail and Slug has been shown to significantly decrease tumor growth and lymph node metastasis of breast cancer and prostate cancer cells. The disclosure includes delivery of chimerized EXO-Codes/siRNA against SnailI and Slug as the targets for exosomal reprogramming in cancer cells. To obtain chimerized EXO-Code/siRNA constructs, the sense strand is covalently linked to the EXO-Code and the antisense strand is annealed to the sense strand. The following siRNA sequences will be used: Snail: 5-CCACAGAAAUGGCCAUGGGAAGGCCUC-3 (SEQ ID NO:68), Slug: 5-UCCGAAUAUGCAUCUUCAGGGC GCCCA-3 (SEQ ID NO:69), negative control. 5-UCACA AGGGAGAGAAAGAGAGGAAGGA-3 (SEQ ID NO:70).

Migration Assay Using an In Vitro Scratch Assay.

EXO-Codes can be chimerized to anti-metastatic miRNAs (miR-31), anti-Snail and anti-Slug siRNA, known to act as inhibitors of cellular migration, invasion, and metastasis. These EXO-Codes/miRNAs and EXO-Codes/siRNAs are expected to be able to be delivered to tumor cells for exosomal reprogramming. The ability of the reprogrammed exosomes to inhibit cellular migration can be assayed using the scratch assay (FIG. 12). Migration of MDA-MB-231, PC-3 cells, and other cancer cells receiving reprogrammed exosomes will be monitored by microscopy at 24 h, and 48 h post-incubation. The scratch area and the number of cells that have migrated into the scratch area will be quantified using ImageJ software. The effect of reprogrammed exosomes on cellular migration can be corroborated by RT-PCR of respective mRNAs to exclude non-specific inhibitory mechanisms.

Invasion Assay.

A modified matrigel-coated Boyden chamber assay can be used to assess the invasiveness of MDA-MB-231 cells, PC-3 cells, and other cancer cells treated with the reprogrammed exosomes. Cells are plated onto the apical site of transwells and treated with reprogrammed exosomes. After 24 and 48 h, the number of cells migrating to the basolateral are counted. 10 fields per membrane with a minimal cell number of 10 will be counted.

Dose-Response Relationship.

To establish a dose-response relationship, cells can be treated with increasing concentrations of reprogrammed exosomes and the effect on cellular migration and invasion determined. Further, cellular uptake of reprogrammed exosomes into MDA-MB-231 cells, PC-3 cells, and HEK 293, mesenchymal stem cells, Raw cells, cardiomyocytes, endothelial cells, and other cell types can be determined. Exosomes can be fluorescently labeled with a PKH26 membrane dye (Sigma Aldrich). The amount of exosomes taken up into cells will be quantified by flow cytometry.

To generate chemically modified RNA for increasing stability of the EXO-Codes, the DNA templates were translated into RNA using methyl CTP and pseudo UTP in the in vitro reaction. In two examples (FIG. 15), chemically modified EXO-Codes showed significantly increased enrichment into exosomes over random control and/or unmodified EXO-Codes.

Figure 15:
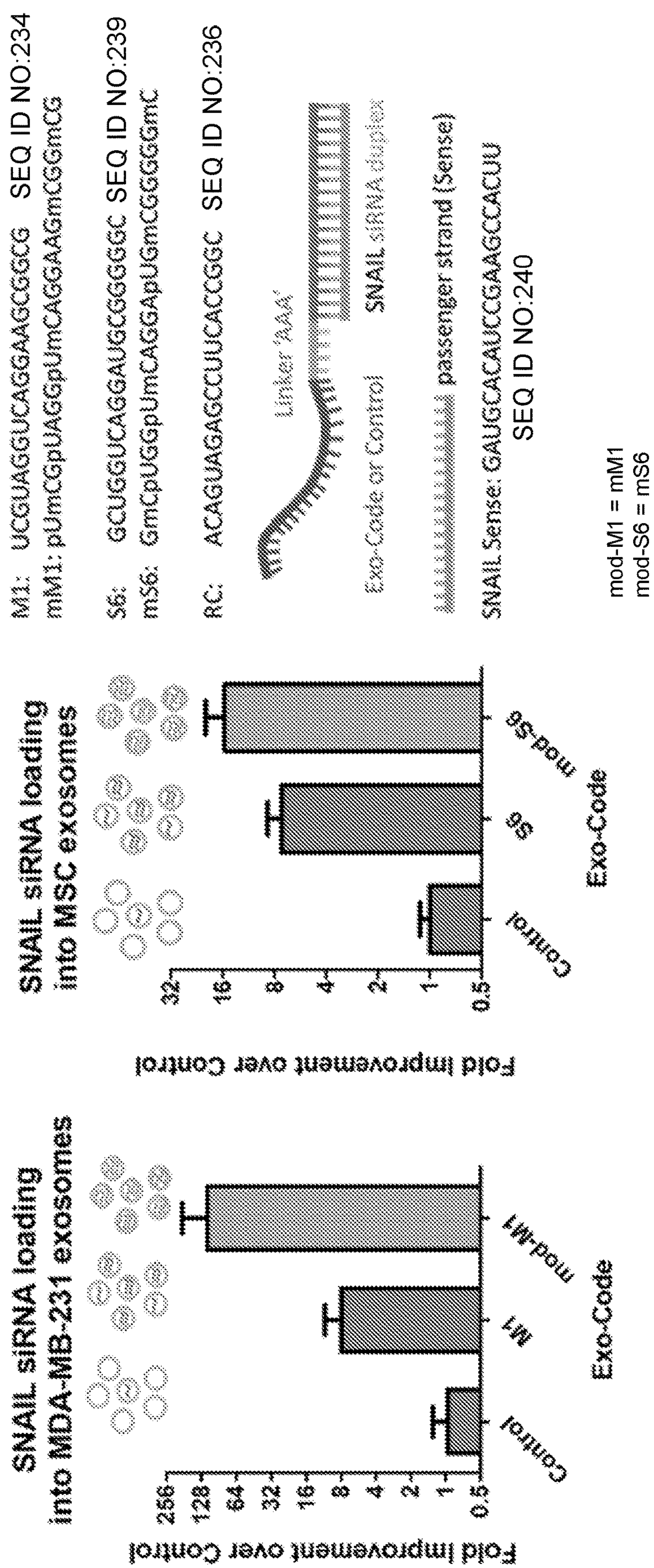
FIG. 15 shows increased loading of SNAIL siRNA in Stem Cells and MDA Cells using Modified Nucleotides.

FIG. 15 demonstrates increased Loading of SNAIL siRNA in Stem Cells and MDA Cells using Modified Nucleotides. In particular, the EXO-Code S6, the Random Control, the chemically modified EXO-Codes mod-S6, the EXO-Code M1, the chemically modified EXO-Code mod-M1 with modified nucleotides (methyl-cytidine and pseudouridine to confer enhanced stability) were synthesized 5'-upstream of the SNAIL siRNA antisense sequence, separated by a 3-adenosine linker. The SNAIL siRNA sense strand was then conjugated via base pairing and these constructs were electroporated into MDA-MB-231 cells and mesenchymal stem cells (n=3-4). After 24 hours exosomes were collected and RNA was extracted according to the miRNeasy protocol (Qiagen). cDNA was generated using the mirScript cDNA synthesis kit and qPCR was performed using SYBR low ROX (Quanta) against the SNAIL sense strand. Data are plotted as fold improvement in loading over the random control by the delta Ct method+standard error of the mean. Fold improvement in loading was assessed for statistical significance using ANOVA with Tukey post hoc (*=p<0.05, =p<0.001, *=p<0.0001). In MDA-MB-231 cells chemically modified EXO-Codes mod-M1 showed ~118-fold improvement over random control while unmodified EXO-Code M1 showed ~8-fold improvement over random control. In MSCs chemically modified EXO-Code Mod-S6 showed ~21-fold improvement over random control while unmodified EXO-Code S6 showed ~9-fold improvement over random control.

For FIG. 12, donor MDA cells were electroporated with EXO-Code-pre-miRNA chimeras (n=3), EXO-Code and pre-miRNA only controls (n=3, n=2), as well as no RNA growth controls (n=5). The exosomes from these cells were then plated on recipient MDA cells which had been scratched on a glass-bottom 96-well plate. Wound closure between 6 and 10 hours prior to seeding scratched cells with exosomes has been normalized to no-RNA growth controls. Wound area was obtained though programed Zeiss microscopy acquisition and quantified with Axiovision software. Comparing the treatment groups with ANOVA Tukey post-hoc, targeting miR-31 with the enriched sequence (E-31) is better than untargeted miR-31 at alpha of 0.01, p-value miR-31 only vs E-31=0.0011. The scrambled control (S-31) is statistically different from E-31 and 'miR-31 only' at alpha of 0.05, p=0.0308 and 0.0352 respectively. There is no statistically significant difference between the growth controls and the 'miR-31 only' control, nor among the enriched or scrambled sequence aptamer only controls using ANOVA with Tukey post-hoc. To increase stability of the EXO-Codes the DNA templates were translated into RNA using methyl CTP and pseudo UTP in the in vitro reaction.

Representative and non-limiting EXO-Code sequences that can be used alone or in any combination in embodiments of this disclosure, and related information, are shown in FIG. 16, which provides motifs and shared sequence analysis. In particular, FIG. 16: shows in A): Submitting the top 1,000 sequences from the latest selection round to MEME motif algorithm demonstrated highly statistically significant motifs (lowest E-value motifs shown). The most significant motifs from RAW and MSC cells show high similarity. 16B) Less statistically significant motifs from PC-3 and RAW cells show high similarity.

TABLE 2

Common Sequences in the top 10 after final selection round
Common Sequences in the top 10 tested EXO-Codes

| | | |
|---|---|---|
| 1 | CGUGGCUGGUUCGUGCGGGG (SEQ ID NO: 71) | RAW #4\|MSC #9 |
| 2 | GGUCGAGUGAUGCGGGGCGC (SEQ ID NO: 72) | RAW #6\|MSC #8 |
| 3 | UGAUGUAUUUGGUUUGCAAG (SEQ ID NO: 73) | HEK #4\|RAW #8 |
| 4 | UGGAACGUCGAUGUGGGCCG (SEQ ID NO: 74) | MSC #1\|RAW #2 |
| 5 | GCGAUAGGCGGUCGUUGGUC (SEQ ID NO: 75) | MDA #2\|MSC #5 |
| 6 | UCGUAGGUCAGGAAGCGGCG (SEQ ID NO: 76) | MDA #1\|MSC #3 |

Table 2: within the top ten EXO-Code sequences that were tested 6 were present in two cell lines. 1) EXO-Code RAW #4 and MSC #9, 2) EXO-Code RAW #6 and MSC #8, 3) EXO-Code HEK #4 and RAW #8, 4) EXO-Code MSC #1 and RAW #2, 5) EXO-Code MSC #2 and MSC #5, 6) EXO-Code MSC #1 and MSC #3.

Figure 17:
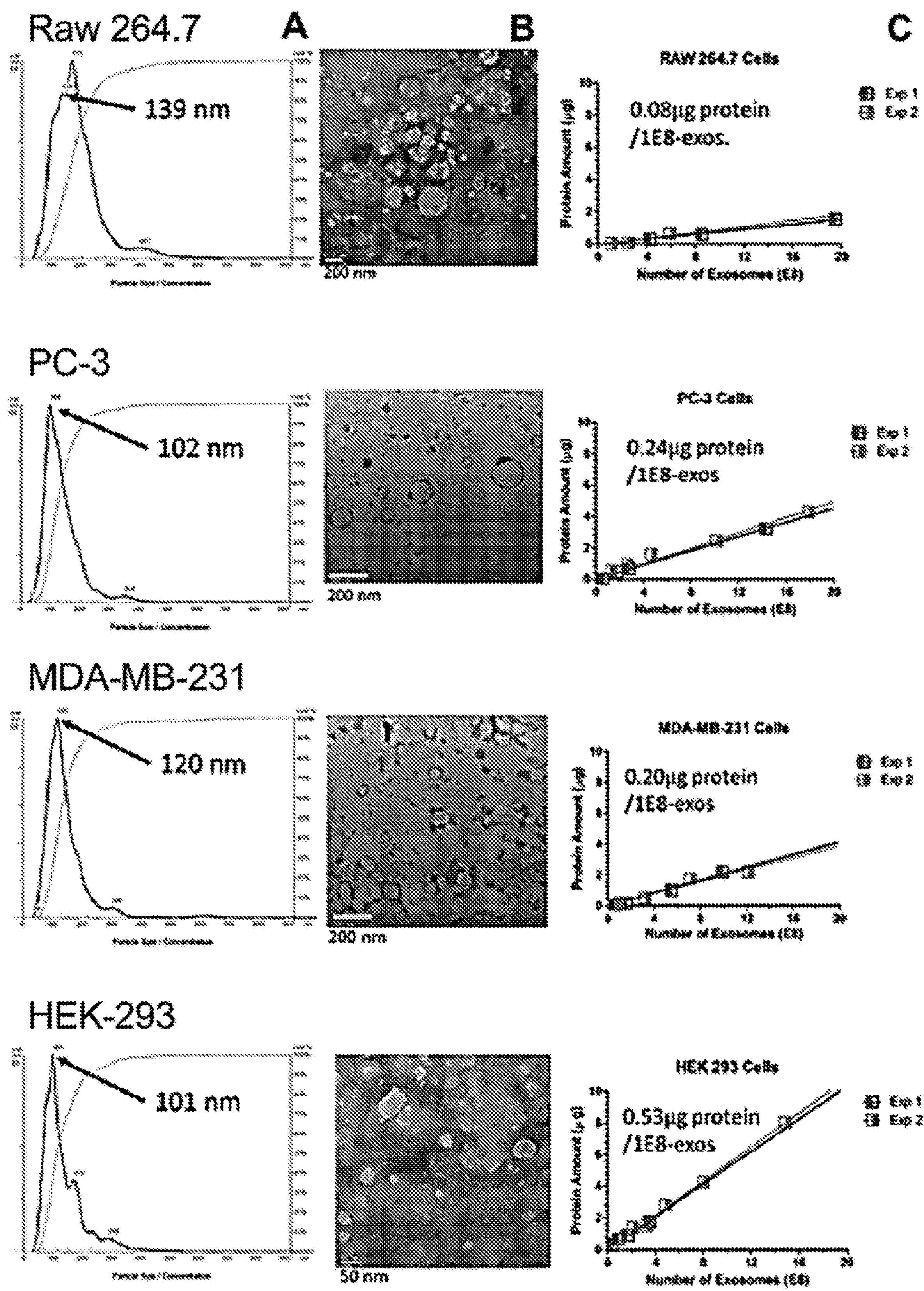
FIG. 17 shows exosome/EV characterization studies (A) Nanoparticle tracking analysis (NTA) of exosome/EV population. (B) Transmission electron microscopy (TEM). NTA and TEM show a majority of exosomes/EVs fall in the expected size range of 30-150 nm. (C) NTA particle counts were also correlated to protein content as a secondary means of vesicle enumeration.

FIG. 17: Exosome/EV Characterization.

In particular, FIG. 17 shows: Exosome/EV characterization studies A) Nanoparticle tracking analysis (NTA) of exosome/EV population. B) Transmission electron microscopy (TEM). NTA and TEM show a majority of exosomes/EVs fall in the expected size range of 30-150 nm. C) NTA particle counts were also correlated to protein content as a secondary means of vesicle enumeration.

Representative and non-limiting exosome sequences provided by this disclosure include but are not limited to the following:

| RANK | SEQUENCE | READ COUNT |
|---|---|---|
| RAW Rd 5 TOP 10 Sequences | | |
| 1 | GAAUGAUCUUGGUUGUCAAC (SEQ ID NO: 77) | 285 |
| 2 | UGGAACGUCGAUGUGGGCCG (SEQ ID NO: 78) | 211 |
| 3 | AGCGAGGUGGAGUGGCGUGG (SEQ ID NO: 79) | 151 |
| 4 | CGUGGCUGGUUCGUGCGGGG (SEQ ID NO: 80) | 142 |
| 5 | GCGCGGGAAGGGUGGCAUGG (SEQ ID NO: 81) | 130 |
| 6 | GAUGGUAUGUUGGAAAGCGA (SEQ ID NO: 82) | 129 |
| 7 | GGUCGAGUGAUGCGGGGCGC (SEQ ID NO: 83) | 106 |
| 8 | GAUGGUAAGUUGGAAAGCGA (SEQ ID NO: 84) | 98 |
| 9 | CAGUAUUAGCAAGGGAGGGG (SEQ ID NO: 85) | 94 |
| 10 | GAGGGGGAGGAGGGCAUGCC (SEQ ID NO: 86) | 80 |
| RAW Rd 7 TOP 10 Sequences | | |
| 1 | UGGAACGUCGAUGUGGGCCG (SEQ ID NO: 87) | 3213 |
| 2 | GGUCGAGUGAUGCGGGGCGC (SEQ ID NO: 88) | 2212 |
| 3 | GAUGGUAAGUUGGAAAGCGA (SEQ ID NO: 89) | 1932 |
| 4 | CGUGGCUGGUUCGUGCGGGG (SEQ ID NO: 90) | 1820 |
| 5 | GAUGGUAUGUUGGAAAGCGA (SEQ ID NO: 91) | 1510 |
| 6 | GCUGGUCAGGAUGCGGGGGC (SEQ ID NO: 92) | 1043 |
| 7 | CAACCUAGGUGCGGGGCGGG (SEQ ID NO: 93) | 970 |
| 8 | GGAAGAUCAAGGUGCGGGGC (SEQ ID NO: 94) | 916 |
| 9 | GGUUCAGGGUGUGGGCCGCC (SEQ ID NO: 95) | 914 |
| 10 | GCGCGGGAAGGGUGGCAUGG (SEQ ID NO: 96) | 831 |
| RAW Rd 10 TOP 10 Sequences | | |
| 1 | GAUGGUAAGUUGGAAAGCGA (SEQ ID NO: 97) | 1645 |
| 2 | UGGAACGUCGAUGUGGGCCG (SEQ ID NO: 98) | 1526 |
| 3 | GAUGGUAUGUUGGAAAGCGA (SEQ ID NO: 99) | 1139 |
| 4 | CGUGGCUGGUUCGUGCGGGG (SEQ ID NO: 100) | 1138 |
| 5 | UUCGUGUAUCUAGUGCAGUC (SEQ ID NO: 101) | 965 |
| 6 | GGUCGAGUGAUGCGGGGCGC (SEQ ID NO: 102) | 877 |
| 7 | UUUCGUGUAUCCUAGUUGCU (SEQ ID NO: 103) | 609 |
| 8 | UGAUGUAUUUGGUUUGCAAG (SEQ ID NO: 104) | 454 |
| 9 | UUCGUGUUCUGGUUGAGUGU (SEQ ID NO: 105) | 406 |
| 10 | GCGCGGGAAGGGUGGCAUGG (SEQ ID NO: 106) | 350 |
| MDA-MB-231 cells, Rd 5 TOP 10 Sequences Round 5 | | |
| 1 | GAGUCUUUCCGUCUUGCGUG (SEQ ID NO: 107) | 142 |
| 2 | AGCGAGUACGCUGCGAUUGC (SEQ ID NO: 108) | 126 |
| 3 | GCGAUGUAUGGUUUUCGGUG (SEQ ID NO: 109) | 104 |
| 4 | CCAGAGGUGAUGGCGGUCGC (SEQ ID NO: 110) | 103 |
| 5 | GGCGAUCGGAAGGCAUGCAC (SEQ ID NO: 111) | 97 |
| 6 | CACUCGAGAUGCCGCGUAGG (SEQ ID NO: 112) | 94 |
| 7 | CACGCAGGCGAGGUGGCAGC (SEQ ID NO: 113) | 93 |
| 8 | CCUUUGUGUCUGCAGGCUCU (SEQ ID NO: 114) | 88 |
| 9 | CCGGGCGUAUCUUGUGGUCG (SEQ ID NO: 115) | 88 |
| 10 | CAUCUGCUCUCGGGGGCACA (SEQ ID NO: 116) | 80 |
| MDA-MB-231 cells, Rd 7 TOP 10 Sequences | | |
| 1 | UCGUAGGUCAGGAAGCGGCG (SEQ ID NO: 117) | 436 |
| 2 | CCGGGCGUAUCUUGUGGUCG (SEQ ID NO: 118) | 417 |
| 3 | GUGGUCGAUAAGCGUACGCG (SEQ ID NO: 119) | 265 |
| 4 | UGCGACGUCGUUAGUGGUAC (SEQ ID NO: 120) | 238 |
| 5 | GGCCUUGGUCGCGUGCUGGC (SEQ ID NO: 121) | 224 |
| 6 | CCAGAGGUGAUGGCGGUCGC (SEQ ID NO: 122) | 210 |
| 7 | CCGCGUGGUUUGUGCGGGUG (SEQ ID NO: 123) | 185 |
| 8 | CCAGAACUUGUGGUACCUGC (SEQ ID NO: 124) | 167 |
| 9 | GCGAUGUAUGGUUUUCGGUG (SEQ ID NO: 125) | 162 |
| 10 | CAUCUGCUCUCGGGGGCACA (SEQ ID NO: 126) | 143 |
| MDA-MB-231 cells, Rd 10 TOP 10 Sequences | | |
| 1 | UCGUAGGUCAGGAAGCGGCG (SEQ ID NO: 127) | 806 |
| 2 | GCGAUAGGCGGUCGUUGGUC (SEQ ID NO: 128) | 644 |
| 3 | CCCGCUUCUUCCUCGGGUGG (SEQ ID NO: 129) | 506 |
| 4 | GUCACUCGGCCUAGUGCGUC (SEQ ID NO: 130) | 406 |
| 5 | CCUGACCUUACUCGGGUGGC (SEQ ID NO: 131) | 309 |
| 6 | GUGGUCGAUAAGCGUACGCG (SEQ ID NO: 132) | 239 |
| 7 | AGGGCGUUUGCUCGCGGGUC (SEQ ID NO: 133) | 235 |
| 8 | CCGGGCGUAUCUUGUGGUCG (SEQ ID NO: 134) | 225 |
| 9 | CAGACGGUACUCAGGUGUGC (SEQ ID NO: 135) | 218 |
| 10 | GGCCUUGGUCGCGUGCUGGC (SEQ ID NO: 136) | 216 |

-continued

| RANK | SEQUENCE | READ COUNT |
|---|---|---|
| | PC-3 cells, Round 5, Top 10 sequences | |
| 1 | GUCGGUGAACGACUGGUGGC (SEQ ID NO: 137) | 13 |
| 2 | GGUUAAUUUUAUGUGUCAAC (SEQ ID NO: 138) | 10 |
| 3 | GGGCUUUCGGCAGGCGGUCG (SEQ ID NO: 139) | 7 |
| 4 | GUGGAUGUAGGGGGACGGGC (SEQ ID NO: 140) | 6 |
| 5 | UGCGAUGUUGUGAGUGGCCC (SEQ ID NO: 141) | 6 |
| 6 | GCAUAUGGGCGCUUGUGUGG (SEQ ID NO: 142) | 5 |
| 7 | GGGUGCGGAAGUCAGUGUGG (SEQ ID NO: 143) | 5 |
| 8 | GAGCUGCAUGUGGCGUUGGG (SEQ ID NO: 144) | 5 |
| 9 | GUGGUAAGGUUGGAAGGUGU (SEQ ID NO: 145) | 4 |
| 10 | GGGCCUUGAUCACGUGGUGC (SEQ ID NO: 146) | 4 |
| | PC-3 cells, Round 7, Top 10 sequences | |
| 1 | GAGGCCUGUGCUAGUAGUGA (SEQ ID NO: 147) | 29 |
| 2 | UGGUAGGUUGGAAGGUCGGG (SEQ ID NO: 148) | 23 |
| 3 | CGUGGUAUGGUUGGAACGGU (SEQ ID NO: 149) | 22 |
| 4 | AAGGGUAAGUUGGAAAGUCG (SEQ ID NO: 150) | 18 |
| 5 | GUGGUAGGUUGGAAGGCCGG (SEQ ID NO: 151) | 15 |
| 6 | GUGGUAGGUUGGAAAGGCUG (SEQ ID NO: 152) | 15 |
| 7 | GGUGGUAUGUUGGAAGGUUG (SEQ ID NO: 153) | 15 |
| 8 | UGCGAUGUUGUGAGUGGCCC (SEQ ID NO: 154) | 14 |
| 9 | AGUGGUAAGUUGGAAUGCAC (SEQ ID NO: 155) | 12 |
| 10 | GGGCCUUGAUCACGUGGUGC (SEQ ID NO: 156) | 10 |
| | PC-3 cells, Round 10, Top 10 sequences | |
| 1 | AAGGCCGGUGCUAGUAGUGA (SEQ ID NO: 157) | 601 |
| 2 | GUGGUAGGUUGGAUCGUCGG (SEQ ID NO: 158) | 248 |
| 3 | UGUGGUAUCGUUGGAAAGCG (SEQ ID NO: 159) | 202 |
| 4 | GGUGGUAGGUUGGAACGGCG (SEQ ID NO: 160) | 198 |
| 5 | AGGUAUGGGCGCUUCGUGGC (SEQ ID NO: 161) | 189 |
| 6 | GUCGUGGUAUGUUGGAGGGC (SEQ ID NO: 162) | 129 |
| 7 | GGGGUAUUGUUGGAACGGCG (SEQ ID NO: 163) | 119 |
| 8 | CGGGUAUAGUUGGAACGUCG (SEQ ID NO: 164) | 117 |
| 9 | GUGGUAGGUUGGAAAGGCUG (SEQ ID NO: 165) | 115 |
| 10 | GUGGUAUGGUUGGAACGCAG (SEQ ID NO: 166) | 113 |
| | Mesenchymal stem cells, Round 5, Top 10 Sequences | |
| 1 | UGGAACGUCGAUGUGGGCCG (SEQ ID NO: 167) | 3577 |
| 2 | GGUUCAGGGUGUGGGCCGCC (SEQ ID NO: 168) | 2510 |
| 3 | GCUGGUCAGGAUGCGGGGGC (SEQ ID NO: 169) | 1835 |
| 4 | CGUGGCUGGUUCGUGCGGGG (SEQ ID NO: 170) | 1806 |
| 5 | GGUCGAGUGAUGCGGGGCGC (SEQ ID NO: 171) | 1662 |
| 6 | CUAGCGACGGUGCGGGGGUG (SEQ ID NO: 172) | 860 |
| 7 | UGGGGAUAAGUAUGUUGCGG (SEQ ID NO: 173) | 790 |
| 8 | UCGUAGGUCAGGAAGCGGCG (SEQ ID NO: 174) | 773 |
| 9 | UGCGAUGUUGUGAGUGGCCC (SEQ ID NO: 175) | 699 |
| 10 | GCGCGGGAAGGGUGGCAUGG (SEQ ID NO: 176) | 688 |
| | Mesenchymal stem cells, Round 7, Top 10 Sequences | |
| 1 | UGGAACGUCGAUGUGGGCCG (SEQ ID NO: 177) | 10617 |
| 2 | GGUUCAGGGUGUGGGCCGCC (SEQ ID NO: 178) | 8276 |
| 3 | UCGUAGGUCAGGAAGCGGCG (SEQ ID NO: 179) | 7463 |
| 4 | AAGGCCGGUGCUAGUAGUGA (SEQ ID NO: 180) | 5257 |
| 5 | GCGAUAGGCGGUCGUUGGUC (SEQ ID NO: 181) | 4499 |
| 6 | GCUGGUCAGGAUGCGGGGGC (SEQ ID NO: 182) | 4458 |
| 7 | GCUGCGAAGUGGGGCAGGUC (SEQ ID NO: 183) | 3919 |
| 8 | GGUCGAGUGAUGCGGGGCGC (SEQ ID NO: 184) | 3480 |
| 9 | CGUGGCUGGUUCGUGCGGGG (SEQ ID NO: 185) | 3367 |
| 10 | GGGCGAAAUUGGCAUGGCCG (SEQ ID NO: 186) | 3197 |
| | HEK Round 5 Top 10 sequences | |
| 1 | AAGGCCGGUGCUAGUAGUGA (SEQ ID NO: 187) | 4818 |
| 2 | UGAUGUAUUGGUAAGUUUCG (SEQ ID NO: 188) | 4816 |
| 3 | UAUAGAUGUGCUAGUUUGCA (SEQ ID NO: 189) | 2566 |
| 4 | UUAGCGUUGUAUUAGUUGCA (SEQ ID NO: 190) | 1788 |
| 5 | AUCGAUGUAUGAGUCAUAUA (SEQ ID NO: 191) | 1612 |
| 6 | AAUUACACUGUGCUAGGAUG (SEQ ID NO: 192) | 1447 |
| 7 | UUGAAGUGUACAUUGUCGUA (SEQ ID NO: 193) | 1292 |

-continued

| RANK | SEQUENCE | READ COUNT |
|---|---|---|
| 8 | UGAUGUGUUAGUUUGAAUGU (SEQ ID NO: 194) | 1254 |
| 9 | UGAAAUGAGACUGGUUUUGC (SEQ ID NO: 195) | 1210 |
| 10 | UGAUGUAUUUGGUUUGCAAG (SEQ ID NO: 196) | 1082 |
| | HEK Round 7 Top 10 sequences | |
| 1 | UGAUGUAUUGGUAAGUUUCG (SEQ ID NO: 197) | 17993 |
| 2 | UAUAGAUGUGCUAGUUUGCA (SEQ ID NO: 198) | 5712 |
| 3 | UUUCGUGUUUAGCGUUUGAC (SEQ ID NO: 199) | 5298 |
| 4 | UGAUGUAUUUGGUUUGCAAG (SEQ ID NO: 200) | 3512 |
| 5 | ACGUGUAUUACUAUUGACUA (SEQ ID NO: 201) | 2615 |
| 6 | GAGGCCUGUGCUAGUAGUGA (SEQ ID NO: 202) | 2461 |
| 7 | UUAGCGUUGUAUUAGUUGCA (SEQ ID NO: 203) | 2367 |
| 8 | UCAUUGUGCUGAAUUGACUA (SEQ ID NO: 204) | 2135 |
| 9 | AAUUACACUGUGCUAGGAUG (SEQ ID NO: 205) | 2046 |
| 10 | AUCGAUGUAUGAGUCAUAUA (SEQ ID NO: 206) | 1825 |

Figure 19:
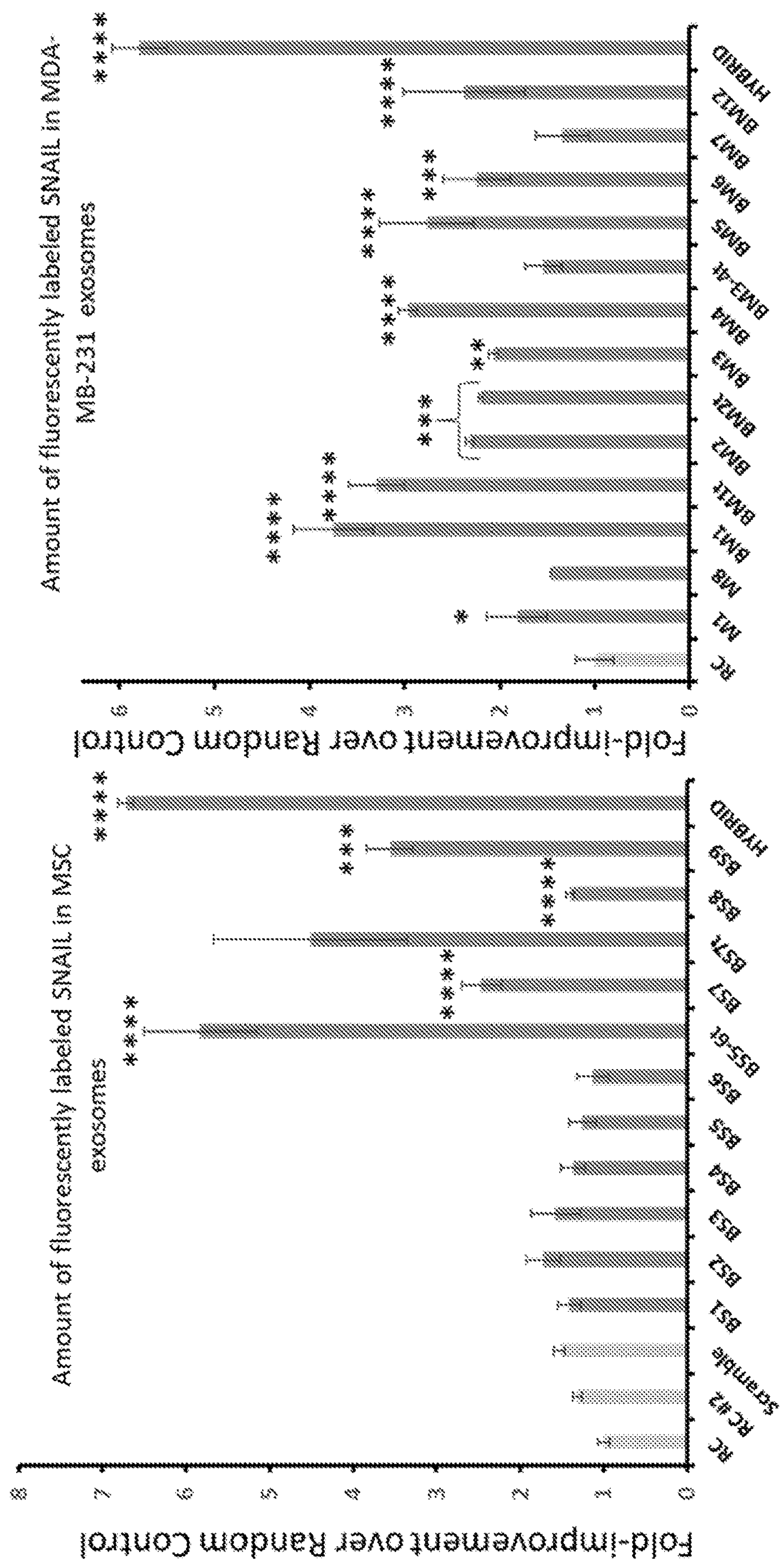
FIG. 19 shows additional sequences for MSC and MDA-MB-231 cells. Specifically, the in silico approach identified motifs and the antisense strand of SNAIL siRNA were synthesized in a continuous strand separated by three adenines. These constructs were annealed to a Cy5-labeled SNAIL sense strand RNA and electroporated at 5 ug of sense fluorescent reporter siRNA per 120,000 MSC or 300,000 MDA-MB-231 cells in triplicate. Cells were cultured in exosome-free media for 24 h and exosomes/EVs were isolated by the Total Exosome Isolation Reagent method. Exosomes/EVs were then re-suspended in PBS and bound to CD63 beads overnight at 4° C. The exosome/EV-bound beads were washed and analyzed by flow cytometry. Fold changes in mean fluorescence intensity over background were plotted. Background was defined as random control bound to Cy5-labeled SNAIL minus the exosome-bound beads with no Cy5-labeled SNAIL electroporated into the producing cells. Several of the in silico predicted motifs shows significant higher enrichment than control. Statistical analysis was performed with one-way ANOVA followed by Dunnett's post-hoc test.
Figure 20:
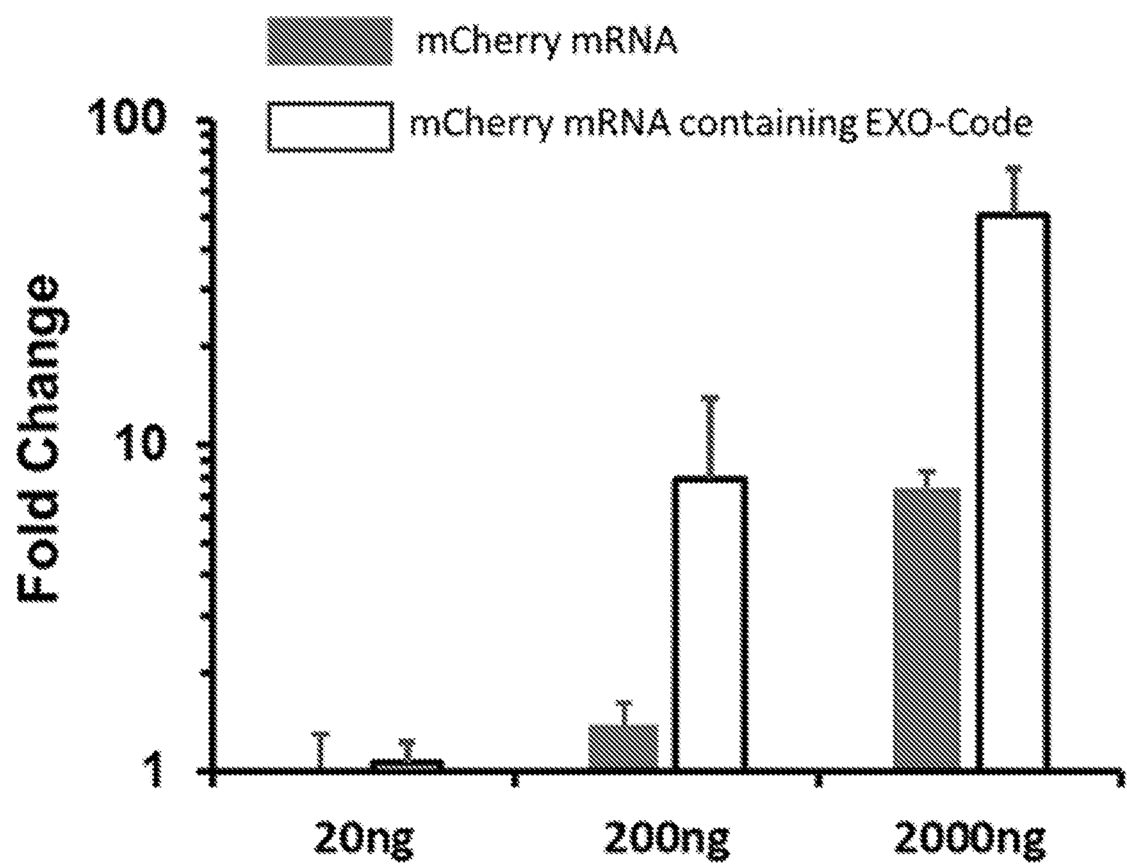
FIG. 20 shows EXO-Codes enhance loading of mCherry mRNA into exosomes of MDA-MB-231 cells by ~7-fold compared to unmodified mCherry mRNA.
Figure 23:
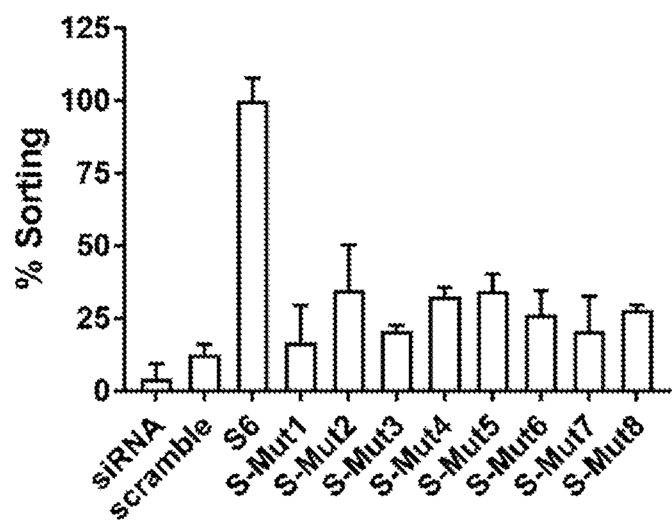
FIG. 23 shows sorting of SNAIL siRNA tagged with an S6 EXO-Code to exosomes derived from MSCs. Mutations were introduced into the S6 EXO-Code to assess the effect on sorting.

FIGS. 18, 19 and 20 include additional and non-limiting embodiments for EXO-Codes predicted from the sequences identified and screened through the method outlined in FIG. 3. In particular, to identify conserved motifs, we analyzed sequences after 3, 5, and 7 rounds of selection showing 16 standard deviations above the average sequence reads of the respective rounds. These sequences were pooled and analyzed using MEME suite. The search criteria was set to include motifs of up to 12 nucleotides that can be present at any number of repetitions within a sequence. There were 8 motifs with high statistical significance for MDA-MB-231 cells, 10 motifs with high statistical significance for mesenchymal stem cells, and 8 motifs with high statistical significance for RAW 264.7 cells. Motifs sharing similar sequence elements were aligned visually and grouped; arrows indicate similar motifs between the cell lines, as shown in FIG. 18. MEME represents motifs as position-dependent letter-probability matrices. Each sequence logo/motif consists of stacks of nucleotide symbols, with one stack representing each position in the sequence. The overall height of the stack indicates sequence conservation at that position, while the height of nucleotides within the stack indicates the relative frequency of the respective nucleotide at that position. Additionally, IUPAC nucleotide codes are shown for the respective motifs.

FIG. 19 provides additional sequences for MSC and MDA-MB-231 cells. Specifically, the in silico approach identified motifs and the antisense strand of SNAIL siRNA were synthesized in a continuous strand separated by three adenines. These constructs were annealed to a Cy5-labeled SNAIL sense strand RNA and electroporated at 5 ug of sense fluorescent reporter siRNA per 120,000 MSC or 300,000 MDA-MB-231 cells in triplicate. Cells were cultured in exosome-free media for 24 h and exosomes/EVs were isolated by the Total Exosome Isolation Reagent method. Exosomes/EVs were then re-suspended in PBS and bound to CD63 beads overnight at 4° C. The exosome/EV-bound beads were washed and analyzed by flow cytometry. Fold changes in mean fluorescence intensity over background were plotted. Background was defined as random control bound to Cy5-labeled SNAIL minus the exosome-bound beads with no Cy5-labeled SNAIL electroporated into the producing cells. Several of the in silico predicted motifs shows significant higher enrichment than control. Statistical analysis was performed with one-way ANOVA followed by Dunnett's post-hoc test.

FIG. 20 presents data obtained with the M8 EXO-Code mCherry (containing the sequence AUCUUGUGGUC (SEQ ID NO:207)) in the 3'-UTR of the mCherry transcript. M8-EXO-Code mCherry (containing the sequence AUCUUGUGGUC in the 3'-UTR of the mCherry transcript) had ~7-fold higher loading capacity into the exosomes of MDA-MB-231 cells than control mCherry RNA. 500,000 MDA cells were electroporated with the mRNA constructs using the NEON electroporation instrument at 3 dose levels in triplicate: 0.1 ug, 1 ug, and 10 ug. Cells were washed in DMEM 3 times and plated into DMEM+10% exosome-depleted-FBS. Cells were cultured for 24 hours and exosomes isolated using the Total Exosome Isolation Reagent from Cell Media (ThermoFisher). Exosomes were pelleted at 13,000 rpm for 1 hr. The supernatant was completely removed and exosomes were resuspended in sterile PBS (20 ul). Exosome samples were treated with 1 ul RNAse A/T1 for 1 hr at 37° C. Exosome samples were lysed with 500 ul of Qiazol and RNA was extracted according to the Qiagen miRNeasy protocol and RNA was eluted in 20 ul of RNAse free water. cDNA from each sample was generated using the NEB Protoscript II kit using a maximum input of 6 ul of exosomal RNA. mCherry was quantified by qPCR using Quanta SYBR mastermix (FP: CCTGTCCCCTCAGTTCATGT RP: CCCATGGTCTTCTTCTGCAT). The M8 EXO-Code mCherry (containing the sequence AUCUUGUGGUC (SEQ ID NO:207)) enhanced loading of mCherry mRNA into exosomes of MDA-MB-231 cells by ~7-fold compared to unmodified mCherry mRNA.

Example 2

To assess the importance of specific nucleotides to the sorting potential of identified EXO-Code motifs, mutant constructs containing single mutations were synthesized. In each case, C was mutated to G and vice versa, while A was mutated to U, and vice versa except for the shared sequence mutant 4 where a C to A mutation was opted for since in the motif this position was more often C, G, or U than A. The motifs and motif hybrids were synthesized 5'-upstream of the SNAIL siRNA sequence spaced with four A nucleotides. For the Hybrid sequence (5'-AAGUGGCGUG-3') (SEQ ID NO:208), the motif was continuous with the antisense SNAIL sequence and conjugated to the APC-fluorescently labeled sense strand. For both the M8 (5'-AUCUUGUGGUC-3') (SEQ ID NO:207) and S6 (5'-AUGCGGGGGC-3') (SEQ ID NO:209) motifs, this orientation was swapped so that the active anti-sense strand was the fluorescent reporter being conjugated. MDA or MSC were electroporated with each construct in triplicate and washed 5 times before being plated. Cell media was collected after 24 h and exosomes were isolated and resuspended in 200 ul of PBS. Total fluorescent signal was obtained by lysing 100 ul of exosomes with 50 ul of 10% Triton in PBS and analyzed at 633/660 nm using a SpectraMax plate reader. Average APC-signal per exosome was also obtained using the MACsQuant flow cytometer following manufacturer settings for exosome analysis.

For the Hybrid sequence (AAGUGGCGUG) (SEQ ID NO:208), the motif was continuous with the anti-sense SNAIL sequence and annealed to the APC-fluorescently labeled sense strand. The sequences for the SNAIL siRNA was as follows: APC-SNAIL (anti-sense=GUGG CUUCGGAUGUGCAUCUU (SEQ ID NO:210), sense=GAUGC ACAUCCGAAGCCACUU (SEQ ID NO:211)). For this experiment, MDA-MB-231 cells were electroporated with the constructs and washed three times to remove unincorporated RNA. Cells were cultured for 24 h before media was collected and spun down for 30 min at 2,000 g. The media supernatant was combined with 0.5 volumes of Total Exosome Isolation Reagent from Cell Media (ThermoFisher) and kept at 4° C. overnight. Exosomes were pelleted at 13,000 rpm for 1 hr. The supernatant was completely removed and exosomes were resuspended in sterile PBS (200 ul). Total fluorescent signal was obtained by lysing 100 ul of exosomes with 50 ul of 10% Triton in PBS and reading at 633/660 nm on a SpectraMax plate reader. 50 ul of each exosome sample was also analyzed on the MacsQuant flow cytometer according to manufacturer specifications for exosomes.

As shown in the image, each mutation led to a decrease in the loading of the SNAIL siRNA into exosomes. The decrease in sorting is significant with $p<0.001$ for HMut1 compared to the Hybrid sequence, and $p<0.05$ for HMut2 and HMut4 compared to the Hybrid motif.

For the M8 Motif (5' AUCUUGUGGUC) (SEQ ID NO:207), M8 Full and the respective sequences containing the mutations, the EXO-Code sequences were a continuous strand with the sense SNAIL siRNA connected through a four A nucleotide spacer. The fluorescently labeled SNAIL-antisense was annealed to the EXO-Code/SNAIL sense strand RNA. The sequences for the SNAIL siRNA was as follows: APC-SNAIL (anti-sense=GUGGCU UCGGAUGUGCAUCUU (SEQ ID NO:210), sense=GAUGC ACAUCCGAAGCCACUU (SEQ ID NO:211)). For this experiment, MDA-MB-231 cells were electroporated with the constructs and washed three times to remove unincorporated RNA. Cells were cultured for 24 h before media was collected and spun down for 30 min at 2,000 g. The media supernatant was combined with 0.5 volumes of Total Exosome Isolation Reagent from Cell Media (ThermoFisher) and kept at 4° C. overnight. Exosomes were pelleted at 13,000 rpm for 1 hr. The supernatant was completely removed and exosomes were resuspended in sterile PBS (200 ul). Total fluorescent signal was obtained by lysing 100 ul of exosomes with 50 ul of 10% Triton in PBS and reading at 633/660 nm on a SpectraMax plate reader. 50 ul of each exosome sample was also analyzed on the MacsQuant flow cytometer according to manufacturer specifications for exosomes.

As shown in the image, each mutation led to a decrease in the loading of the SNAIL siRNA into exosomes derived from MDA-MB-231 cells. The decrease in sorting is significant with $p<0.0001$ for M8 motif, Mut1, Mut2, Mut3, Mut4, Mut5, Mut6, scrambled sequence compared to M8 Full sequence; $p<0.001$ for Mut1, Mut2 compared to the M8 motif; $p<0.0001$ for Mut3, Mut4, Mut5, scrambled sequence compared to the M8 motif; and $p<0.01$ for Mut6 compared to the M8 Motif.

For the S6 (5'-AUGCGGGGGC-3') (SEQ ID NO:209) and the respective sequences containing the mutations, the EXO-Code sequences were a continuous strand with the sense SNAIL siRNA connected through a four A nucleotide spacer. The S6 motif is the shortened motif of the MSC6 sequence: 5'-GCUGGUCAGGAUGCGGGGGC-3' (SEQ ID NO:212). The fluorescently labeled SNAIL-antisense was annealed to the EXO-Code/SNAIL sense strand RNA. The sequences for the SNAIL siRNA was as follows: APC-SNAIL (anti-sense=GUGGCUUCGG AUGUGCAUCUU (SEQ ID NO:210), sense= GAUGCACAUCCGAAGCCACUU (SEQ ID NO:211)). For this experiment, mesenchymal stem cells (MSC) were electroporated with the constructs and washed three times to remove unincorporated RNA. Cells were cultured for 24 h before media was collected and spun down for 30 min at 2,000 g. The media supernatant was combined with 0.5 volumes of Total Exosome Isolation Reagent from Cell Media (ThermoFisher) and kept at 4° C. overnight. Exosomes were pelleted at 13,000 rpm for 1 hr. The supernatant was completely removed and exosomes were resuspended in sterile PBS (200 ul). Total fluorescent signal was obtained by lysing 100 ul of exosomes with 50 ul of 10% Triton in PBS and reading at 633/660 nm on a SpectraMax plate reader. 50 ul of each exosome sample was also analyzed on the MacsQuant flow cytometer according to manufacturer specifications for exosomes.

As shown in the image, each mutation led to a decrease in the loading of the SNAIL siRNA into exosomes derived from MSC. The decrease in sorting is statistically significant with $p<0.0001$ for siRNA (unmodified siRNA), scramble, S6, S-Mut1, S-Mut2, S-Mut3, S-Mut4, S-Mut5, S-Mut6, S-Mut7, and S-Mut8 compared to the S6-EXO-Code/siRNA construct.

While the invention has been described through specific embodiments, routine modifications will be apparent to those skilled in the art and such modifications are intended to be within the scope of the present invention.

The invention claimed is:

1. An RNA polynucleotide comprising the sequence 5'-AAGUGGCGUG-3' (SEQ ID NO:208) and a functional segment comprising the sequence of a short hairpin RNA (shRNA), or a short interfering RNA (siRNA), or a microRNA (miRNA), and wherein the RNA polynucleotide is comprised by a membranous structure.

2. The RNA polynucleotide of claim 1, wherein the membranous structure is one of: an exosome, a vesicle, a microvesicle, a micro-particle, an endosomal derived vesicle, a multivesicular body, or an apoptotic body.

3. The RNA polynucleotide of claim 2, wherein the RNA polynucleotide is comprised by the exosome.

* * * * *